(12) United States Patent
Duesterhoft et al.

(10) Patent No.: US 10,158,928 B2
(45) Date of Patent: Dec. 18, 2018

(54) APPURTENANCES FOR REPORTING INFORMATION REGARDING WOUND DRESSINGS

(75) Inventors: Paul Duesterhoft, Issaquah, WA (US); Nicholas Dykstra, Seattle, WA (US); Daniel Hawkins, Bellevue, WA (US); Roderick A. Hyde, Redmond, WA (US); Jordin T. Kare, Seattle, WA (US); Eric C. Leuthardt, St Louis, MO (US); Elizabeth L. Schubert, Bellevue, WA (US); Clarence T. Tegreene, Bellevue, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 1452 days.

(21) Appl. No.: 13/445,174

(22) Filed: Apr. 12, 2012

(65) Prior Publication Data

US 2013/0274629 A1    Oct. 17, 2013

Related U.S. Application Data

(63) Continuation-in-part of application No. 13/445,220, filed on Apr. 12, 2012, now Pat. No. 9,084,530.

(51) Int. Cl.
*H04Q 9/00* (2006.01)
*A61B 5/00* (2006.01)
(Continued)

(52) U.S. Cl.
CPC ............ *H04Q 9/00* (2013.01); *A61B 5/002* (2013.01); *A61B 5/0015* (2013.01);
(Continued)

(58) Field of Classification Search
CPC .................................................. A61M 1/0088
(Continued)

(56) References Cited

U.S. PATENT DOCUMENTS 3,927,669 A * 12/1975 Glatt ................. A61F 13/00021
602/47
4,384,288 A 5/1983 Walton
(Continued)

FOREIGN PATENT DOCUMENTS

EP       0 430 608 A1    6/1991
WO       WO 00/08203     2/2000
(Continued)

OTHER PUBLICATIONS

U.S. Appl. No. 13/795,667, Duesterhoft et al.
(Continued)

*Primary Examiner* — May Abouelela
(74) *Attorney, Agent, or Firm* — Dorsey & Whitney LLP

(57) ABSTRACT

Appurtenances to wound dressings are described, which include: a substrate configured to mechanically or chemically attach to a wound dressing; a transmission unit attached to a surface of the substrate, the transmission unit including circuitry and at least one antenna, the transmission unit configured to transmit a signal; and a projection operably attached to the transmission unit, the projection of a size and shape to extend into an interior region of the wound dressing and configured to sample a fluid associated with a wound.

22 Claims, 21 Drawing Sheets

(51) Int. Cl.

| | | |
|---|---|---|
| *A61B 10/00* | (2006.01) | |
| *A61F 13/00* | (2006.01) | |
| *G06F 19/00* | (2018.01) | |
| *G16H 40/67* | (2018.01) | |
| *A61M 1/00* | (2006.01) | |
| *A61B 5/145* | (2006.01) | |

(52) U.S. Cl.
CPC ............ *A61B 5/0022* (2013.01); *A61B 5/445* (2013.01); *A61B 10/0045* (2013.01); *A61F 13/00051* (2013.01); *G06F 19/00* (2013.01); *G16H 40/67* (2018.01); *A61B 5/14539* (2013.01); *A61M 1/0088* (2013.01)

(58) Field of Classification Search
USPC ...................... 600/573, 583; 602/42; 604/319
See application file for complete search history.

(56) References Cited

U.S. PATENT DOCUMENTS

| | | | |
|---|---|---|---|
| 4,430,998 A * | 2/1984 | Harvey | A61B 17/085 606/216 |
| 4,753,232 A * | 6/1988 | Ward | A61F 13/023 602/52 |
| 4,924,866 A | 5/1990 | Yoon | |
| 5,047,047 A | 9/1991 | Yoon | |
| 5,507,775 A | 4/1996 | Ger et al. | |
| 5,704,352 A | 1/1998 | Tremblay et al. | |
| 5,876,365 A * | 3/1999 | Hart | A61F 13/023 602/79 |
| 5,904,671 A | 5/1999 | Navot et al. | |
| 5,912,114 A | 6/1999 | Hutchinson et al. | |
| 5,939,205 A | 8/1999 | Yokoyama et al. | |
| 5,964,723 A | 10/1999 | Augustine | |
| 5,986,163 A | 11/1999 | Augustine | |
| 6,037,879 A | 3/2000 | Tuttle | |
| 6,248,084 B1 | 6/2001 | Augustine et al. | |
| 6,270,455 B1 | 8/2001 | Brown | |
| 6,283,938 B1 | 9/2001 | McConnell | |
| 6,348,640 B1 | 2/2002 | Navot et al. | |
| 6,420,622 B1 | 7/2002 | Johnston et al. | |
| 6,569,189 B1 | 5/2003 | Augustine et al. | |
| 6,693,513 B2 | 2/2004 | Tuttle | |
| 6,863,220 B2 | 3/2005 | Selker | |
| 6,889,165 B2 | 5/2005 | Lind et al. | |
| 6,963,772 B2 | 11/2005 | Bloom et al. | |
| 7,030,764 B2 | 4/2006 | Smith et al. | |
| 7,055,754 B2 | 6/2006 | Forster | |
| 7,215,976 B2 | 5/2007 | Brideglall | |
| 7,297,112 B2 | 11/2007 | Zhou et al. | |
| 7,361,184 B2 | 4/2008 | Joshi | |
| 7,372,780 B1 | 5/2008 | Braunberger | |
| 7,411,505 B2 | 8/2008 | Smith et al. | |
| 7,446,660 B2 | 11/2008 | Posamentier | |
| 7,479,886 B2 | 1/2009 | Burr | |
| 7,507,675 B2 | 3/2009 | Zuilhof et al. | |
| 7,520,872 B2 | 4/2009 | Biggie et al. | |
| 7,612,424 B1 | 11/2009 | Espinosa et al. | |
| 7,666,151 B2 | 2/2010 | Sullivan et al. | |
| 7,667,606 B2 | 2/2010 | Packert et al. | |
| 7,703,334 B2 | 4/2010 | Cochran | |
| 7,724,136 B2 | 5/2010 | Posamentier | |
| 7,794,925 B2 | 9/2010 | Cullen | |
| 7,813,226 B2 | 10/2010 | Braunberger | |
| 7,825,776 B2 | 11/2010 | Smith et al. | |
| 7,838,717 B2 | 11/2010 | Haggstrom et al. | |
| 7,883,494 B2 * | 2/2011 | Martin | A61M 1/0058 424/447 |
| 7,896,856 B2 | 3/2011 | Petrosenko et al. | |
| 7,914,867 B2 | 3/2011 | Mori et al. | |
| 7,945,302 B2 | 5/2011 | McAdams | |
| 7,951,605 B2 | 5/2011 | Pitner et al. | |
| 7,964,390 B2 | 6/2011 | Rozakis et al. | |
| 7,986,235 B2 | 7/2011 | Posamentier | |
| 8,014,234 B2 | 9/2011 | Braunberger | |
| 8,048,046 B2 | 11/2011 | Hudspeth et al. | |
| 8,057,446 B2 | 11/2011 | Kane et al. | |
| 8,257,328 B2 | 9/2012 | Augustine et al. | |
| 8,350,116 B2 | 1/2013 | Lockwood et al. | |
| 8,376,972 B2 | 2/2013 | Fleischmann | |
| 8,690,845 B2 | 4/2014 | Long et al. | |
| 8,760,295 B2 * | 6/2014 | Forster | A61B 5/445 340/425.2 |
| 8,785,713 B2 | 7/2014 | Hong et al. | |
| 8,795,257 B2 * | 8/2014 | Coulthard | A61M 1/0031 604/313 |
| 8,808,274 B2 | 8/2014 | Hartwell | |
| 8,945,030 B2 | 2/2015 | Weston | |
| 8,946,499 B2 | 2/2015 | Iyer et al. | |
| 9,011,393 B2 | 4/2015 | Kazala, Jr. et al. | |
| 9,050,398 B2 * | 6/2015 | Armstrong | A61M 1/0088 |
| 9,168,180 B2 | 10/2015 | Ha et al. | |
| 9,422,934 B2 * | 8/2016 | Locke | F04B 53/00 |
| 2003/0199783 A1 | 10/2003 | Bloom et al. | |
| 2003/0216663 A1 | 11/2003 | Jersey-Willuhn et al. | |
| 2004/0073151 A1 * | 4/2004 | Weston | A61F 15/008 602/41 |
| 2004/0210280 A1 | 10/2004 | Liedtke | |
| 2006/0036145 A1 | 2/2006 | Brister et al. | |
| 2006/0047218 A1 | 3/2006 | Bloom et al. | |
| 2007/0171076 A1 | 7/2007 | Stevens et al. | |
| 2007/0203442 A1 | 8/2007 | Bechert et al. | |
| 2007/0204691 A1 | 9/2007 | Bogner et al. | |
| 2007/0231380 A1 | 10/2007 | Shah et al. | |
| 2007/0247316 A1 | 10/2007 | Wildman et al. | |
| 2007/0252712 A1 | 11/2007 | Allen et al. | |
| 2007/0269851 A1 | 11/2007 | Sanders et al. | |
| 2008/0132821 A1 | 6/2008 | Propp et al. | |
| 2008/0166397 A1 | 7/2008 | Trotter et al. | |
| 2008/0171957 A1 | 7/2008 | Connolly et al. | |
| 2008/0234616 A1 | 9/2008 | Shives et al. | |
| 2009/0167495 A1 | 7/2009 | Smith et al. | |
| 2009/0192369 A1 | 7/2009 | Say et al. | |
| 2009/0209883 A1 | 8/2009 | Higgins et al. | |
| 2009/0227969 A1 | 9/2009 | Jaeb et al. | |
| 2009/0243813 A1 | 10/2009 | Smith et al. | |
| 2009/0299161 A1 | 12/2009 | Cullen et al. | |
| 2010/0010477 A1 | 1/2010 | Augustine et al. | |
| 2010/0022990 A1 | 1/2010 | Karpowicz et al. | |
| 2010/0030167 A1 | 2/2010 | Thirstrup et al. | |
| 2010/0100061 A1 | 4/2010 | Odland | |
| 2010/0125258 A1 | 5/2010 | Coulthard et al. | |
| 2010/0166694 A1 | 7/2010 | Stephens et al. | |
| 2010/0204606 A1 | 8/2010 | Kim et al. | |
| 2010/0228206 A1 * | 9/2010 | Larsson | A61M 1/0084 604/319 |
| 2010/0249733 A9 | 9/2010 | Blott et al. | |
| 2010/0331634 A1 | 12/2010 | Müller et al. | |
| 2011/0015591 A1 | 1/2011 | Hanson et al. | |
| 2011/0034906 A1 | 2/2011 | Malhi | |
| 2011/0054340 A1 | 3/2011 | Russ et al. | |
| 2011/0082356 A1 | 4/2011 | Yang et al. | |
| 2011/0092927 A1 | 4/2011 | Wilkes et al. | |
| 2011/0105854 A1 | 5/2011 | Kiani et al. | |
| 2011/0140703 A1 | 6/2011 | Chiao et al. | |
| 2011/0160548 A1 | 6/2011 | Forster | |
| 2011/0172582 A1 | 7/2011 | Darian | |
| 2011/0178375 A1 | 7/2011 | Forster | |
| 2011/0213559 A1 | 9/2011 | Pollack et al. | |
| 2012/0010099 A1 | 1/2012 | Stephens et al. | |
| 2012/0016322 A1 | 1/2012 | Coulthard et al. | |
| 2012/0035560 A1 | 2/2012 | Eddy et al. | |
| 2012/0078157 A1 | 3/2012 | Ravikumar et al. | |
| 2012/0109034 A1 | 5/2012 | Locke et al. | |
| 2012/0130325 A1 | 5/2012 | Blott et al. | |
| 2012/0238931 A1 * | 9/2012 | Rastegar | A61F 13/0246 602/44 |
| 2012/0245540 A1 | 9/2012 | Zimnitsky et al. | |
| 2013/0053799 A1 | 2/2013 | Locke et al. | |
| 2013/0261409 A1 | 10/2013 | Pathak et al. | |
| 2013/0304006 A1 | 11/2013 | Toth | |
| 2013/0304007 A1 | 11/2013 | Toth | |
| 2013/0317405 A1 | 11/2013 | Ha et al. | |

(56) References Cited

U.S. PATENT DOCUMENTS

2013/0317406 A1 11/2013 Locke et al.
2015/0208961 A1 7/2015 Duesterhoft et al.
2015/0290045 A1 10/2015 Fan et al.

FOREIGN PATENT DOCUMENTS

| WO | WO 03/040406 | A2 | 5/2003 |
|---|---|---|---|
| WO | WO 2005/009328 | A1 | 2/2005 |
| WO | WO 2007/130239 | A1 | 11/2007 |
| WO | WO 2012/057882 | A1 | 5/2012 |

OTHER PUBLICATIONS

Bluestein et al.; "Pressure Ulcers: Prevention, Evaluation, and Management"; American Family Physician; Nov. 15, 2008; pp. 1186-1194; vol. 78, No. 10; American Academy of Family Physicians.
Clay, Karen S.; "Preventing pressure ulcers in your facility: Karen S. Clay, RN, BSN, CWCN, presents a primer on how to protect frail residents—and avoid costly reprimands"; bearing a date of 2004; 14 pages; HCPro, Inc.
Dowd et al.; "Survey of bacterial diversity in chronic wounds using Pyrosequencing, DGGE, and full ribosome shotgun sequencing"; BMC Microbiology; bearing a date of 2008, published Mar. 6, 2008; pp. 1-15; vol. 8, No. 43; BioMed Central Ltd.
Grist et al.; "Optical Oxygen Sensors for Applications in Microfluidic Cell Culture"; Sensors; bearing a date of 2010, published Oct. 15, 2010; pp. 9286-9316; vol. 10; MDPI; Basel, Switzerland.
PCT International Search Report; International App. No. PCT/US13/36000; dated Jul. 5, 2013; pp. 1-3.
PCT International Search Report; International App. No. PCT/US2013/035993; dated Jun. 25, 2013; pp. 1-2.
DeHennis et al.; "A Wireless Microsystem for the Remote Sensing of Pressure, Temperature, and Relative Humidity"; Journal of Microelectromechanical Systems; Feb. 2005; pp. 12-22; vol. 14, No. 1; IEEE.
Mehmood et al.; "Applications of modern sensors and wireless technology in effective wound management"; Journal of Biomedical Materials Research B: Applied Biomaterials; bearing a date of Sep. 27, 2013; pp. 1-11; Wiley Periodicals, Inc.
U.S. Appl. No. 14/252,136, Duesterhoft et al.
U.S. Appl. No. 14/252,049, Allin et al.
U.S. Appl. No. 14/719,639, Duesterhoft et al.
"Body-fluid battery"; Science News; Sep. 10, 2005; pp. 1-2; located at http://findarticles.com/p/articles/mi_m1200/is_11_168/ai_n15674798/; Science Service, Inc. and Gale Group.
Goodisman, Jerry; "Observations on Lemon Cells"; Journal of Chemical Education; Apr. 2001; pp. 516-518; vol. 78, No. 4.
Huang et al.; "Development of an $IrO_x$ Micro pH Sensor Array on Flexible Polymer Substrate"; Nanosensors and Microsensors for Bio-Systems 2008, edited by Vijay K. Varadan, Proc. of SPIE, vol. 6931, 693104; 2008; pp. 1-9.
Huang et al.; "Investigation of Repeatability of Sol-Gel Iridium Oxide pH Sensor on Flexible Substrate"; Micro- and Nanotechnology: Materials, Processes, Packaging, and Systems IV, edited by Jung-Chih Chiao et al., Proc. of SPIE, vol. 7269, 726916; 2008; pp. 1-9.
U.S. Appl. No. 13/491,677, Duesterhoft et al.
U.S. Appl. No. 13/445,220, Duesterhoft et al.
Karthik Mns; "Could blood be used to power batteries?"; Feb. 2009; pp. 1-4; located at: http://hoowstuffworks.blogspot.com/2009/02/could-blood-be-used-to-power-batteries.html.
Lee et al.; "Water Activated Disposable and Long Shelf Life Microbatteries"; 2003; pp. 387-390; IEEE.
Löfgren et al.; "Low-power humidity sensor for RFID applications"; Multi-Material Micro Manufacture; 2008; 4 pages; Cardiff University.
Nature News; "A miniature biofuel cell operating in a physiological buffer"; Nature; Nov. 12, 2002; pp. 1-2; located at http://www.nature.com/news/2002/021112/full/news021111-1.html.
Pan et al.; "Development of the real-time pH sensing system for array sensors"; Sensors and Actuators B 108; 2005; pp. 870-876; Elsevier B.V.
Pushparaj et al.; "Flexible energy storage devices based on nanocomposite paper"; PNAS; Aug. 21, 2007; pp. 13574-13577; vol. 104, No. 34; The National Academy of Sciences of the USA.
Sammoura et al.; "Water-activated disposable and long shelf life microbatteries"; Sensors and Actuators A 111; 2004; pp. 79-86; Elsevier B.V.
Sidén et al.; "The 'Smart' Diaper Moisture Detection System"; IEEE MTT-S Digest, WE4B-3; 2004; pp. 659-662; IEEE.
University of Texas Arlington, Office of Technology Management; "Smart Wound Condition Monitoring pH Sensor Array on Flexible Substrate; Technology Summary; printed on Apr. 12, 2012; pp. 1-2.
European Search Report; European App. No. EP 13 77 5331; dated Nov. 6, 2015 (received by our Agent on Nov. 12, 2015); pp. 1-3.
European Search Report; European App. No. EP 13 77 5973; dated Nov. 4, 2015 (received by our Agent on Nov. 12, 2015); pp. 1-3.
Abhisam; "RFID systems for pharmaceutical distributors to meet the new FDA regulations on drugs"; Discover the power of e-learning!; bearing a date of 2006; pp. 1-7; Abhisam Software.
Alien Technology; "Battery Assisted Passive Tags"; Alien Technology brochure; downloaded from the web Oct. 17, 2011; pp. 1-2; located at: http://www.alientechnology.com/docs/AT_DS_BAP.pdf; Alien Technology Corp.
Berggren et al.; "Capacitive Biosensors"; Electroanalysis; bearing a date of 2001; pp. 173-180; vol. 13, No. 3; Wiley-VCH Verlag GmbH.
Chawla et al.; "An Overview of Passive RFID"; IEEE Applications & Practice; Sep. 2007; pp. 11-17; IEEE.
Chen et al.; "A 2G-RFID-Based E-Healthcare System"; IEEE Wireless Communications; Feb. 2010; pp. 37-43; IEEE.
Chen et al.; "Ultrasonic Measurement System with Infrared Communication Technology"; Journal of Computers; Nov. 2011; pp. 2468-2475; vol. 6, No. 11; Academy Publisher.
Collier, Mark; "Recognition and management of wound infections"; World Wide Wounds; Jan. 2004; pp. 1-9.
Cui et al.; "Nanowire Nanosensors for Highly Sensitive and Selective Detection of Biological and Chemical Species"; Science; Aug. 17, 2001; pp. 1289-1292, and 1 cover page; vol. 293; American Association for the Advancement of Science.
Cutting et al.; "Criteria for identifying wound infection"; Journal of Wound Care; Jun. 1994; pp. 198-201; vol. 3, No. 4.
Fadlullah et al; "Indoor High-Bandwidth Optical Wireless Links for Sensor Networks"; Journal of Lightwave Technology; Nov. 1, 2010; pp. 3086-3094; vol. 28, No. 21; IEEE.
Finkenzeller, Klaus; "Fundamental Operating Principles" Chapter 3 of the RFID Handbook: Fundamentals and Applications in Contactless Smart Cards and Identification; bearing a date of 2003; pp. 29-59; John Wiley & Sons, Ltd.
Fisher et al.; "Tracking the social dimensions of RFID systems in hospitals"; International Journal of Medical Informatics; bearing a date of 2008; pp. 176-183; vol. 77; Elsevier Ireland Ltd.
Fisher, Jill A.; "Indoor Positioning and Digital Management: Emerging Surveillance Regimes in Hospitals"; Chapter 5 in T. Monahan (Ed), Surveillance and Security: Technological Politics and Power in Everyday Life; May 23, 2006; pp. 77-88; Routledge.
Frost & Sullivan; "Advances in Wound Healing Techniques"; Technical Insights; Publication D11A; bearing a date of 2008; pp. 1-118; Frost & Sullivan.
Frost & Sullivan; "An Overview of Ulceration Wounds"; Publication M4BB-54; Dec. 2009; pp. 1-77; Frost & Sullivan.
Frost & Sullivan; "U.S. Advanced Wound Care Market"; Publication N71A-54; Aug. 2010; pp. 1-90; Frost & Sullivan.
Gray, David; "Assessment, Diagnosis and Treatment of Infection"; Wounds UK; bearing a date of 2011; pp. 4-9; vol. 7, No. 2, supplement.
Ibridge Network; "pH Sensor Array on Flexible Substrate for Wound Care (UTA Ref. No. 08-21)"; Nov. 28, 2011; pp. 1-2; Kauffman Innovation Network, Inc.

(56) References Cited

OTHER PUBLICATIONS

Intel; "WISP: Wireless Identification and Sensing Platform"; Intel Labs Seattle; printed on Oct. 8, 2011; pp. 1-4; located at http://www.seattle.intel-research.net/WISP/.

Intelleflex; "Worldwide RFID UHF Map"; printed on Oct. 17, 2011; p. 1; located at: http://www.intelleflex.com/pdf/Worldwide_UHF_Chart.pdf; Intelleflex Corporation Kavehrad, Mohsen; "Sustainable Energy-Efficient Wireless Applications Using Light"; IEEE Communications Magazine; Dec. 2010; pp. 66-73; IEEE.

Kelly-Quintos et al.; "Characterization of the Opsonic and Protective Activity Against *Staphylococcus aureus* of Fully Human Monoclonal Antibodies Specific for the Bacterial Surface Polysaccharide Poly-N-Acetylglucosamine"; Infection and Immunity; May 2006; pp. 2742-2750; vol. 74, No. 5; American Society for Microbiology.

Lim et al.; "A Micromechanical Biosensor with Interdigitated Capacitor Readout"; Proceedings of the 2011 IEEE/ICME International Conference on Complex Medical Engineering; May 22-25, 2011; pp. 42-46; IEEE.

McColl et al.; "Monitoring moisture without disturbing the wound dressing"; Wounds UK; bearing a date of 2009; pp. 94-96, and 98-99; vol. 5, No. 3.

Murata Manufacturing Co., Ltd.; "Piezoelectric Sound Components"; Cat. No. P37E-23; Nov. 2009; pp. 1-33, and two cover pages.

Murata Manufacturing Co., Ltd.; "Ultrasonic Sensor Application Manual"; Cat. No. S15E-5; Aug. 2009; pp. 1-3, and 2-14, and one supplemental page.

Ohno et al.; "Graphene Field-Effect Transistors for Label-Free Biological Sensors"; IEEE Sensors 2010 Conference Proceedings; Nov. 1-4, 2010; pp. 903-906; IEEE.

Pacific Northwest National Laboratory; "Juvenile Salmon Acoustic Telemetry System (JSATS) Acoustic Transmitters"; Mar. 2010; pp. 1-2.

Patauner et al.; "High Speed RFID/NFC at the Frequency of 13.56 MHz"; presented at the First International EURASIP Workshop on RFID Technology; Sep. 24-25, 2007; pp. 1-4.

Ruhanen et al.; "Sensor-enabled RFID tag handbook"; Building Radio Frequency Identification for the Global Environment; Jan. 2008; pp. 1-47; IST-2005-033546; European Commission.

Sample et al.; "A Capacitive Touch Interface for Passive RFID Tags"; IEEE International Conference on RFID; Apr. 27-28, 2009; pp. 103-109; IEEE.

Sample et al.; "Design of an RFID-Based Battery-Free Programmable Sensing Platform"; IEEE Transactions on Instrumentation and Measurement; Nov. 2008; pp. 2608-2615; vol. 57, No. 11; IEEE.

Sample et al.; "Photovoltaic Enhanced UHF RFID Tag Antennas for Dual Purpose Energy Harvesting"; 2011 International Conference on RFID; Apr. 12-14, 2011; pp. 146-153; IEEE.

Stevens et al.; "RuBee (IEEE 1902.1)—The Physics Behind, Real-Time, High Security Wireless Asset Visibility Networks in Harsh Environments"; Sep. 2010; retrieved from web Nov. 17, 2011; pp. 1-6; located at: http://www.rubee.com/White-SEC/RuBee-Security-080610.pdf.

Tehrani et al.; "Detection of Monoclonal Antibodies using Chemically Modified Graphite Substrates"; IEEE Sensors 2010 Conference Proceedings; Nov. 1-4, 2010; pp. 428-431; IEEE.

Visible Assets; "RuBee Technology, Real-Time Asset Visibility"; printed from web Nov. 17, 2011; pp. 1-3; located at: http://www.rubee.com/Techno/index.html ;Visible Assets.

Wang, Wencheng; "A Design Method of Ultrasonic Ranging System with High Accuracy"; Journal of Computational Information Systems; Jul. 2011; pp. 2444-2451; vol. 7, No. 7; Binary Information Press.

Yeager et al.; "Wirelessly-Charged UHF Tags for Sensor Data Collection"; 2008 IEEE International Conference on RFID; Apr. 16-17, 2008; pp. 320-327; IEEE.

European Patent Office; Communication pursuant to Article 94(3) EPC; App. No. EP 13 775 331.5; dated Feb. 15, 2017 (received by our Agent on Feb. 15, 2017); pp. 1-4.

European Patent Office; Communication pursuant to Article 94(3) EPC; App. No. EP 13 775 973.4; dated Feb. 14, 2017 (received by our Agent on Feb. 14, 2017); pp. 1-4.

* cited by examiner

APPURTENANCES FOR REPORTING INFORMATION REGARDING WOUND DRESSINGS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of United States Patent Application No. Ser. No. 13/445,220, entitled COMPUTATIONAL METHODS AND SYSTEMS FOR REPORTING INFORMATION REGARDING APPURTENANCES TO WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012, which is currently co-pending or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

In one aspect, an appurtenance to a wound dressing includes, but is not limited to: a substrate configured to mechanically or chemically attach to a wound dressing, a transmission unit attached to a surface of the substrate, the transmission unit including circuitry and at least one antenna, the transmission unit configured to transmit a signal; and a projection operably attached to the transmission unit, the projection of a size and shape to extend into an interior region of the wound dressing.

In one aspect, an appurtenance to a wound dressing includes, but is not limited to: a substrate configured to attach to a wound dressing; a transmission unit attached to a surface of the substrate, the transmission unit including circuitry and at least one antenna operably attached to the circuitry; a selectively actuatable switch operably connected to the transmission unit; a projection operably attached to the substrate, the projection of a size and shape to extend into an interior region of a wound dressing; and one or more sensors integral to the projection and operably connected to the selectively actuatable switch.

In one aspect, an appurtenance to a wound dressing includes, but is not limited to: one or more sensors; a processor operably attached to the one or more sensors; at least one transmitter unit operably attached to the processor; and an enclosure of a height and width to fit substantially within an interior region of a wound dressing.

In one aspect, an appurtenance to a wound dressing includes, but is not limited to: a sensing unit including one or more sensors, the sensors positioned substantially within an enclosure of a height and width to fit substantially within an interior region of a wound dressing; a transmission unit including a processor and at least one transmitter unit operably attached to the processor; and a connector between the sensing unit and the transmission unit, the connector configured to convey signals between the one or more sensors and the transmission unit.

In one aspect, an appurtenance to a wound dressing includes, but is not limited to: a substrate; a passive radio frequency identification (RFID) unit attached to the substrate; and a substantially hollow projection operably attached to the substrate, the projection including a first end and a second end, the first end of a size and shape to extend within a wound dressing, the second end extending into the passive radio frequency identification unit. In addition to the foregoing, other aspects of an appurtenance to a wound dressing are described in the claims, drawings, and text forming a part of the present disclosure.

In one aspect, a device includes, but is not limited to: a wound dressing; a transmission unit irreversibly attached to the wound dressing, the transmission unit including circuitry and at least one antenna; a selectively actuatable switch operably connected to the transmission unit; and a projection operably attached to the switch, the projection extending within an interior region of the wound dressing. In one aspect, an article of manufacture includes, but is not limited to: a wound dressing; a substrate attached to an external surface of the wound dressing; a transmission unit attached to a surface of the substrate, the transmission unit including circuitry and at least one antenna, the transmission unit configured to transmit a signal; a selectively actuatable switch operably connected to the transmission unit; and a projection operably attached to the switch, the projection extending through the external surface of the wound dressing. In addition to the foregoing, other device aspects are described in the claims, drawings, and text forming a part of the present disclosure.

In one aspect, a device for attaching an appurtenance to a wound dressing includes, but is not limited to: a base plate; a handle attached to the base plate; a holder region configured to hold an appurtenance to a wound dressing during attachment to a wound dressing; a handle attached to the holder region; and a pivot between the handle attached to the base plate and the handle attached to the holder region. In addition to the foregoing, other aspects of a device for attaching an appurtenance to a wound dressing are described in the claims, drawings, and text forming a part of the present disclosure.

In one aspect, a method of attaching an appurtenance to a wound dressing includes, but is not limited to: placing an appurtenance for a wound dressing in contact with an outer surface of the wound dressing; and providing pressure on the appurtenance sufficient to force a section of the appurtenance through the outer surface of the wound dressing and into an interior region of the wound dressing. In addition to the foregoing, other method aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
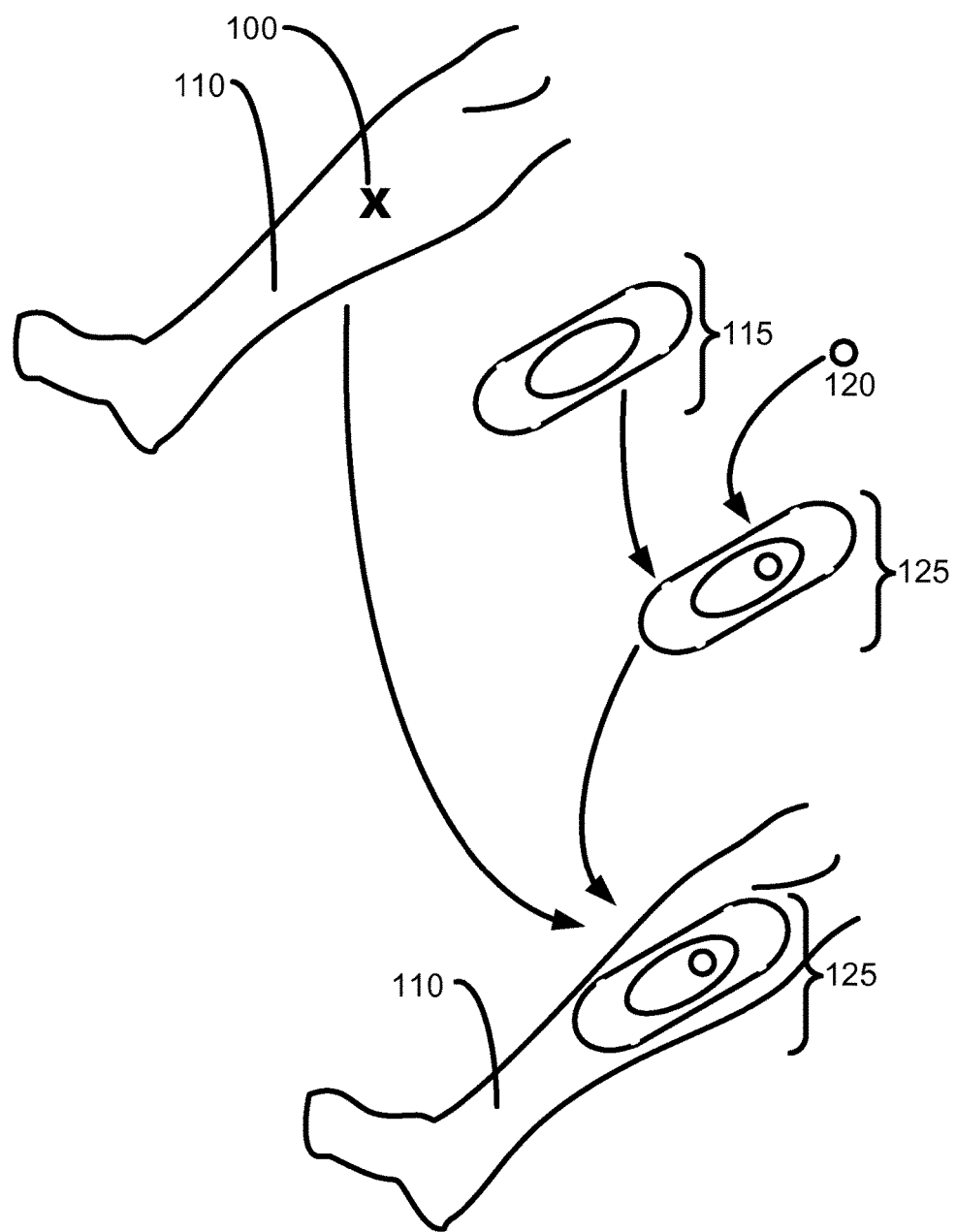
FIG. 1 is a schematic of an appurtenance to a wound dressing in use with a wound.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments can be utilized, and other changes can be made, without departing from the spirit or scope of the subject matter presented here.

The use of the same symbols in different drawings typically indicates similar or identical items.

With reference now to FIG. 1, shown is an example of an appurtenance 120 to a wound dressing 115, used on a wound 100, which can serve as a context for introducing one or more processes and/or devices described herein. As shown in FIG. 1, a body part 110, such as a leg, includes a wound 100. A wound dressing 115, selected by a medical caregiver as appropriate in size, shape and type for the wound 100, has an appurtenance 120 attached to generate an appurtenance affixed to a wound dressing combination unit, 125. The appurtenance 120 can be attached to the wound dressing 115 with a mechanical attachment (see, e.g. FIGS. 11A and 11B). For example, a mechanical attachment can include attachments shaped like prongs, barbs, bristles, spikes, or spurs. The appurtenance 120 can be attached to the wound dressing 115 with a chemical attachment, such as a pressure-sensitive adhesive, a contact adhesive, or a quick-drying adhesive. The appurtenance 120 is a separate and distinct element that can be attached to the wound dressing 115 in a manner sufficient for operation during the use of a specific wound dressing 115. The appurtenance 120 is a separate and distinct element that can be attached to the wound dressing 115 in an irreversible manner. For example, the appurtenance-wound dressing combination unit, 125, can be disposed of after use. Immediate disposal after use can be desirable to minimize biosafety, contamination and biohazard issues. The appurtenance 120 is a separate and distinct element that can be attached to the wound dressing 115 in a reversible manner. For example, the appurtenance-wound dressing combination unit, 125, can be taken apart into its component wound dressing 115 and appurtenance 120 after use. For example, the appurtenance 120 can be configured for reuse with a new wound dressing 115. The appurtenance 120 can be configured for reuse after treatment, such as after disinfection, cleaning, or sterilization. An appurtenance 120 to a wound dressing 115 can be reused, for example, on a succession of wound dressings 115 used by the same patient.

The appurtenance 120 is configured for functional use only when attached to the wound dressing 115. The appurtenance 120 is of a size, shape and material for functional use only when attached to the wound dressing 115. The appurtenance 120 is configured to operate in conjunction with the wound dressing 115. The appurtenance 120 is appended to the wound dressing 115 to generate an appurtenance-wound dressing combination unit 125, as illustrated in the lower right region of FIG. 1. The appurtenance 120 includes at least one region that projects into the structure of the wound dressing 115. In some embodiments, the region that projects into the structure of the wound dressing 115 is of a size and shape to be entirely enclosed within the structure of the wound dressing 115. In some embodiments, the region that projects into the structure of the wound dressing 115 is of a size and shape to project through the wound dressing 115, for example to a region adjacent to a wound. In some embodiments, the region that projects into the structure of the wound dressing 115 is of a size and shape to project through the wound dressing 115, for example to a wound bed region. In some embodiments, the region that projects into the structure of the wound dressing 115 is of a size and shape to project through a portion of the wound dressing 115, for example to a sinus or cavity of the wound bed. In some embodiments, the region that projects into the structure of the wound dressing 115 is of a size and shape to project through a portion of the wound dressing 115, for example to a dressing placed within a sinus or cavity of the wound bed. In some embodiments, the region that projects into the structure of the wound dressing 115 is of a size and shape to project through a portion of the wound dressing 115, for example to a layer placed adjacent to the wound surface. The appurtenance 120 affixed to the wound dressing 115 forms an integrated unit of the appurtenance and the wound dressing as a combination unit 125 (see, e.g. FIGS. 2, 5, and 7-11). In some embodiments, the wound dressing-appurtenance combination unit 125 is not readily separable, and the individual wound dressing 115 and appurtenance 120 are not suitable for separation and individual use after they have been joined together. As illustrated in the lower portion of FIG. 1, once the appurtenance 120 is affixed to the wound dressing 115, the appurtenance and the wound dressing together as a combination unit 125 are used to cover and monitor the wound 100.

In some aspects, an appurtenance 120 to a wound dressing 115 is configured to monitor one or more aspects of a wound 100. An appurtenance 120 to a wound dressing 115 can be used by a caregiver or a patient to monitor a wound 100. In some aspects, an appurtenance 120 to a wound dressing 115 is configured to monitor one or more aspects of a wound dressing 115. An appurtenance 120 to a wound dressing 115 can be used by a caregiver, including a patient, to monitor a wound dressing 115. An appurtenance 120 to a wound dressing 115 is configured to allow a user, such as a caregiver or patient, to monitor a wound dressing and the adjacent wound without disturbing the wound dressing 115 such as through removing the dressing 115 from the patient's wound 100. This approach, inter alia, improves comfort to the patient, reduces the chance of accidental infection in or contamination from uncovered wounds, and minimizes time requirements in wound care. As described further below, in some aspects, an appurtenance 120 to a wound dressing 115 includes a transmitter that sends a signal to a device used by a caregiver or patient to monitor the wound dressing from the same room as the patient. As also described further below, in some aspects, an appurtenance 120 to a wound dressing 115 includes a transmitter that sends a signal to a device used by a caregiver remotely, such as through a pager, remote computing device, cell phone, or dedicated remote signaling device. The signal transmitter sends a signal containing information associated a wound and/or adjacent wound dressing such that a caregiver is able to receive, directly or indirectly, information relating to monitoring a wound and adjacent wound dressing at a distance from the patient, without disturbing the patient and with minimal time spent analyzing the wound 100 or wound dressing 115.

As described further below, in some aspects, an appurtenance 120 to a wound dressing 115 is part of a system configured to automatically process and save information relating to an appurtenance 120 and the related wound dressing 115 to a medical record system, such as a medical records database. This automatic process reduces the potential for accidental loss or error in data entry regarding wound care, and reduces the time required by a caregiver in data entry into a record.

The wound dressing with the affixed appurtenance combination unit 125 is used to cover the wound 100 on the body part 110. The wound dressing with the affixed appurtenance combination unit 125 can be secured to the body part 110 in a routine manner for the type of wound dressing 115 generally, such as through adhesive integral to the wound dressing 115 or with additional adhesive, wrappings, tapes or glues as generally applicable to the type of wound dressing 115 utilized in a given medical situation. Although not illustrated in FIG. 1, the wound dressing with the affixed appurtenance combination unit 125 can similarly be removed using standard removal procedures, such as with gentle pressure, gentle pulling, unwrapping, allowing it to loosen over time, or bio-compatible solvents. The appurtenances 120 described herein can be single-use and disposable along with the affixed wound dressing 115. In some embodiments, the appurtenances 120 described herein can be removed from a first wound dressing and then reconditioned, such as through cleaning or sterilization, and reused with a second wound dressing. In some embodiments, an appurtenance 120 can be reused for multiple wound dressings used on a single wound from a patient. The appurtenances 120 described herein are generally intended to be operable for the period of time a given wound dressing 115 is in use under standard conditions and time periods. After the wound dressing with the irreversibly affixed appurtenance combination unit, 125 is removed from the body part 110, it can be disposed of as a unit with routine disposal methods.

It is envisioned that the appurtenances 120 described herein will be utilized while affixed to wound dressings 115 over wounds 100 of a variety of types, and operable to assist in the monitoring of wounds of a variety of types. For example, appurtenances 120 can be used in conjunction with wound dressings 115 to assist in monitoring acute wounds, such as those resulting from accidental injury or surgery. For example, appurtenances 120 can be used in conjunction with wound dressings 115 to assist in monitoring wounds closed by primary intention. For example, the appurtenances 120 can be used to assist in monitoring wound dressings over surgical wounds, such as incisions and surgical stitches. For example, the appurtenances 120 can be used to assist in monitoring wound dressings over acute wounds from injury, such as burn injuries, lacerations, or penetrating wounds. For example, appurtenances 120 can be used in conjunction with wound dressings 115 to assist in monitoring wounds closed by secondary intention. The appurtenances 120 can also be used to assist in monitoring wound dressings over chronic wounds, such as those arising from chronic medical conditions and situations. For example, the appurtenances 120 can be used to monitor the status of wound dressings covering venous leg ulcers, diabetic foot ulcers, pressure ulcers or arterial ulcers. See: "Advances in Wound Healing Techniques," publication D11A, Frost and Sullivan, 2008; "An Overview of Ulceration Wounds," Publication M4BB-54, Frost and Sullivan 2009; and "US Advanced Wound Care Market," Publication N71A-54, Frost and Sullivan 2010, which are each incorporated herein by reference.

The appurtenances 120 described herein can be useful in conjunction with an affixed wound dressing as a combination unit 125 to monitor potential problems with a wound, such as excessive bleeding or other fluid formation that would be present in the wound dressing, or the presence of conditions in the dressing that indicate infection in an adjacent wound. See: Collier, "Recognition and Management of Wound Infections," *World Wide Wounds*, pages 1-9, (January 2004); and Gray, "Assessment, Diagnosis and Treatment of Infection," Wounds UK, vol. 7, no. 2, supplement, (2011), which are each incorporated herein by reference. For example, some types of wound discharge can indicate infection. See, for example, Cutting and Harding, "Criteria for Identifying Wound Infection," *Journal of Wound Care*, vol. 3, no. 4, 198-201 (1994), which is incorporated herein by reference. The appurtenances 120 as part of combination units 125 and related systems described herein can be used in conjunction with readily available types of wound dressings to monitor aspects of the affixed wound dressing, including parameters that indicate that a person should physically examine the wound dressing, such as excessive wetness, dryness, an elapsed period of time, or the presence of specific factors detected by one or more sensors of the appurtenance. The appurtenances 120 as well as related systems described herein can be used in conjunction with readily available types of wound dressings to monitor aspects of the affixed wound dressing, including indications that the wound dressing should be changed (i.e. excessively wet, dry, or soiled).

The appurtenances described herein include transmission units configured to transmit signals, and thereby report information regarding the status of the affixed wound dressing or wound, to associated systems. The resulting information reporting can be used, in some embodiments, to supplement the medical record for a patient in an automated system and automatic process. The resulting information reporting can be used, in some embodiments, to automatically notify a caregiver that the status of the wound dressing has altered, indicating that a person should physically inspect the wound dressing.

As used herein, a caregiver includes at least one of a patient, a caregiver, and medical personnel. A caregiver can utilize some embodiments of the appurtenances and related systems described herein in relation with multiple types of wound dressings. Appurtenances can be fabricated in shapes and sizes to conform to a variety of standard wound dressing sizes, shapes and types. Appurtenances can be fabricated with, for example, transmission units, antennas and sensors appropriate for use with a variety of wound dressings. Appurtenances can be fabricated with, for example, transmission units, antennas and sensors appropriate for different medical situations and monitoring requirements. Appurtenances can be fabricated with, for example, one or more projections of a size, shape and material appropriate for use with a variety of wound dressings. While it is envisioned that every appurtenance will not be appropriate for use with every wound dressing (for example due to size, shape or material compatibility), a given appurtenance is expected to be suitable for use with a range of potential wound dressings. For example, a given appurtenance of a specific size, shape and fabrication, including type of transmission unit, sensors, and projection(s), should be suitable for use with a variety of wound dressings of conforming sizes, shapes and types. Generally, any specific appurtenance embodiment is not expected to only conform to use with a unique wound dressing of a specific size, shape and type. Instead, it is expected that a specific appurtenance embodiment will be suitable for use with a range of wound dressings. Similarly, it is expected that a specific appurtenance embodiment will be suitable for use with a range of wound and wound dressing monitoring requirements.

In the attached drawings, an appurtenance 120 is generally illustrated as affixed to an outer surface of a wound dressing 115, for example an outer surface distal to a surface of the body part 110 adjacent to the wound 100. However, in some embodiments, an appurtenance 120 can be configured to attach to one or more surfaces of a wound dressing 115 adjacent to a surface of the body part 110 adjacent to the wound 100. For example, in embodiments wherein an appurtenance 120 is configured to be attached to a wound dressing 115 of a substantially rectangular, ovoid, or raised conformation, an appurtenance 120 can be configured to be attached to a side surface of the wound dressing 115. For example, in embodiments wherein an appurtenance 120 is configured to be attached to a wound dressing 115 with an unusually strong or thick outer cover layer, the appurtenance 120 can be configured to attach to an underside of the wound dressing 115. In some embodiments, an appurtenance is configured to attach to a surface of a wound dressing 115 in contact with the surface of the body part 110.

For example, the appurtenances described herein can be configured to be affixed to a dry gauze dressing, which can or can not include an outer cover layer. For example, the appurtenances described herein can be configured to be attached to a dry silicone or other solid foam dressing, which can or can not include an outer cover layer. For example, the appurtenances described herein can be configured to be affixed to a wound dressing used to close a small or thin wound or surgical incision, such as a butterfly dressing (e.g. SteriStrip™ adhesive strips, available from Nexcare™, part of 3M Corporation). For example, appurtenances such as those described herein can be configured to be affixed to a dressing configured to maintain moisture or other materials adjacent to the wound surface. For example, appurtenances such as those described herein can be configured to be used with hydrogel wound dressings, for example Aquaflo™ Hydrogel Wound Dressing by Kendall Corporation, or Elasto-Gel™ Hydrogel Occlusive Dressing by Southwest Technologies. For example, appurtenances such as those described herein can be affixed to wound dressings including hydrocolloids, for example DuoDERM CGF Sterile Hydrocolloid Dressing manufactured by DuoDERM Corporation. For example, appurtenances such as those described herein can be configured to be used with wound dressings containing one or more medicinal agents, such as antibiotics. For example, appurtenances such as those described herein can be used with wound dressings impregnated with PHMB (Polyhexamethylene Biguanide), such as Telfa™ A.M.D. antimicrobial wound dressings, manufactured by Kendall Corporation. For example, appurtenances such as those described herein can be configured to be used with wound dressings including ionic silver, such as Maxorb™ Extra Ag wound dressings manufactured by Medline Corporation. Appurtenances such as those described herein can be configured to be affixed to wound dressings over wounds wherein the tissue of the wound is being directly monitored using other devices, for example as described in U.S. Pat. No. 6,963,772 to Bloom et al., titled "User-retainable Temperature and Impedance Monitoring Methods and Devices,"

which is incorporated herein by reference. Appurtenances such as those described herein can be configured to be affixed to wound dressings over wounds wherein the patient is being directly monitored using other devices, for example as described in U.S. Pat. No. 7,030,764 to Smith and Cooper, titled "Apparatus and Method for Reducing the Risk of Decubitus Ulcers;" U.S. Pat. No. 7,297,112 to Zhou et al., titled "Embedded Bio-Sensor System;" U.S. Pat. Nos. 7,372,780, 8,014,234 and 7,813,226 to Braunberger, titled "Timing System and Device and Method for Making the Same;"U.S. Pat. No. 7,666,151 to Sullivan et al., titled "Devices and Methods for Passive Patient Monitoring;" U.S. Pat. No. 7,703,334 to Cochran, titled "Bandage Type Sensor Arrangement and Carrier Assembly Therefore, and Method of Manufacture;" and International Patent Publication No. WO 2005/009328 to Nikolic, titled "ABT—Anti-Bedsore Timer," which are each incorporated herein by reference. Appurtenances such as those described herein can also be used in conjunction with a system to monitor assets within a health care facility, for example as described in US Patent Application No. 2007/0247316 to Wildman et al., titled "Article Locating and Tracking Apparatus and Method," which is incorporated herein by reference.

Wound dressings 115 such as those described herein are generally used for a relatively short period of time, on the order of hours or days, and then removed for disposal. Similarly, a wound dressing with an affixed appurtenance combination unit 125 should be configured for use over the course of hours or days and then removed and disposed of using standard methods. A wound dressing with an affixed appurtenance is single use and disposable after use. For example, a caregiver can require a new wound dressing every 24 hours (1 day) for an acute wound. Any wound dressing utilized in this type of situation would, consequently, be of a size and shape to remain affixed to the wound region over the course of at least a 24 hour period and then removed for disposal. An appurtenance to a wound dressing intended for use over the course of a 24 hour time period, similarly should be of a size, shape, material fabrication, and capabilities to function while affixed to the wound dressing over the 24 hour period that the dressing is in use. As an additional example, a caregiver can decide that for another type of wound, such as a chronic wound, the wound dressing needs to be removed and replaced once every 3 days, or every 4 days, or every 5 days, or every 6 days, or every 7 days. Correspondingly, an appurtenance affixed to a wound dressing intended for use over the course of at least 3 to 7 days should be of a size, shape, material fabrication, and capabilities to function while affixed to the wound dressing over at least the 3 to 7 day period that the dressing is in use. In embodiments wherein an appurtenance is intended for reuse, such as reuse on a second or subsequent wound dressing used over a wound, the appurtenance should be of a size, shape, material fabrication and capabilities to function during the entire intended use, including the time period of removal from a first wound dressing and application to a second wound dressing.

Figure 2A:
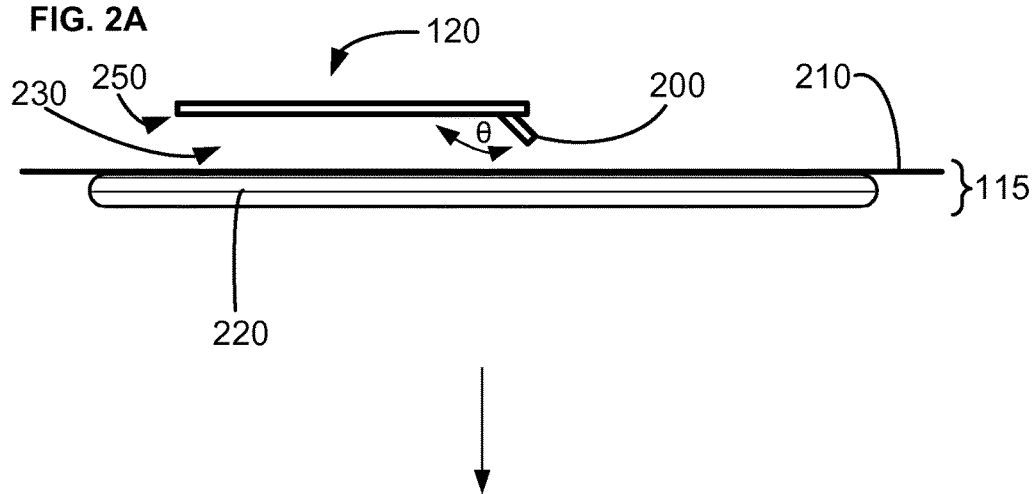
FIG. 2A is a schematic of an appurtenance to a wound dressing prior to attachment to a wound dressing.
Figure 2B:
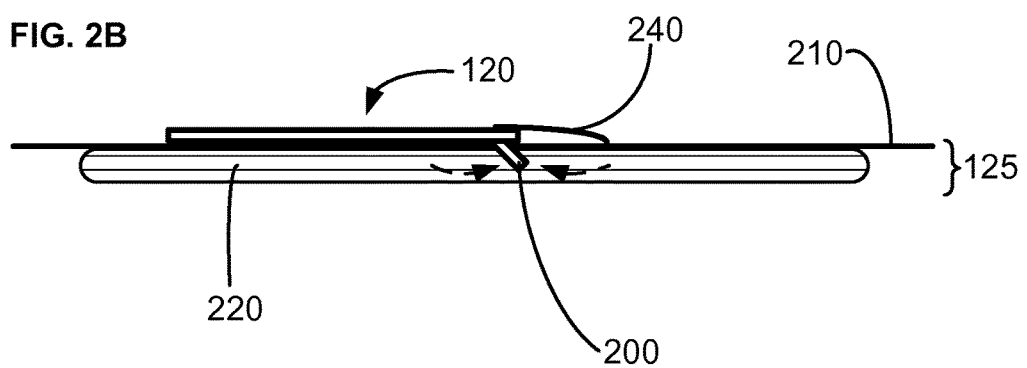
FIG. 2B is a schematic of an appurtenance to a wound dressing after attachment to a wound dressing.

FIGS. 2A and 2B depict further aspects of some embodiments of appurtenances to wound dressings. FIGS. 2A and 2B depict cross-section views of an appurtenance 120 to a wound dressing 115. As illustrated in FIG. 2A, the appurtenance 120 includes a substantially planar section and a projection 200. The substantially planar section includes a surface 230 configured to substantially conform with an outer surface of the wound dressing 115. In some embodiments, the surface 230 of the appurtenance 120 configured to conform with an outer surface of the wound dressing 115 can include adhesive of a type expected to irreversibly adhere to the surface of the wound dressing 115. In some embodiments, the surface 230 of the appurtenance 120 configured to conform with an outer surface of the wound dressing 115 can include adhesive of a type expected to adhere to the surface of the wound dressing 115 for a period of time, and to be removable. In some embodiments, the surface 230 of the appurtenance 120 configured to conform with an outer surface of the wound dressing 115 can include barbs, hooks, pins, prongs or other extensions configured to adhere or fix onto the outer surface of the wound dressing 115 (see, e.g. FIGS. 11A and 11B). For example, an appurtenance 120 configured to conform with an outer surface of the wound dressing 115 can include barbs, hooks, pins, prongs or other extensions that irreversibly adhere to the outer surface of the wound dressing 115, such as by imbedding into the outer surface. For example, an appurtenance 120 configured to conform with an outer surface of the wound dressing 115 can include barbs, hooks, pins, prongs or other extensions that reversibly adhere to the outer surface of the wound dressing 115, such as by reversibly interacting with extensions projecting from the outer surface.

Figure 9A:
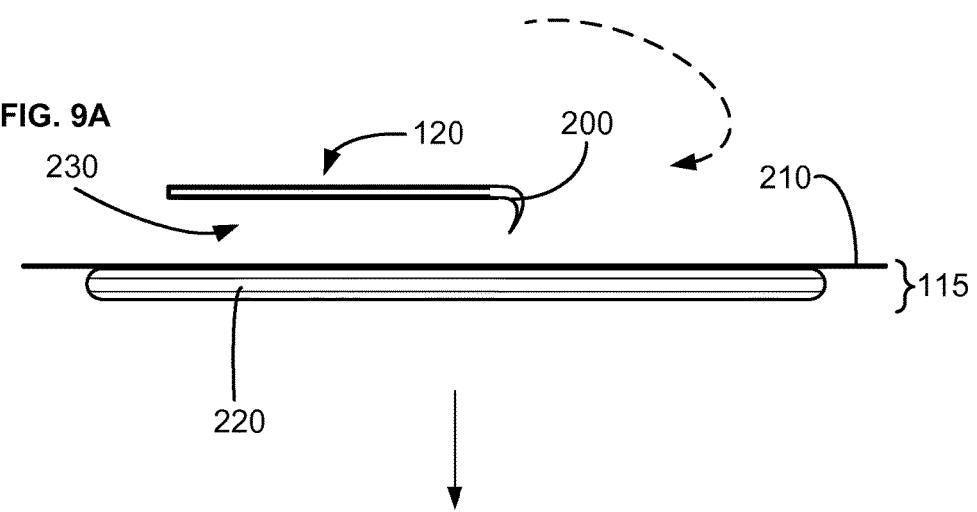
FIG. 9A is a schematic of an appurtenance to a wound dressing prior to attachment to a wound dressing.
Figure 9B:
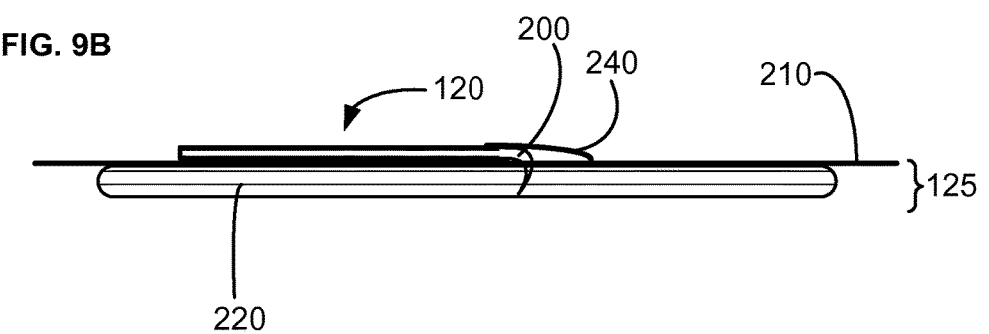
FIG. 9B is a schematic of an appurtenance to a wound dressing after attachment to a wound dressing.

The appurtenance 120 depicted in FIGS. 2A and 2B includes a projection 200. As shown in FIGS. 2A and 2B, the projection extends from a surface 230 of the appurtenance 120 configured to conform with an outer surface of the wound dressing 115. The single projection depicted in FIGS. 2A and 2B projects at an angle from the plane formed by the substantially planar section of the appurtenance 120 conforming to the surface of the wound dressing 115. This angle is depicted in FIG. 2A as $\theta$. In FIGS. 2A and 2B, for example, the angle shown as $\theta$ is approximately 135 degrees. However, as will be more evident from further description below (see, e.g. in relation to FIGS. 10A, 10B, 11A and 11B), in some embodiments an appurtenance 120 can include a plurality of projections 200. Depending on the embodiment, the projections 200 can also be at a variety of angles relative to the section of the appurtenance 120 conforming to the surface of the wound dressing 115. For example, in some embodiments, one or more projections can be at angles less than approximately 135 degrees, between approximately 135 degrees and approximately 90 degrees, or substantially at approximately 90 degree angles relative to a planar section of the appurtenance 120. In some embodiments, an appurtenance 120 includes a substantially planar region including a transmission unit, wherein the substantially planar region is configured to conform with an outer surface of the wound dressing 115, and one or more projections 200 projecting substantially perpendicular to the surface 230 configured to conform with an outer surface of the wound dressing 115. Depending on the embodiment, the projections 200 can project in a direction substantially away from the surface of the appurtenance configured to conform with an outer surface of the wound dressing 115 (e.g. as in FIGS. 2A and 2B), or angle in a direction substantially perpendicular to the surface 230 configured to conform with an outer surface of the wound dressing 115 of the appurtenance (e.g. as shown in FIGS. 9A and 9B). Some embodiments include at least one projection 200 which is curvilinear. Some embodiments include at least one projection 200 which is a composite shape. In embodiments including one or more projections that are not substantially straight, an angle (e.g. $\theta$ as illustrated in FIG. 2A) of the projection 200 can be determined by the angle formed at the base of the projection immediately adjacent to the surface of the appurtenance configured to conform with an outer surface of the wound dressing 115.

The projection 200 can be a substantially hollow tubular structure. Although not illustrated in FIGS. 2A and 2B in this view, a substantially hollow tubular structure of the projection 200 includes an opening on the distal end of the projection 200. While the projection 200 depicted in FIGS. 2A and 2B can be a substantially tubular structure, in some embodiments projections can be of different shapes and conformations. For example, a projection 200 can be solid, tubular, conical, cylindrical, tapered, curved, angular or other shape or combination of shapes as appropriate to the specific embodiment. Embodiments including a plurality of projections can include projections of different sizes and shapes. A projection 120 can be substantially straight and form a substantially linear internal channel (e.g. as depicted in FIGS. 2A, 2B, 8A and 8B), or it can be curved and form a substantially curvilinear internal channel (e.g. as depicted in FIGS. 9A and 9B). The drawings illustrated herein are not to scale. The drawings illustrated herein represent relationships and shapes of the items described. Although not expressly illustrated herein, a projection 200 can be relatively large relative to the total size of the appurtenance. For example, the volume of a projection or a group of projections attached to an appurtenance can be 51%, 55%, 60%, 65%, 70%, 75%, 80%, 85%, 90%, 95% or 100% of the volume of the portion of the appurtenance configured to conform with an outer surface of a wound dressing (e.g. the substantially planar region as illustrated in FIGS. 2A and 2B). Similarly, a projection 200 can be relatively small relative to the total size of the appurtenance. For example, the volume of a projection or a group of projections attached to an appurtenance can be 49%, 45%, 40%, 35%, 30%, 25%, 20%, 15%, 10%, or 5% of the volume of the portion of the appurtenance configured to conform with an outer surface of a wound dressing (e.g. the substantially planar region as illustrated in FIGS. 2A and 2B). In some embodiments, a projection 200 is located at an edge region of the substantially planar region of the appurtenance 120, and in some embodiments a projection 200 is located substantially centrally to the planar surface 230 of the appurtenance 120 configured to conform with an outer surface of the wound dressing 115. In some embodiments, a substantially planar appurtenance 120 includes at least one projection 200 wherein the entire appurtenance 120 is of a size and shape to be secured against an external surface of a wound dressing 115 with force, for example from a human thumb or finger.

In some embodiments, an appurtenance 120 can be fabricated with one or more regions configured for the attachment of different modules. In some embodiments, an appurtenance 120 includes modules that are configured for removal and replacement. During fabrication, a basic appurtenance structure can be utilized and different specific modules added as desired in a particular embodiment. For example, an appurtenance 120 can be fabricated with at least one region configured to attach a projection. For example a region configured to attach a projection can include a region with a surface conforming to an outer surface of the projection. For example a region configured to attach a projection can include a conduit configured to align with the hollow interior of the projection. The region of the appurtenance 120 configured to attach a projection can be configured for attachment of different projection types, depending on the embodiment. For example, the region of the appurtenance 120 configured to attach a projection can be configured for attachment of projections of different lengths or different materials as desired in the construction of a particular embodiment. In some embodiments, an appurtenance 120 can have multiple regions configured for attachment of multiple projections of different types. In some embodiments, an appurtenance 120 can have one or more removable antenna modules. For example, an appurtenance 120 can have one or more removable power source modules, such as batteries or solar cells. In some embodiments, a module can include a spacer element, or a component configured to assist in physically positioning one or more other modules.

An appurtenance 120 can be fabricated from a variety of materials, as appropriate to an embodiment. An appurtenance 120 can be fabricated, for example, substantially from a plastic material. For example, a structural portion, such as a shell or base can be fabricated from a plastic material. For example, one or more projections can be fabricated from a plastic material. An appurtenance 120 can be fabricated, for example, from one or more acrylics, polyesters, silicones, polyurethanes and halogenated plastics. An appurtenance 120 can include one or more projections 200 fabricated, for example, from one or more plastic materials. An appurtenance 120 can include one or more projections 200 fabricated, for example, from one or more acrylics, polyesters, silicones, polyurethanes and halogenated plastics. An appurtenance 120 can be fabricated from one or more biocompatible materials, for example bio-compatible plastics, resins, epoxies and metals. An appurtenance 120 can be fabricated from one or more composite materials, such as plastic with an overlay of epoxy or plastic with an overlay of one or more metals. An appurtenance 120 including a transmission unit can include, for example, one or more metal components, for example as circuitry or as one or more antennas. An appurtenance 120 including a transmission unit can include, for example, stainless steel, copper or zinc alloy. An appurtenance 120 can be fabricated from one or more ceramic materials, such as within a transmission unit. Generally, it is envisioned that materials with low weight will be suitable for a variety of appurtenance embodiments, so as to reduce weight and associated physical stress on a wound dressing. Similarly, it is envisioned that materials with sufficient strength and toughness to be fabricated into small and thin components will be desirable for fabrication of appurtenance embodiments. As the appurtenances are to be permanently affixed to the wound dressings and disposed of with the wound dressings, materials that do not require special handling or disposal are preferable in most embodiments.

In some embodiments, the appurtenance 120 includes a substrate, (e.g. 250) that is configured to attach to the wound dressing 115. For example, the substrate can be configured as a support for other features of the appurtenance 120. In some embodiments, the substrate includes a substantially planar structure wherein the area of surface 230 is less than the area of the wound dressing 115 (see, e.g. FIGS. 12-17). In some embodiments, the substrate is configured to irreversibly attach directly to an external surface of the wound dressing 115. In some embodiments, the substrate includes an adhesive on a surface conforming to an external surface of the wound dressing 115 (e.g. surface 230 in FIG. 2A). For example, the surface conforming to an external surface of the wound dressing 115 can include a glue, epoxy, sealant, mucilage, paste or other binder material. In some embodiments, the surface of the substrate conforming to an external surface of the wound dressing 115 can include an adhesive covered by a removable protective sheet configured for detachment and exposure of the adhesive when the appurtenance 120 is attached to the wound dressing 115. In some embodiments, the surface 230 of the substrate of the appurtenance 120 configured to conform with an outer surface of the wound dressing 115 can include barbs, hooks, pins, prongs or other extensions configured to adhere or fix into the outer surface of the wound dressing 115 (see, e.g. FIGS. 11A and 11B). In some embodiments, the surface 230 of the substrate of the appurtenance 120 configured to conform with an outer surface of the wound dressing 115 can include a mixture or combination of any of the above.

In some embodiments, the substrate includes a flexible material. For example, the substrate can include a pliable plastic, a woven fabric material, soft mesh or other flexible material. In some embodiments, the substrate includes a rigid material. For example, the substrate can include at least one rigid plastic material in a location configured to provide support for a portion of the appurtenance. For example, the substrate can include at least one rigid plastic material at a location configured to attach a projection, the rigid plastic configured to provide physical support for the attached projection. In some embodiments, the substrate includes at least one bio-compatible material. For example, the substrate can include one or more bio-compatible plastic materials, one or more bio-compatible fabric materials, or one or more bio-compatible metals.

FIG. 2A depicts a cross section view of an appurtenance 120 adjacent to a wound dressing 115. As shown in FIG. 2A, the wound dressing 115 includes a dressing layer 220 and an outer layer 210. Not all wound dressings 115 should be expected to include multiple layers, and it is to be expected that some wound dressings 115 substantially include only a wound dressing material and not additional layers, structures or coverings. However, as illustrated in FIGS. 2A and 2B, in some embodiments wound dressings 115 include a plurality of layers. For example, a wound dressing 115 can include one or more outer layers 210 configured to protect and isolate the wound dressing layer(s) from microbes, external dirt and debris, dryness, wetness or other external factors. An outer layer can be fabricated from materials such as firm plastics or mesh materials. An outer layer can include a surface larger than the surface of the wound dressing layer, and can include adhesives on that surface configured to adhere the entire wound dressing to a body surface. A wound dressing 115 can include one or more layers of wound dressing 220 materials, such as gauze, films, foams, or sponges. A wound dressing 115 can include one or more layers of hydrogels, colloid gels, and medicinal agents impregnated within one or more layers of the wound dressing 220 or on a surface of the wound dressing 220 configured to face a wound.

A surface 230 of an appurtenance 120 can be configured to conform to the surface of the outer layer 210 of a wound dressing 115. For example, the surface can be of a size and shape that substantially conforms with the surface of the wound dressing 115. A surface 230 of an appurtenance 120 can include barbs, hooks, pins, prongs or other extensions configured to reversibly or irreversibly stick into the outer surface of the wound dressing 115 (see, e.g. FIGS. 11A and 11B). A surface 230 of an appurtenance 120 can include one or more adhesives of a type to attach the appurtenance 120 to the wound dressing 115.

FIG. 2B illustrates the appurtenance 120 and the wound dressing 115 of FIG. 2A after the appurtenance 120 is affixed to the wound dressing 125. As illustrated in FIG. 2B, a projection 200 of an appurtenance 120 can be configured to pierce through the outer layer 210 and into a wound dressing layer 220. A projection 200 of an appurtenance 120 can be of a size and shape to project from the outer surface of the wound dressing 115 to within layers of the wound dressing 115. A projection 200 can be of a size and shape to extend into an interior region of the wound dressing 115. A projection 200 can be of a size and shape to project within an interior region of the wound dressing 115. As shown in FIG. 2B, a projection 200 can be of a size and shape to project underneath one or more superficial structures of the wound dressing 115 (such as an outer layer 210) when the wound dressing 115 is in use. A projection 100 can be of a size and shape to project through a width of the wound dressing 115 when the appurtenance 120 is attached to the wound dressing 125 (see, e.g. FIG. 8B). Also as illustrated in FIG. 2B, a projection 200 extending within the layers of the wound dressing 125 can be positioned so that fluids, (depicted as dotted arrows) can enter a hollow within the projection 200 through capillary action.

FIG. 2B also illustrates that in some embodiments a cover 240 is attached to the surface of the appurtenance 120 as well as to the surface of the wound dressing, such as to an outer layer of the wound dressing 210. An appurtenance 120 can include a substantially planar cover, the cover including an adhesive on a surface conforming to a surface of a wound dressing, the substantially planar cover configured to cover a location where the projection extends into the wound dressing. A cover 240 can be fabricated, for example, from a flexible plastic or mesh material. A cover 240 can be fabricated, for example, from an inflexible plastic or mesh material and configured in a size and shape to conform with the surfaces of the appurtenance 120 as well as to the surface of the wound dressing 115. A cover 240 can include adhesive on a surface facing the appurtenance and the wound dressing, the adhesive configured to attach the cover to the appurtenance and to the wound dressing. A cover 240 can be configured to stabilize the position of the appurtenance 120 relative to the wound dressing 115 when the appurtenance is affixed to the wound dressing 125 (e.g. as in FIG. 2B). A cover 240 can be configured to secure the appurtenance 120 relative to the wound dressing 115 when the appurtenance is affixed to the wound dressing 125 (e.g. as in FIG. 2B). A cover 240 can be configured to seal the juncture between the appurtenance 120 and the wound dressing 115, for example from dirt, debris, wetness or microbes that can enter the interior of the wound dressing if the juncture is not sealed. A cover 240 can be configured to seal an potential gaps between the projection 200 of the appurtenance 120 and the wound dressing 115, for example to seal any potential gaps from dirt, debris, external wetness or microbes that can enter the interior of the wound dressing if the gap is not sealed.

In some embodiments, an appurtenance 120 to a wound dressing 115 is substantially sterilized prior to use. For example, the appurtenance 120 can be treated with one or more chemical disinfectants or UV surface radiation for a period of time sufficient to substantially sterilize the appurtenance 120 prior to use. For example, the appurtenance 120 can be treated with one or more antimicrobial gasses, for example ethylene oxide (ETO), prior to use. For example, the appurtenance 120 can be treated with a chemical sterilizing agent, such as hydrogen peroxide in liquid or vapor form, prior to use. For example, the appurtenance 120 can be treated with steam as an anti-infective prior to use. In some embodiments, an appurtenance 120 to a wound dressing 115 includes a sterile wrapper. For example, an appurtenance 120 to a wound dressing 115 can be stored and/or transported within a sterile wrapper, such as a firm paper wrapper or a plastic film. A sterile wrapper configured for storage and/or transport of an appurtenance can be treated to minimize contamination, for example coated with one or more anti-microbial agents.

Figure 3:
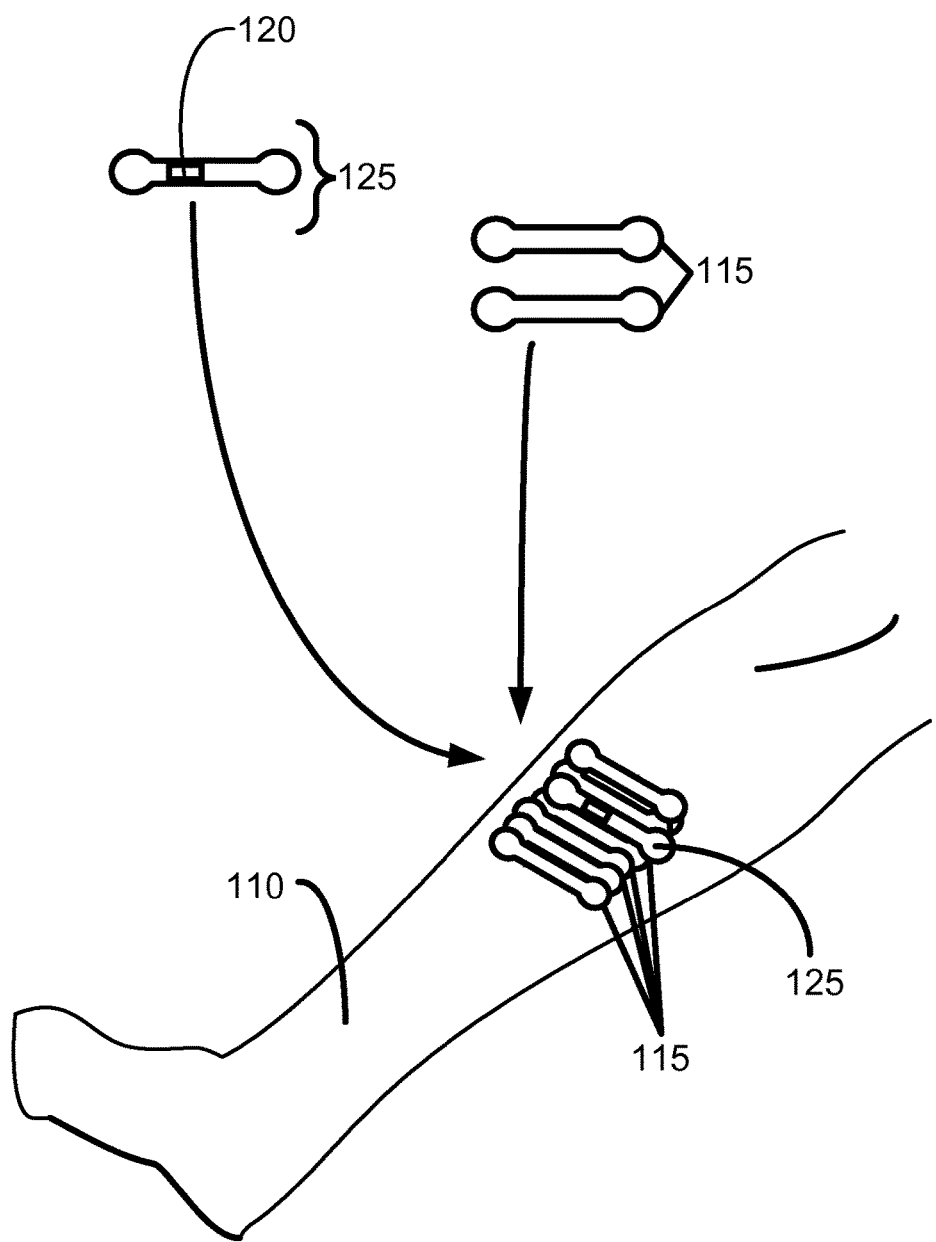
FIG. 3 is a schematic of an appurtenance to a wound dressing in use with a wound.

FIG. 3 illustrates additional aspects of some embodiments of appurtenances to wound dressings. In some situations, a medical caregiver can choose a wound dressing that is not a single unit, but a group of distinct units that together in situ on a body part form a complete, composite wound dressing. For example, a caregiver can choose a composite wound dressing made up from a group of butterfly dressings (e.g. SteriStrip™). As illustrated in FIG. 3, a composite wound dressing can include a plurality of wound dressings 115 as well as at least one wound dressing 125 with an affixed appurtenance 120. When the composite wound dressing is placed in position on a body part 110, such as a leg, the wound dressing 125 with an affixed appurtenance 120 can be included with the grouping of wound dressings 115.

Figure 4:
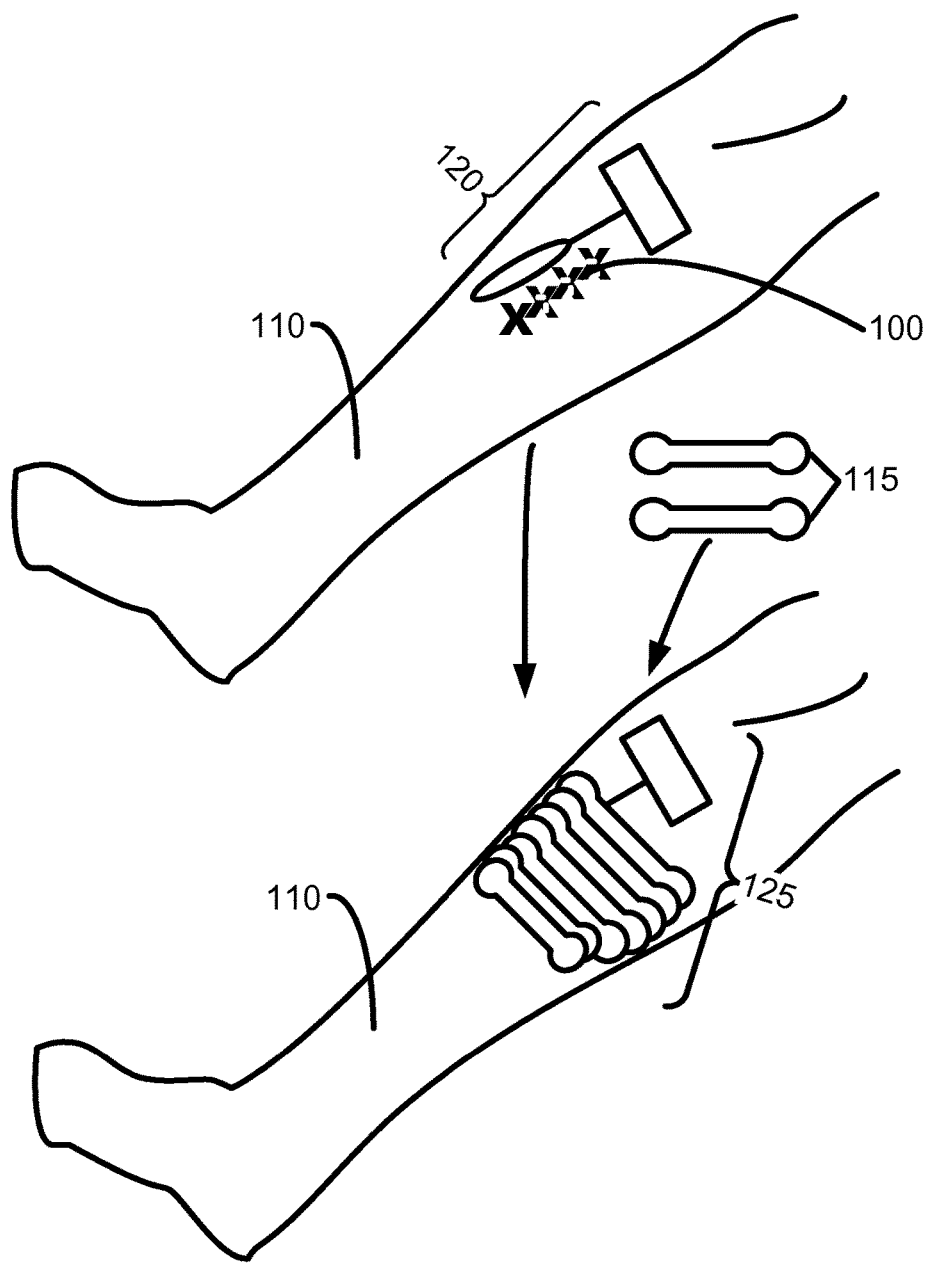
FIG. 4 is a schematic of an appurtenance to a wound dressing in use with a wound.

FIG. 4 illustrates additional aspects of some embodiments of appurtenances to wound dressings similar to that depicted in FIG. 3. In some situations, a caregiver can choose a wound dressing that is not a single unit, but a group of distinct units that together in situ on a body part form a complete, composite wound dressing. For example, a caregiver can choose a composite wound dressing made up from a group of butterfly dressings (e.g. SteriStrip™ adhesive strips). In some embodiments, a caregiver can choose a compression bandaging system as part of a wound dressing. For example, a caregiver can choose a multi-layer compression bandaging system such as the Profore™ System or the Proguide™ System, both manufactured by Smith & Nephew. In some embodiments, a caregiver can choose a negative pressure wound therapy system, such as the Renasys™ system or the Pico™ system, both manufactured by Smith & Nephew, or the V.A.C.™ system manufactured by Kinetic Concepts, Inc. (KCI). As illustrated in FIG. 4, an appurtenance 120 can be positioned on a body part 110, such as a leg, in a region adjacent to a wound 100. A series of wound dressings 115 can be positioned around and over at least a portion of the appurtenance 120 and affixed to the appurtenance 120 to form a composite wound dressing with an affixed appurtenance unit 125. For example, the appurtenance 120 can be interleaved with the individual units of wound dressings 115 and affixed to one or more of the wound dressings 115 to form a composite wound dressing with an affixed appurtenance unit 125. An appurtenance 120 extending within the layers of the wound dressing 125 can be positioned so that fluids can enter an opening in the appurtenance 120 through capillary action.

Figure 5A:
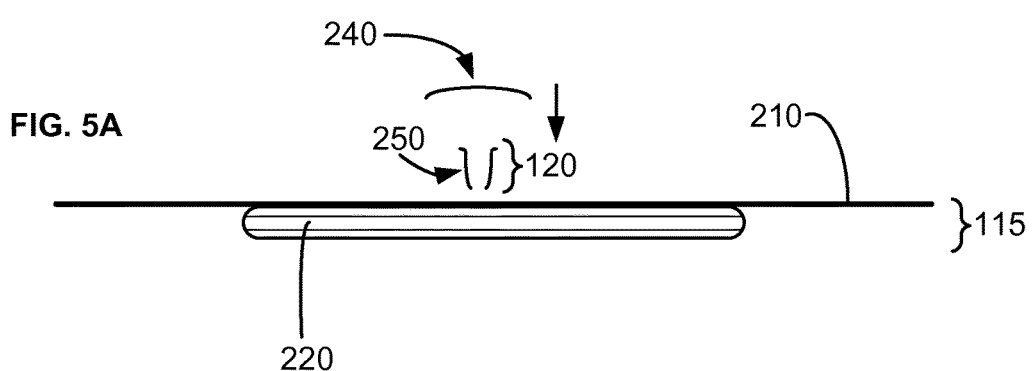
FIG. 5A is a schematic of an appurtenance to a wound dressing prior to attachment to a wound dressing.
Figure 5B:
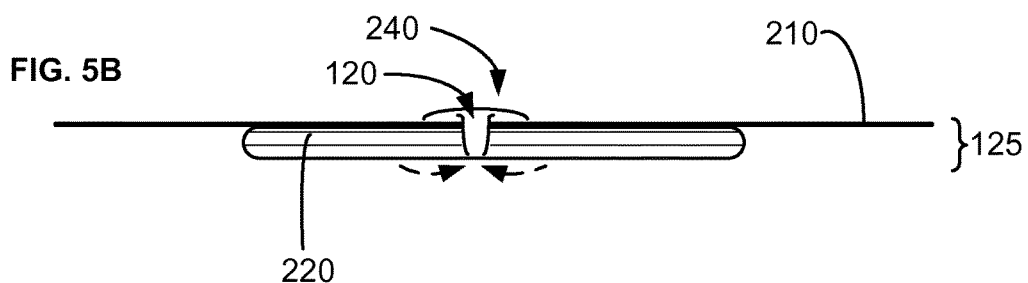
FIG. 5B is a schematic of an appurtenance to a wound dressing after attachment to a wound dressing.

FIGS. 5A and 5B illustrate aspects of some embodiments of an appurtenance 120 to a wound dressing 115 in a cross-sectional view. In some embodiments, an appurtenance 120 includes an enclosure of a height and width to fit substantially within an interior region of a wound dressing 115. FIG. 5A depicts an appurtenance 120 of a size and shape to substantially penetrate an outer cover 210 and into a dressing region 220 of a wound dressing 115. The appurtenance 120 depicted in FIGS. 5A and 5B is a cross section view of a substantially conical shape with an opening at the lower region of the cone (downward in FIGS. 5A and 5B). The main structure of the appurtenance is depicted as 250. As illustrated in FIG. 5A and FIG. 5B, some embodiments include a cover 240. A cover 240 can be of a size and shape to seal the surface of the appurtenance 120 exposed at the surface of the wound dressing. FIG. 5B depicts the appurtenance 120 affixed to the wound dressing 125. The appurtenance 120 depicted in FIG. 5B projects through the outer layer 210 of the wound dressing and into the interior wound dressing layer 220. Also as illustrated in FIG. 5B, an appurtenance 120 extending within the layers of the wound dressing 125 can be positioned so that fluids, depicted as dotted arrows, can enter an opening in the appurtenance 120 through capillary action.

Figure 6:
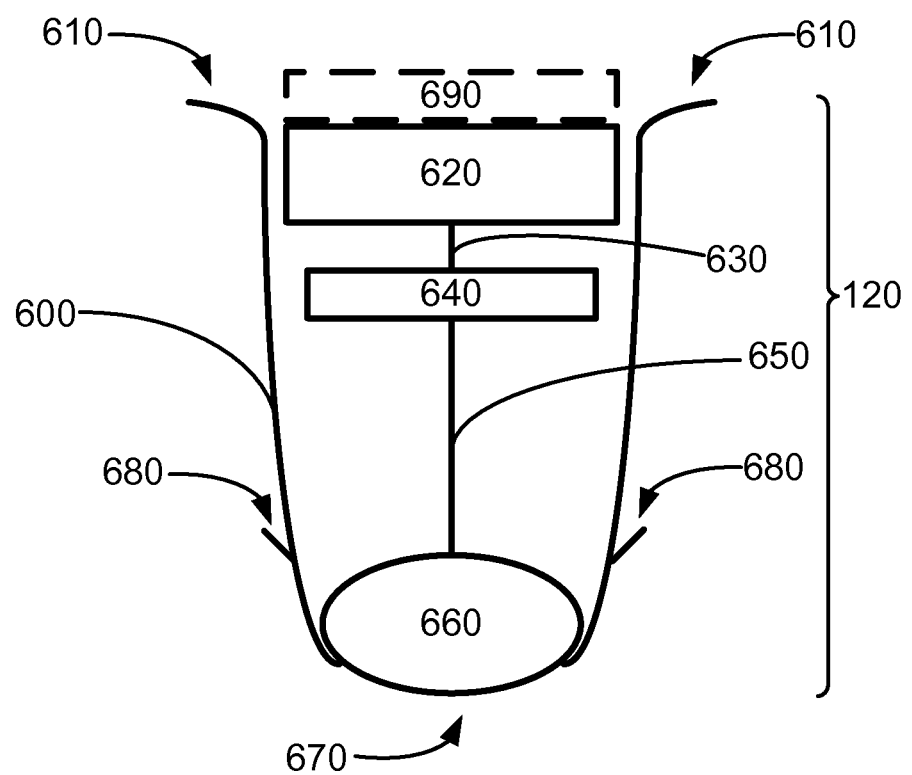
FIG. 6 is a schematic of an appurtenance to a wound dressing.

FIG. 6 illustrates aspects of an embodiment of an appurtenance 120, such as that depicted in FIGS. 5A and 5B. The appurtenance 120 depicted in a cross-sectional view in FIG. 6 includes one or more sensors 660, a processor 640 operably attached to the one or more sensors 660, at least one transmitter unit 620 operably attached to the processor 640, and an enclosure 600 of a height and width to fit substantially within an interior region of a wound dressing (see, e.g. FIG. 5B). The enclosure 600 depicted in FIG. 6 is a cross sectional view of a substantially cone shaped enclosure 600. As shown in FIGS. 5A, 5B and 6, in some embodiments the enclosure is a substantially cylindrical structure, wherein the largest width of the substantially cylindrical structure is less than the smallest width of the wound dressing. In some embodiments, the enclosure 600 includes a substantially conical or a substantially conical frustum shaped structure. In some embodiments, the enclosure 600 includes a cross-sectional view square area that is substantially equal to or less than one tenth of a square area of a largest surface of the wound dressing. As shown in FIG. 6, the enclosure 600 includes one or more flanges 610 at the upper edge of the substantially conical structure of the enclosure 600. The flanges 610 are positioned to locate the enclosure 600 relative to an outer surface of a wound dressing, and can be positioned to provide a surface for attachment of a cover (see, e.g. FIG. 5B). A flange 610 can include a flange region configured to cover part of an outer surface of the wound dressing when the appurtenance 120 is positioned for use with the wound dressing. One or more flanges 610 can be located on the enclosure 600 in a manner to functionally inhibit the movement of the enclosure 600 into the interior of the wound dressing layer. The one or more flanges 610 can be located on the enclosure 600 in a manner to expand a portion of the circumference of the enclosure 600 and prevent the appurtenance 120 from moving into the wound dressing beyond that expanded circumference. The enclosure 600 also includes one or more barbs 680 positioned to hold the appurtenance 120 in place relative to the affixed wound dressing and to prevent the appurtenance 120 from slipping relative to the wound dressing. Some embodiments include an enclosure 600 with one or more walls, the walls forming a flange 610 on an edge of the enclosure 600, the flange 610 positioned to attach a fastener between a surface of the wound dressing and the enclosure 600. Some embodiments include one or more walls, the walls forming one or more flanges 610 on the edge of the enclosure 600, the one or more flanges 610 including one or more projections from a surface of the one or more flanges 610, the one or more projections positioned to pierce an outer surface of the wound dressing. For example, one or more flanges 610 can include one or more barbs, points or projections positioned to pierce an outer surface of a wound dressing and assist in maintaining the position of the appurtenance relative to the wound dressing.

Figure 7:
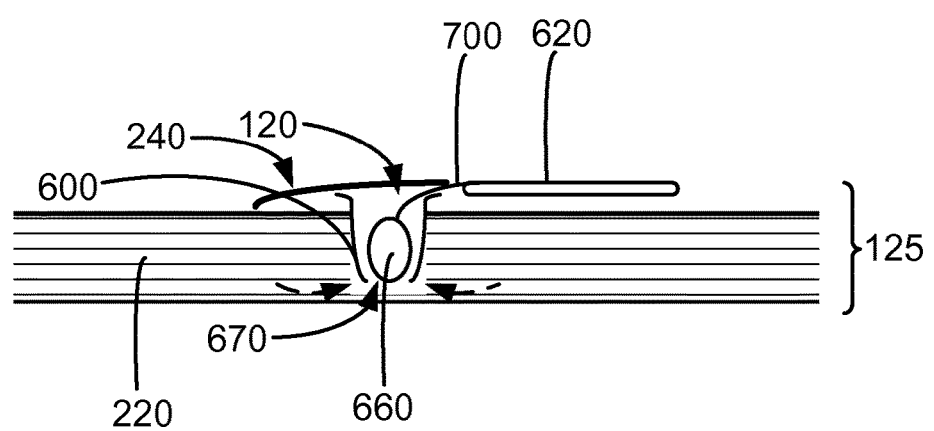
FIG. 7 is a schematic of an appurtenance to a wound dressing.

Some embodiments include a fastener configured to form a seal between an edge of an enclosure 610 and a surface of a wound dressing. For example, an edge of an enclosure 610 can include an adhesive configured to seal the edge of the enclosure 610 to a surface of the wound dressing. For example, as illustrated in FIG. 7, the fastener can include a substantially planar cover 240 with an upper surface and a lower surface, the lower surface conforming to both the edge of the enclosure 610 and to the surface of the wound dressing, and adhesive on at least a portion of the substantially planar cover 240.

Some embodiments include a piercing region operably attached to an edge of the enclosure 600 distal to an edge of the enclosure 600 adjacent to an outer surface of the wound dressing when the appurtenance is positioned for use with the wound dressing. For example, the enclosure 600 can include a tip, point, edge or surface projection configured to pierce a wound dressing surface when the appurtenance is affixed to the wound dressing.

As shown in FIG. 6, in some embodiments the one or more sensors 660 are positioned substantially within the enclosure 600. As illustrated in a cross-sectional view in FIG. 6, in some embodiments the enclosure 600 is configured to substantially enclose the one or more sensors 660. In some embodiments, the enclosure 600 includes one or more walls forming the enclosure 600, and one or more openings 670 within the one or more walls, the one or more openings 670 forming a conduit between a region exterior to the enclosure 600 and a region interior to the enclosure 600. For example, one or more openings 670 can form a conduit for analytes to pass from the interior of the wound dressing into the interior of the enclosure and for the analytes to come in contact with one or more sensors 660. The enclosure 600 can include an opening 670 at the end configured to be positioned within the wound dressing, and the one or more sensors 660 can be positioned adjacent to the opening 670. The one or more sensors 660 can be positioned adjacent to or within the opening 670 in a manner to allow the one or more sensors 660 to detect analytes within the wound dressing, such as through fluid flow (depicted as dotted arrows) from the interior of the wound dressing to a region adjacent to a sensor 660. Although a single opening 670 within the enclosure 600 is depicted in FIG. 6, in some embodiments there can be a plurality of openings in the enclosure, for example arrayed as a series of holes or a mesh-like structure. Some embodiments include a plurality of openings 670, wherein each opening 670 includes an associated sensor 660, such associated sensors 660 can be the same or different type of sensor 660.

As depicted in FIG. 6, in some embodiments the processor 640 operably connected to the one or more sensors 660 is positioned substantially within the enclosure 600. FIG. 6 depicts a single sensor 660 positioned substantially within the enclosure 600. In some embodiments, there can be a plurality of sensors 660, which can be of the same or different types. The one or more sensors 660 can include at least one sensor responsive to changes in capacitance. A connector 650, such as a wire connector, can operably connect the one or more sensors 660 to the processor 640. As illustrated in FIG. 6, in some embodiments the at least one transmitter unit 620 operably attached to the processor 640 is positioned substantially within the enclosure 600. A connector 630, such as a wire connector, can operably attach the processor 640 to the transmitter unit 620. Some embodiments include a processor 640 and a transmitter unit 620 that are powered through received signals (i.e. passive RFID). Some embodiments include a power source, such as a battery 690. A power source such as battery 690 can be integrated with the transmission unit 620, as depicted in FIG. 6. A power source such as battery 690 can be integrated with the processor 640. In some embodiments, a power source such as a battery 690 can be connected to the transmitter unit 620 and/or the processor 640, such as with a wire connector.

A variety of sensors can be utilized in different embodiments of the appurtenances, depending on factors such as the intended use of the appurtenance, size, weight, cost, biocompatibility, safety and ease of disposal. "Sensors," as used herein, can be of a variety of types depending on the embodiment. One or more sensors can include at least one sensor responsive to changes in capacitance, or a measure of the ability of a configuration of materials to store electric charge. A general review of biosensors that detect changes in the dielectric properties of an electrode surface can be found in Berggren et al., "Capacitive Biosensors," *Electroanalysis* vol. 13, no. 3, 173-180, (2001), which is incorporated herein by reference. For example, one or more sensors can include a micromechanical biosensor with a fixed-fixed beam attached to an interdigitated capacitor (see, for example, Lim et al., "A Micromechanical Biosensor with Interdigitated Capacitor Readout," *Proceedings of the* 2011 *IEEE/ICME International Conference on Complex Medical Engineering*, May 22-25, Harbin, China, which is incorporated herein by reference). Sensors can also include nanowire nanosensors, for example as described in Cui et al., "Nanowire Nanosensors for Highly Sensitive and Selective Detection of Biological and Chemical Species," *Science, vol.* 293, 1289-1292 (2001), which is incorporated herein by reference. Sensors can include those utilizing antibodies secured to a graphene substrate. See Tehrani et al., "Detection of Monoclonal Antibodies using Chemically Modified Graphite Substances," *IEEE Sensors* 2010 *Conference Proceedings*, 428-431, (2010), which is incorporated herein by reference. In some embodiments, sensors include aptamer-modified graphene field-effect transistors, see Ohno et al., "Graphene Field-Effect Transistors for Label-Free Biological Sensors," *IEEE Sensors* 2010 *Conference Proceedings*, 903-906, (2010), which is incorporated herein by reference. A sensor in an appurtenance can interact with a sensor present in a wound dressing, for example as described in U.S. Pat. No. 6,283,938 to McConnell, titled "Medicating Bandage and Controllable Permeable Membrane," which is incorporated herein by reference. A sensor can include a field effect transistor (FET), such as described in U.S. Pat. No. 7,507,675 to Zuilhof et al., titled "Device Manufacturing Method and Device," which is incorporated herein by reference. A sensor can include a nano-cantilever device, such as described in U.S. Pat. No. 7,612,424 to Espinosa and Ke, titled "Nanoelectromechanical Bistable Cantilever Device," which is incorporated herein by reference.

Sensors such as those described herein can be configured to sense fluids. Sensors such as those described herein can be configured to sense one or more components of a fluid. Sensors such as those described herein can be configured to sense one or more analytes within a fluid. As used herein, fluid includes both gasses and liquids individually or as mixtures. Sensors described herein can detect fluids, whether in gaseous state or liquid state. If the fluid is a liquid, it can be drawn into an appurtenance through capillary action. If the fluid is a gas, it can be drawn into the appurtenance through gravity (i.e. where the appurtenance is oriented on the top of a wound dressing over a wound). In some embodiments, the appurtenance includes a micropump positioned to move fluids through a projection and into the appurtenance in a position adjacent to a sensor. Each sensor is in fluid communication with the portion of the appurtenance relative to the insertion point into the wound dressing, or the projection 200. In some embodiments, the appurtenance includes a sealed chamber that is under vacuum and connected to the projection. When the seal is broken, it sucks up the fluid into the tube in response to the low (or negative) air pressure in the tube.

As illustrated in FIG. 6, in some embodiments a processor 640 is operably attached to the one or more sensors 660. For example, the processor can be connected with a wire connector 650, configured to allow the sensor to send information to the processor. The processor 640 is configured to receive information from the sensor. The processor 640 can include one or more processing cores, and can include any of a number of types of processors commonly in use. The processor 640 can include volatile or non-volatile memory. The appurtenance 120 can include a volatile or non-volatile memory unit operably attached to the processor 640. The processor 640 can hold in memory a unique identifier for the specific appurtenance 120. For example, the processor 640 can include an identifying number specific to that appurtenance 120.

The appurtenance 120 can include an energy storage unit. For example, an appurtenance 120 can include an energy storage unit, such as a battery, operably attached to the processor 640. In some embodiments, the appurtenance 120 does not store energy. The appurtenance 120 can include an energy harvesting unit, such as a unit configured to obtain energy from electromagnetic waves. See, for example, U.S. Pat. No. 7,479,886 to Burr titled "Antenna Capacitance for Energy Storage" and Sample et al., "Photovoltaic Enhanced UHF RFID Tag Antennas for Dual Purpose Energy Harvesting," 2011 *IEEE International Conference on RFID*, 146-153 (2011), which are each incorporated herein by reference. In some embodiments, the appurtenance 120 includes an indicator operably attached to the processor 640, the indicator positioned on a side of the appurtenance adjacent to an outer surface of the wound dressing when the appurtenance is positioned for use with the wound dressing. For example, the indicator can include a least one of: a visual indicator, a vibratory indicator, or an auditory indicator. See, for example, US Patent Application No. 2009/0167495 to Smith, titled "Radio Frequency Identification Tags Adapted for Localization and State Indication," which is incorporated herein by reference.

As shown in FIG. 6, in some embodiments at least one transmitter unit 620 is operably attached to the processor 640. In some embodiments, the at least one transmitter unit 620 and the processor 640 are operably connected with a wire connection 630.

A "transmitter unit," as used herein, can be one or more of a variety of units that are configured to send and/or receive signals, such as signals carried as electromagnetic waves. In embodiments where the appurtenance includes a substrate, the transmission unit can be attached to a surface of the substrate, the transmission unit including circuitry and at least one antenna, the transmission unit configured to transmit a signal. A transmitter unit generally includes at least one antenna and associated circuitry. A transmitter unit can include a transmitter and a receiver. A transmitter unit can include volatile or non-volatile memory. A transmitter unit can include a processor. A transmitter unit can be operably connected to an energy source, such as a battery. In some embodiments of an appurtenance, it is desirable to include a self-compensating antenna, such as described in U.S. Pat. No. 7,055,754 to Forester, titled "Self-Compensating Antennas for Substrates having Differing Dielectric Constant Values," which is incorporated herein by reference. A transmitter unit can be operably connected to a processor, as illustrated in FIG. 6. A transmitter unit can be operably connected to a sensor. A transmitter unit can be configured to transmit a signal in response to an interrogation signal. A transmitter unit can include an energy harvesting unit, such as a unit configured to obtain energy from electromagnetic waves. A transmitter unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmitter unit can include an oscillator and encoder configured to generate a programmable pulse position-modulated signal in the radio frequency range. See, for example, U.S. Pat. No. 4,384,288 to Walton, titled "Portable Radio Frequency Emitting Identifier," which is incorporated herein by reference. A transmitter unit can include a radio frequency identification device (RFID). A transmitter unit can be configured to be a transmitter of signals in the UHF range. A transmitter unit including an RFID device can be configured to transmit signals in the UHF standard range utilized in a global region, as illustrated in the "Worldwide RFID UHF Map" by Intelleflex Corporation (©2009), which is incorporated herein by reference. A transmitter unit can include a radio frequency identification device (RFID), which can be a passive RFID device, a semi-passive RFID device, or an active RFID device, depending on the embodiment. See, for example, Chawla and Ha, "An Overview of Passive RFID," *IEEE Applications and Practice*, 11-17 (September 2007), which is incorporated herein by reference. A transmitter unit can include a battery-assisted passive RFID device, such as sold by Alien Technology®, Morgan Hill, Calif., such as described in the brochure from Alien Technology® titled "Battery Assisted Passive Tags" and incorporated herein by reference. A transmitter unit can include an optical transmitter unit. A transmitter unit can be configured to transmit at approximately 13.56 megahertz (MHz), or within the ISO 14443 standard parameters. See Patauner et al., "High Speed RFID/NFC at the Frequency of 13.56 MHz," presented at the *First International EURASIP Workshop on RFID Technology*, pages 1-4, 24-25 Sep. 2007, Vienna Austria, which is incorporated herein by reference. A transmitter unit can include at least two antennas. A transmitter unit can include a self-compensating antenna system. An antenna can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference. A transmitter unit can include a hybrid backscatter system configured to function in an RFID, IEEE 802.11x standard and Bluetooth system. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. A transmitter unit can be configured to transmit at approximately 131 kilohertz (KHz), for example as part of a RuBee™ (IEEE standard 1902.1) system (sold, for example, by Visible Assets™, Inc.). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference. A transmitter unit can include a near field communication (NFC) device. A transmitter unit can include a Wireless Identification and Sensing Platform (WISP) device, manufactured by Intel Corporation, such as described in the "WISP: Wireless Identification and Sensing Platform" webpage (downloaded on Oct. 28, 2011) incorporated herein by reference. A transmitter unit can be operably coupled to a sensor, such as a sensor that detects changes in capacitance (see, e.g. Sample et al., "A Capacitive Touch Interface for Passive RFID Tags," 2009 *IEEE International Conference on RFID*, 103-109 (2009), which is incorporated herein by reference). A transmitter unit can be operably coupled to a sensor, such as described in: Ruhanen et al., "Sensor-enabled RFID Tag and Handbook," from *Building Radio Frequency Identification for the Global Environment* (2008); Sample et al., "Design of an RFID-Based Battery-Free Programmable Sensing Platform," *IEEE Transactions on Instrumentation and Measurement*, vol. 57, no. 11, 2608-2615 (2008); Yeager et al., "Wirelessly-Charged UHF Tags for Sensor Data Collection," 2008 IEEE International Conference on RFID, Apr. 16-17, 2008, pages 320-327; U.S. Pat. Nos. 5,904,671 and 6,348,640 to Navot and Botton, each titled "Tampon Wetness Detection System;" U.S. Pat. No. 7,446,660 to Posamentier titled "Passive Environmental RFID Transceiver;" and U.S. Pat. No. 5,704,352 to Tremblay and Buckles, titled "Implantable Passive Bio-Sensor," which are each incorporated herein by reference. A transmission unit can be operably coupled to a data storage unit, for example as described in U.S. Pat. No. 7,825,776 to Smith and Haehnel, titled "Device Configuration with RFID," and US Patent Application No. 2009/0243813 to Smith at al., titled "Wireless Programming of Non-Volatile Memory with Near-Field UHF Coupling," which are each incorporated herein by reference.

In some embodiments, the transmitter unit can include an acoustic transmitter. For example, a transmitter unit can include a piezoelectric speaker. A variety of suitable piezoelectric speakers are available, including from Murata Manufacturing Co., Ltd., with North American corporate headquarters in Smyrna, Ga. (see, e.g. the Murata catalog titled "Piezoelectric Sounds Components" labeled P37E and dated Jan. 28, 2010, which is incorporated herein by reference). Some embodiments can include acoustic transmitter units such as those manufactured by Advanced Telemetry Systems (headquartered in Isanti, Minn.) for the Pacific Northwest National Laboratory (see, e.g. JSATS Acoustic Transmitter information sheet from the Pacific Northwest National Laboratory, updated March 2010, which is incorporated herein by reference). In some embodiments, an appurtenance can include a piezoelectric speaker configured as part of an acoustic transmitter and also to act as a signaling device (e.g. to generate a beeping noise in response to a signal from the processor).

In some embodiments, the transmitter unit can include an ultrasonic transmitter. In some embodiments, the transmitter unit can include an ultrasonic transducer. Multiple examples of ultrasonic transmitters and transducers are commercially available, often marketed under the term "ultrasonic sensors" as it is used in the industry (see, e.g. the Murata catalog titled "Ultrasonic Sensor" labeled S15E and dated Oct. 31, 2008, which is incorporated herein by reference). The transmitter unit can be configured as part of an ultrasonic ranging system. See: Wang, "A Design Method of Ultrasonic Ranging System with High Accuracy," *Journal of Computational Information Systems,* 7: 7 pages 2444-2451 (2011), which is incorporated herein by reference. The transmitter unit can be configured to communicate with an ultrasonic communication system. See: Chen and Wu, "Ultrasonic System with Infrared Communication Technology," *Journal of Computers, vol.* 6, no. 11, pages 2468-2475 (2011), which is incorporated herein by reference.

In some embodiments, the transmitter unit can include an optical transmitter. For example, an optical transmitter unit can include one or more white light emitting diodes (LEDs). For example, an optical transmitter unit can include an infrared laser. In some embodiments, optical transmitter units can be desirable to minimize interference from nearby electrical equipment, such as medical equipment. See: Kavehrad, "Sustainable Energy-Efficient Wireless Applications Using Light," *IEEE Communications Magazine*, vol. 48, no. 12, pages 66-73, (2010); and Fadlullah and Kavehrad, "Indoor High-Bandwidth Optical Wireless Links for Sensor Networks" *Journal of Lightwave Technology*, vol. 28, no. 21, pages 3086-3094 (2010), which are incorporated herein by reference.

FIG. 7 illustrates some aspects of an embodiment of an appurtenance 120. The appurtenance has been irreversibly affixed to a wound dressing to form a combination unit 125. Although the appurtenance 120 of FIG. 7 is an embodiment distinct from the embodiment illustrated in FIG. 6, the embodiment illustrated in FIG. 6 is configured similarly in that the enclosure 600 fits substantially within the main thickness of the wound dressing interior region 220. FIG. 7 depicts an appurtenance 120 including an enclosure 600 and a sensor unit 660 substantially surrounded by the enclosure 600. In some embodiments, the enclosure 600 is fabricated from one or more flexible materials, for example a flexible plastic material. FIG. 7 illustrates an appurtenance to a wound dressing affixed to a wound dressing 125. FIG. 7 shows that the appurtenance includes: a sensing unit 660 including one or more sensors, the sensors positioned substantially within an enclosure of a height and width to fit substantially within an interior region of a wound dressing; a transmission unit 620 including a processor and at least one transmitter unit operably attached to the processor; and a connector 700 between the sensing unit 660 and the transmission unit 620, the connector 700 configured to convey signals between the one or more sensors and the transmission unit 620. For example, the connector 700 can include a wire. The sensor unit 660 is positioned adjacent to an opening 670 in the enclosure 600, the opening 670 positioned on the enclosure 600 at a position to allow analytes to flow (as depicted by hatched arrows) from an interior region of the wound dressing 220 into a position in contact with the sensor unit 660. In some embodiments, the sensor unit 660 can be configured to be responsive to changes in circuitry capacitance. As shown in FIG. 7, the sensor unit 660 is operably attached to a transmission unit 620 via one or more connectors 700 including wires. The transmission unit 620 can include, for example, one or more antennas, a non-volatile memory, and related circuitry. The transmission unit 620 can include, for example, an antenna and a receiver operably attached to the antenna. The transmission unit 620 can include, for example, non-volatile memory. The transmission unit 620 can include, for example, a substrate including at least one surface configured to conform to an exterior surface of a body. For example, the transmission unit 620 can, in whole or part, be attached to an exterior surface of the body adjacent to the wound dressing. The transmission unit 620 can, in whole or part, be attached to an exterior surface of the body in situations, for example, where the main wound dressing is too small to accommodate the square area of the transmission unit 620, or where other space parameters make that option desirable. In an embodiment of an appurtenance 120, such as illustrated in FIG. 7, wherein the transmission unit 620 including at least one antenna is positioned on top of the wound dressing, it can be desirable to include a self-compensating antenna system, such as described in U.S. Pat. No. 7,055,754 to Forester, titled "Self-Compensating Antennas for Substrates having Differing Dielectric Constant Values," which is incorporated herein by reference. A cover 240 is positioned at the upper surface of the appurtenance 120, the cover 240 positioned to secure the appurtenance 120 relative to the surface of the wound dressing 220. The cover 240 can be configured to seal the junction between the edge of the enclosure 600 and the edge of the wound dressing. In some embodiments, the appurtenance can include an indicator operably attached to the transmission unit 620. For example the appurtenance can include an indicator which is at least one of: a visual indicator, a haptic indicator, or an auditory indicator.

Figure 8A:
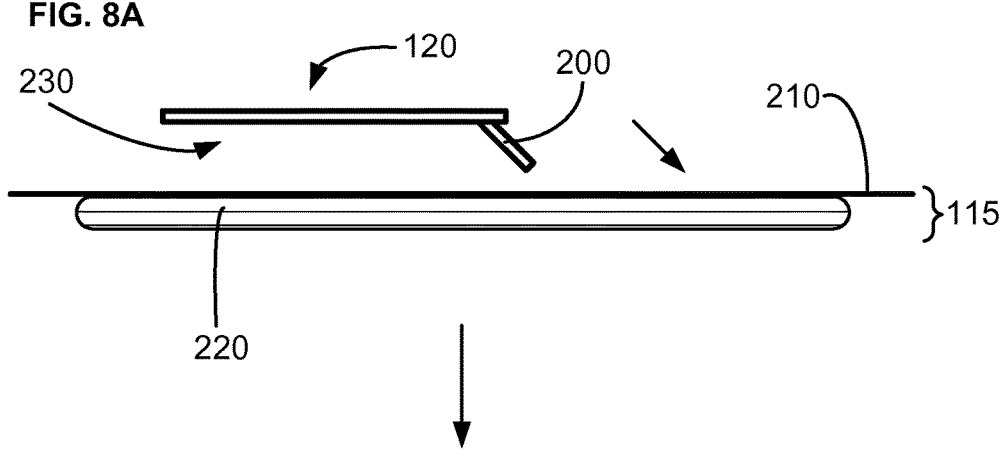
FIG. 8A is a schematic of an appurtenance to a wound dressing prior to attachment to a wound dressing.
Figure 8B:
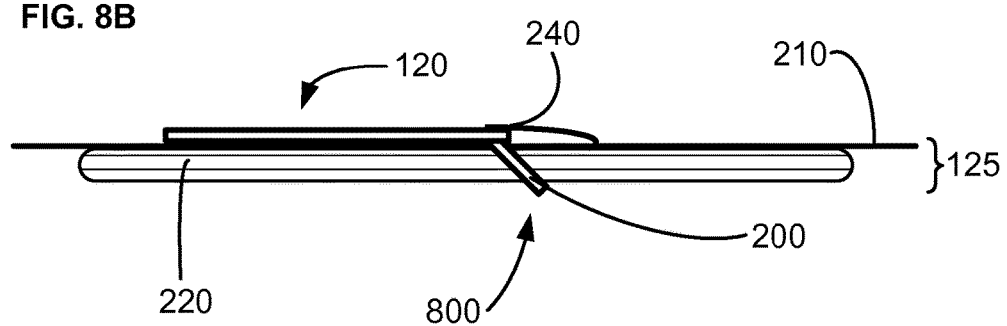
FIG. 8B is a schematic of an appurtenance to a wound dressing after attachment to a wound dressing.

FIGS. 8A and 8B illustrate additional aspects of an appurtenance 120 to a wound dressing 115. As illustrated in FIG. 8A, an appurtenance 120 can include a projection 200. The appurtenance 120 can include a surface 230 conforming to an outer surface of a wound dressing 115. The wound dressing 115 can include an outer layer 210 and a wound dressing layer 220. As shown in FIG. 8B, when the appurtenance 120 is irreversibly affixed to the wound dressing to form an appurtenance-wound dressing combination unit 125, the projection 200 includes a region 800 that projects through the layers of the wound dressing 210, 220 and beyond the surface of the wound dressing that is configured to face the wound. As shown in FIGS. 8A and 8B, in some embodiments a projection 200 is of a size and shape to project through a width of the wound dressing when the appurtenance 120 is attached to the wound dressing. In embodiments where the wound dressing is intended to overlay an additional bandage or dressing, the additional projection region 800 can be configured to project into the additional bandage or dressing. For example, in some situations, a medical caregiver can select a treatment for a wound that includes a layer of gauze, potentially impregnated with a medicinal agent, at the surface of the wound and then a wound dressing overlay over the gauze layer. A region 800 of a projection 200 from an appurtenance 120 can project into such a gauze layer.

Also as illustrated in FIG. 8B, in some embodiments the appurtenance wound dressing unit 125 includes at least one cover 240. The at least one cover 240 can include at least one substantially planar cover 240, the cover 240 including an adhesive on a surface conforming to a surface of the wound dressing, the substantially planar cover 240 configured to cover at least a part of the projection 200. For example, the cover 240 can seal the junction region between the appurtenance 120 and the wound dressing 115, for example from external dirt, debris, wetness and microbes.

FIGS. 9A and 9B illustrate aspects of an appurtenance 120 configured for irreversible attachment to a wound dressing 115. A shown in FIG. 9A, an appurtenance 120 can include a projection 200. The projection 200 can be configured as a tapered conical shape. The projection 200 can be configured in a curved shape. A curved, hook-like shape for a projection 200, as illustrated in FIGS. 9A and 9B, can be desirable for ease of attachment to the wound dressing 115. A single motion, as depicted in the hatched arrow, can be sufficient for a user to position and affix an appurtenance 120 with a hook-like projection 200 to a wound dressing 115. The appurtenance 120 can include a surface 230 conforming to an outer surface of a wound dressing 115. The wound dressing 115 can include an outer layer 210 and a wound dressing layer 220. When the appurtenance 120 is affixed to the wound dressing 115 to form a wound dressing-appurtenance combination unit 125, as shown in FIG. 9B, the curved projection 200 can be stable within the layers 210, 220 of the wound dressing. The appurtenance wound dressing unit 125 can also include at least one cover 240. The at least one cover can seal the junction between the appurtenance and the wound dressing, and can also stabilize the appurtenance relative to the wound dressing.

Figure 10A:
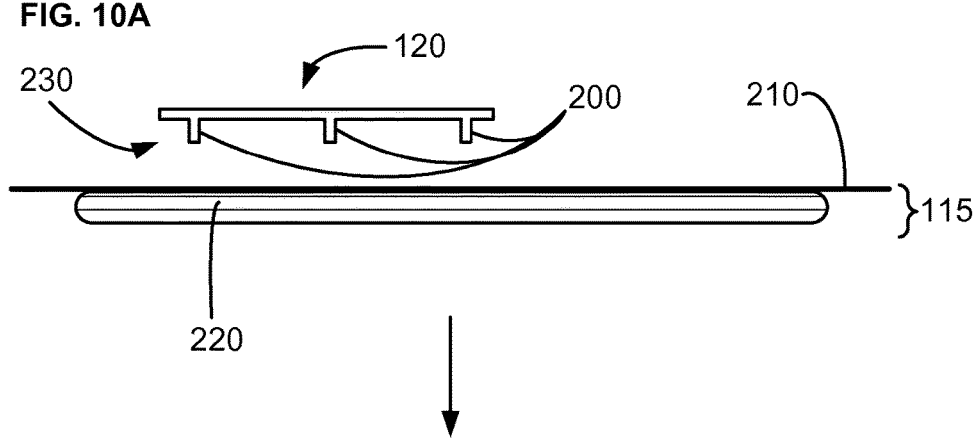
FIG. 10A is a schematic of an appurtenance to a wound dressing prior to attachment to a wound dressing.
Figure 10B:
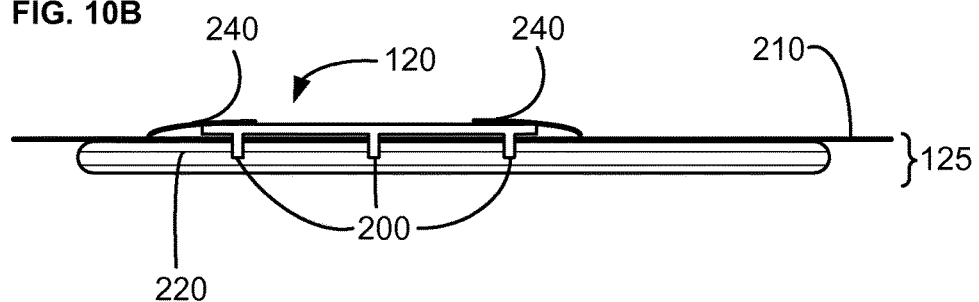
FIG. 10B is a schematic of an appurtenance to a wound dressing after attachment to a wound dressing.

In some embodiments, an appurtenance 120 includes a plurality of projections 200. As shown in FIGS. 10A and 10B, an appurtenance 120 can include more than one projection 200. The projections 200 can be spaced at regular or irregular intervals over a surface of the appurtenance 120. The projections 200 can all be of substantially the same size and shape, as shown in FIGS. 10A and 10B, or they can be of different sizes and shapes to project at different levels and amounts into a wound dressing 115. The projections 200 of an appurtenance 120 can be selected relative to the intended use of the appurtenance 120, including an associated wound dressing 115, the intended length of time of use, and monitoring sensitivity of the appurtenance 120. Projections 200 at different levels and amounts into a wound dressing 115 can be oriented, for example, to form conduits for fluid flow between different layers of a wound dressing and sensor(s) of the appurtenance 120. Projections 200 of different levels and amounts into a wound dressing 115 can be useful, for example, to fully monitor a wound dressing 115 with multiple layers. FIG. 10A illustrates that a wound dressing 115 can include an outer layer 210 and an inner layer 220. As shown in FIG. 10B, in embodiments wherein an appurtenance 120 includes a plurality of projections 200 of a similar size and shape, the projections would be expected to end at a similar relative depth or width of the wound dressing 115 when the appurtenance is affixed to the wound dressing as a unit 125. In an embodiment wherein an appurtenance includes a plurality of projections of different sizes and shapes (not illustrated in FIG. 10B), the projections would reach to different levels or depths of a wound dressing. Projections 200 of different levels and amounts into a wound dressing 115 can be useful, for example, to fully monitor a wound dressing 115 with multiple functional regions or layers, such as regions or layers with different absorbance properties. Projections 200 of different levels and amounts into a wound dressing 115 can be useful, for example, to efficiently monitor a wound dressing 115 of sufficient thickness that fluid flow throughout the entire wound dressing 115 requires an excess amount of time. Also as shown in FIG. 10B, in some embodiments an appurtenance wound dressing unit 125 can also include at least one cover 240.

The projections 200 can be functionally the same, or they can be different. Projections 200 at different levels and amounts into a wound dressing 115 can be oriented, for example, to form conduits for fluid flow between different regions of a wound dressing 115 and/or a wound bed region and sensor(s) of the appurtenance 120. Projections 200 can include the same type of sensors, or be connected to the same type of sensors, or they can include different types of sensors, or be connected to different types of sensors. For example, in some embodiments sensors detecting pH changes in a wound dressing can be more desirable in a central location of the appurtenance 120 and sensors detecting wetness can be more desirable at an edge region of the appurtenance 120. In this example, pH changes can indicate potential infection in the central wound region, while edge wetness can indicate that the wound dressing is saturated and should be replaced. Sensors for pH suitable for some embodiments are known. See, for example, the "flexible, iridium oxide pH sensor for wound dressing material" project from the University of Texas at Arlington, the information sheet for which, with UTA reference number 08-21, is herein incorporated by reference.

Figure 11A:
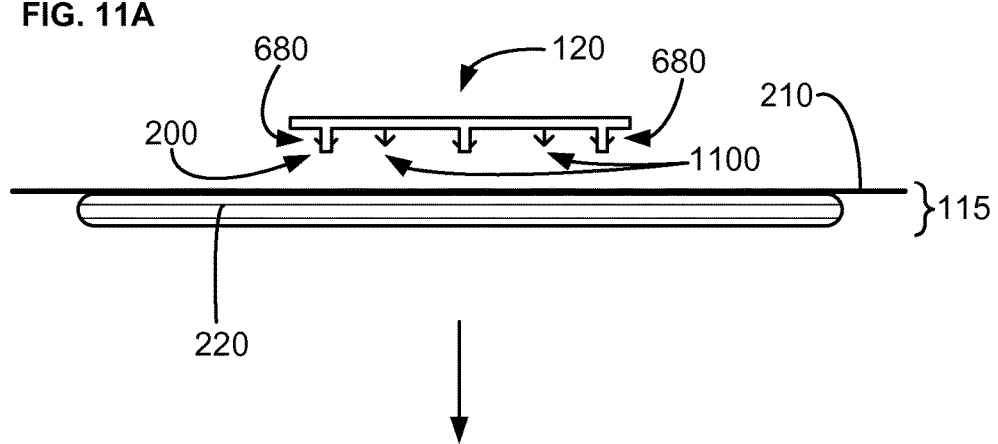
FIG. 11A is a schematic of an appurtenance to a wound dressing prior to attachment to a wound dressing.
Figure 11B:
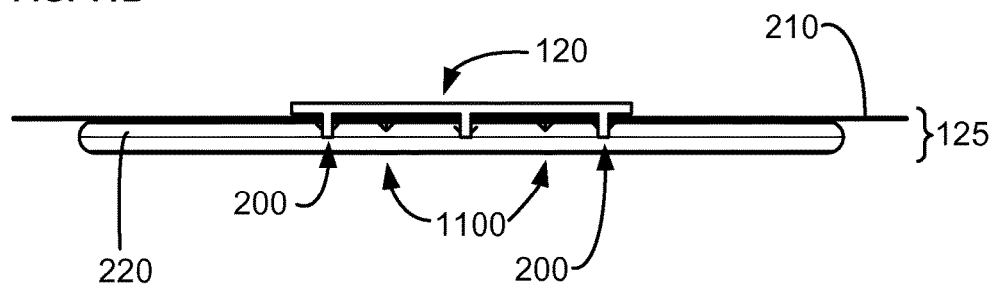
FIG. 11B is a schematic of an appurtenance to a wound dressing after attachment to a wound dressing.

FIGS. 11A and 11B show additional features that can be present in an appurtenance 120 to a wound dressing 115. As shown in FIG. 11A, in some embodiments an appurtenance 120 to a wound dressing 115 can include a plurality of projections 200. One or more of the projections 200 can include a barb-like feature 680, wherein the barb-like feature 680 is configured to bend during insertion of the projection 200 into one or more layers 210, 220 of a wound dressing 115 but then prevent the movement of the projection 200 away from the wound dressing 115. For example, as illustrated in FIGS. 11A and 11B, in some embodiments one or more projections 200 include at least one extension that protrudes outwards from the side of the projection 200 at an angle larger than 90 degrees from the direction of motion of the projection 200 into the wound dressing 115. The at least one extension from the projection 200, therefore, acts as a barb to prevent the appurtenance 120 moving away from the wound dressing 115 (as illustrated in FIG. 11B). An appurtenance 120 can also include one or more barbed attachments 1100 configured to irreversibly attach the appurtenance 120 to the wound dressing 115. As shown in FIG. 11B, the one or more barbed attachments 1100 can be configured to traverse multiple layers 210, 220 of the wound dressing 115 and, therefore, stabilize the attachment of the appurtenance 120 to the wound dressing 115 in the wound dressing-appurtenance combination unit 125.

Figure 12:
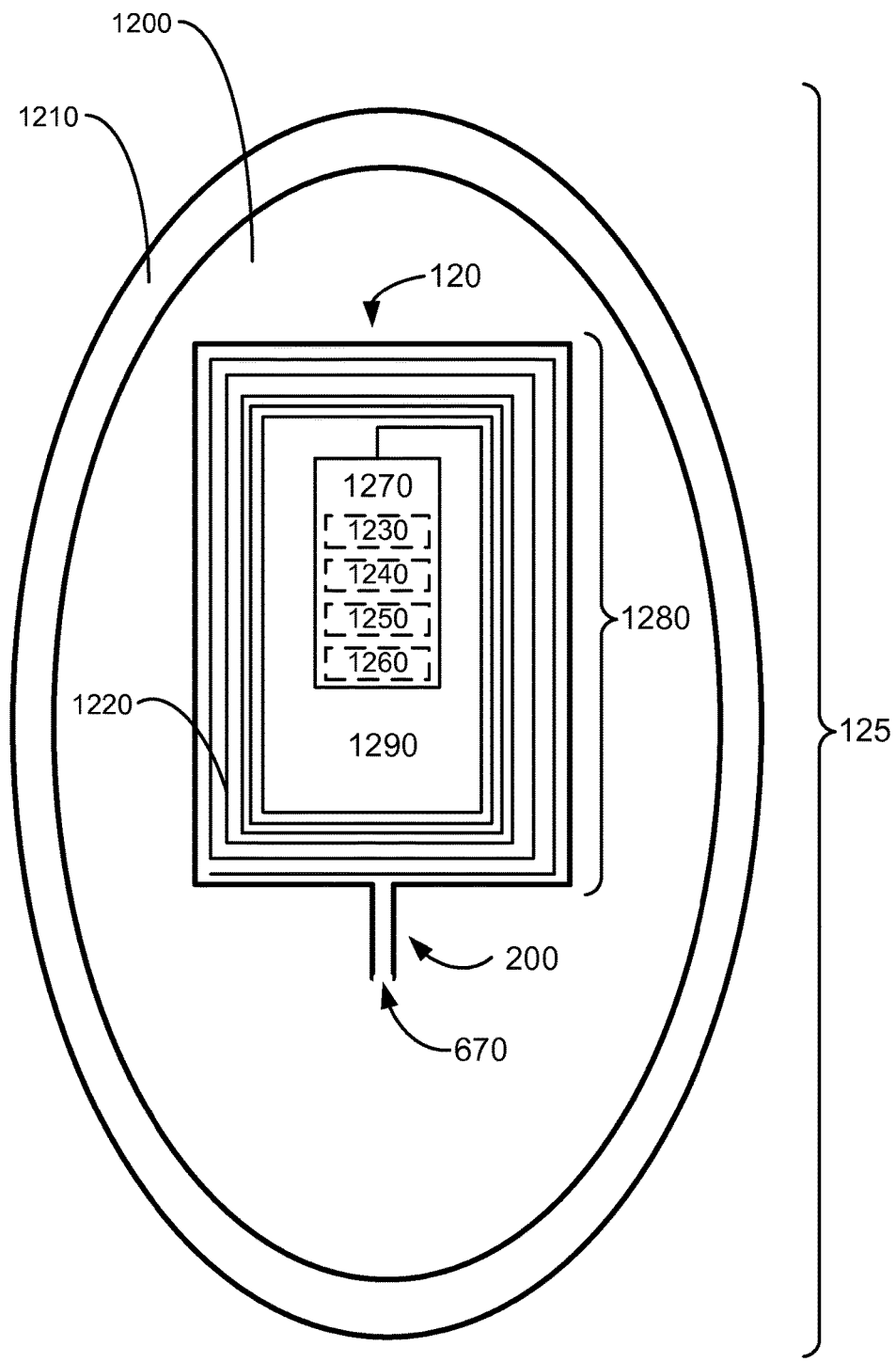
FIG. 12 is a schematic of an appurtenance to a wound dressing.

FIG. 12 illustrates aspects of an appurtenance affixed to a wound dressing unit 125. The view illustrated in FIG. 12 is a substantially top-down view, as seen from the top of an appurtenance affixed to a wound dressing unit 125 looking down on to the unit. The side of the wound dressing-appurtenance combination unit 125 illustrated in FIG. 12 is the side that would be away from a wound during use. The side of the wound dressing-appurtenance combination unit 125 illustrated in FIG. 12 is the opposing face to the surface of the unit configured for use adjacent to a body part. As shown in FIG. 12, a wound dressing can include a wound covering region 1200 and an edge region 1210. The wound covering region 1200 can include one or more layers of a wound dressing, such as gauze, foam, hydrocolloids, and other types of wound dressings singly or in combination. The edge region 1210 can include, for example, a structural region configured to provide shape and support to the wound covering region 1200. The edge region 1210 can include, for example, an adhesive configured to attach the edge region 1210 to a surface of a body part in an area adjacent to a wound. The edge region 1210 can include, for example, a cover configured to seal the edge region 1210 and the adjacent body part surface from substances moving between the edge region 1210 and the adjacent body part surface. For example, the edge region 1210 can include a cover configured to prevent wetness, debris, dirt or microbial agents from travelling between the edge region 1210 and the body surface.

As shown in FIG. 12, an appurtenance 120 affixed to a wound dressing to form a wound dressing-appurtenance combination unit 125 includes a substrate 1290. The substrate 1290 can include, for example, a flexible plastic, which can be configured in a thin film or as a mesh of no more than a few millimeters (mm) in thickness. For example, the substrate 1290 can be no more than 3 mm, or no more than 5 mm, thick depending on the embodiment. The substrate 1290 can include, for example, a flexible paper material. The substrate 1290 can include, for example, a composite material. The substrate 1290 can include, for example, one or more materials with properties such as durability, strength, cost, weight, bio-compatibility and disposability that are suitable for a given embodiment. The substrate 1290 is configured to irreversibly attach to the wound covering region 1200 of the wound dressing. For example, the substrate 1290 can include an adhesive material on the face configured to conform to the surface of the wound dressing 1200. For example, the substrate 1290 can include one or more barbs, hooks or other projections (see, e.g. FIGS. 11A and 11B) on the face configured to conform to the surface of the wound dressing 1200.

Also as illustrated in FIG. 12, the appurtenance 120 affixed to a wound dressing to form a wound dressing-appurtenance combination unit 125 includes a transmission unit 1280 attached to a surface of the substrate. The transmission unit 1280 includes circuitry 1270 and at least one antenna 1220. Although the transmission unit 1280 is illustrated as visible in FIG. 12, in some embodiments all or part of the transmission unit 1280 will be covered and not be visible. The transmission unit 1280 is configured to transmit a signal. As illustrated in FIG. 12, an antenna 1220 can be a substantially planar antenna, such as commonly used in radio frequency identification (RFID) or near field communication (NFC) units. Prior to use, the antenna 1220 can be detuned with a removable surface layer of a conductive material. This can be desirable to reduce excess RFID signals, for example from appurtenances 120 in storage prior to attachment to a wound dressing. See U.S. Pat. No. 7,724,136 to Posamentier, titled "Revealable RFID Devices," which is incorporated herein by reference. The circuitry 1270 of the transmission unit 1280 can include a variety of components, as desired in a particular embodiment. The circuitry 1270 of the transmission unit 1280 can include a processor 1230. The circuitry 1270 can include non-volatile memory 1240. The circuitry 1270 can include a transmitter 1250. The circuitry 1270 can include one or more additional modules 1260. For example, the circuitry 1270 can include an energy source, such as a battery. For example, the circuitry 1270 can include a receiver. For example, the circuitry 1270 can include a transceiver. For example, the circuitry 1270 can include an additional antenna. For example, the circuitry 1270 can include volatile memory. The circuitry 1270 can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference.

In some embodiments, the transmission unit can include a pressure sensitive activation region, wherein the pressure sensitive activation region is configured to be activated by physical pressure between a surface of the substrate and a surface of the wound dressing. In some embodiments, the transmission unit can include a pressure sensitive activation region, wherein the pressure sensitive activation region is configured to be activated by physical pressure on a surface of the appurtenance. In some embodiments, the transmission unit can include a pressure sensitive activation region, wherein the pressure sensitive activation region is configured to be activated by physical pressure between a surface of the substrate and a surface of the wound dressing. See, for example, U.S. Pat. Nos. 6,693,513 and 6,037,879 to Tuttle, titled "Wireless Identification Device, RFID Device with Push-On/Push-Off Switch, and Method of Manufacturing Wireless Identification Device," and U.S. Pat. No. 6,863,220 to Selker, titled "Manually Operated Switch for Enabling and Disabling an RFID Card," as well as Sample et al., "A Capacitive Touch Interface for Passive RFID Tags," 2009 *IEEE International Conference on RFID*, 103-109 (2009), which are each incorporated herein by reference.

FIG. 12 illustrates that the appurtenance 120 affixed to a wound dressing to form a wound dressing-appurtenance combination unit 125 includes a projection 200. Although the projection 200 is displayed for the purposes of illustration, when an appurtenance 120 is affixed to a wound dressing to form a wound dressing-appurtenance combination unit 125 in normal use, the projection 200 would extend into an interior region of the wound dressing (see, e.g. FIGS. 2B, 8B, 9B, 10B and 11B), and, therefore, not be visible from a superficial view. As illustrated in FIG. 12, in some embodiments a projection 200 includes a physical conduit configured to permit fluid to flow from the interior region of the wound dressing 1200 to a location in contact with the transmission unit 1280. For example, in some embodiments a projection 200 includes a physical conduit configured to allow a flow of the fluid from the interior region of the wound dressing 1200 to a location in contact with the antenna 1220 of the transmission unit 1280. The projection 200 can include a substantially hollow tubular structure. The projection 200 includes an opening 670 at the end of the projection 200 distal to the end of the projection 200 adjacent to the substrate 1290. The projection 200 can be of a size and shape to project from the outer surface of the wound dressing to within layers of the wound dressing. The projection 200 can be of a size and shape to project underneath one or more superficial structures of the wound dressing when the wound dressing is in use. The projection 200 can be of a size and shape to project through a width of the wound dressing when the appurtenance is attached to the wound dressing. See, e.g. FIGS. 2B, 8B, 9B, 10B and 11B.

In some embodiments, the projection 200 is fabricated from a plastic material. For example, the projection 200 can be fabricated from a pliable plastic material. For example, the projection 200 can be fabricated from a bio-compatible plastic material. For example, the projection 200 can be fabricated from a plastic material that can be sterilized prior to use of the appurtenance 120.

Figure 13:
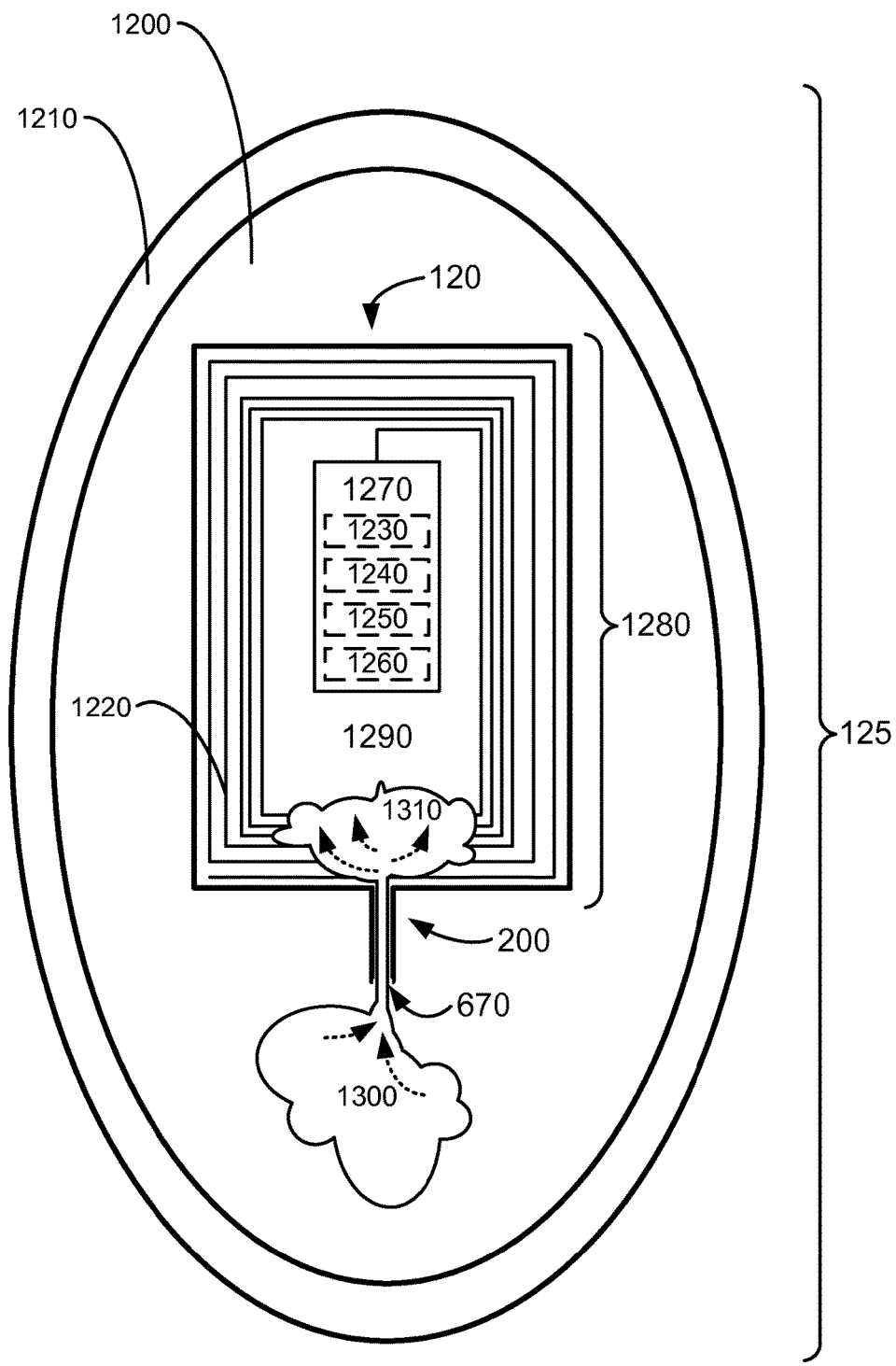
FIG. 13 is a schematic of an appurtenance to a wound dressing.

FIG. 13 illustrates further aspects of an appurtenance 120 such as that shown in FIG. 12. FIG. 13 illustrates that the appurtenance 120 affixed to a wound dressing to form a wound dressing-appurtenance combination unit 125 includes a projection 200. Although the projection 200 is shown in FIG. 13 for the purposes of illustration, in actual use the projection 200 would project into one or more layers of the wound covering region 1200 of the wound dressing. FIG. 13 also illustrates that the wound covering region 1200 contains a fluid 1300. The fluid 1300 can include, for example, blood, serum, pus, wound exudates, excess saline, or other fluids that can be present in the interior of the wound dressing. For example, the fluid 1300 can include blood, such as when an acute wound is bleeding excessively, as can occur when a suture has broken open. For example, the fluid may include gas, such as emitted from infected tissue (e.g. $NO_2$). For example, the fluid 1300 can include wound exudates, such as those that are characteristic of infected wounds (see for example, Cutting and Harding, "Criteria for Identifying Wound Infection," *Journal of Wound Care*, vol. 3, no. 4, 198-201 (1994), which is incorporated herein by reference).

FIG. 13 also illustrates that the fluid 1300 has moved into the projection 200 through the opening 670. The fluid can flow through the projection 200 through a variety of forces depending on the embodiment, for example through capillary action, under a physical pressure differential, or diffusion. When the migrated fluid 1310 comes into contact with the transmission unit 1280, the migrated fluid 1310 modulates the transmission unit 1280. For example, when the migrated fluid 1310 comes into contact with the antenna 1220 of the transmission unit 1280, the fluid 1310 can modulate the antenna 1220 through alterations of the frequency to which the antenna 1220 responds. The migrated fluid 1310 can result in the loss of antenna 1220 function. For example, when the migrated fluid 1310 comes into contact with the transmission unit 1280, the fluid 1310 modulates activity of the circuitry unit 1270. The migrated fluid 1310 can result in the loss of circuitry unit 1270 function. The migrated fluid 1310 can result in the loss of circuitry unit 1270 function, for example through alterations of the electrical paths of the circuitry within the circuitry unit 1270. The migrated fluid 1310 can result in the mitigation of ability of the transmission unit 1280 to transmit a signal. The migrated fluid 1310 can result in the loss of ability of the transmission unit 1280 to transmit a signal. This loss can be detected by an associated signal reader and/or system (see, e.g. FIGS. 18, 19, 20 and 21).

Figure 16:
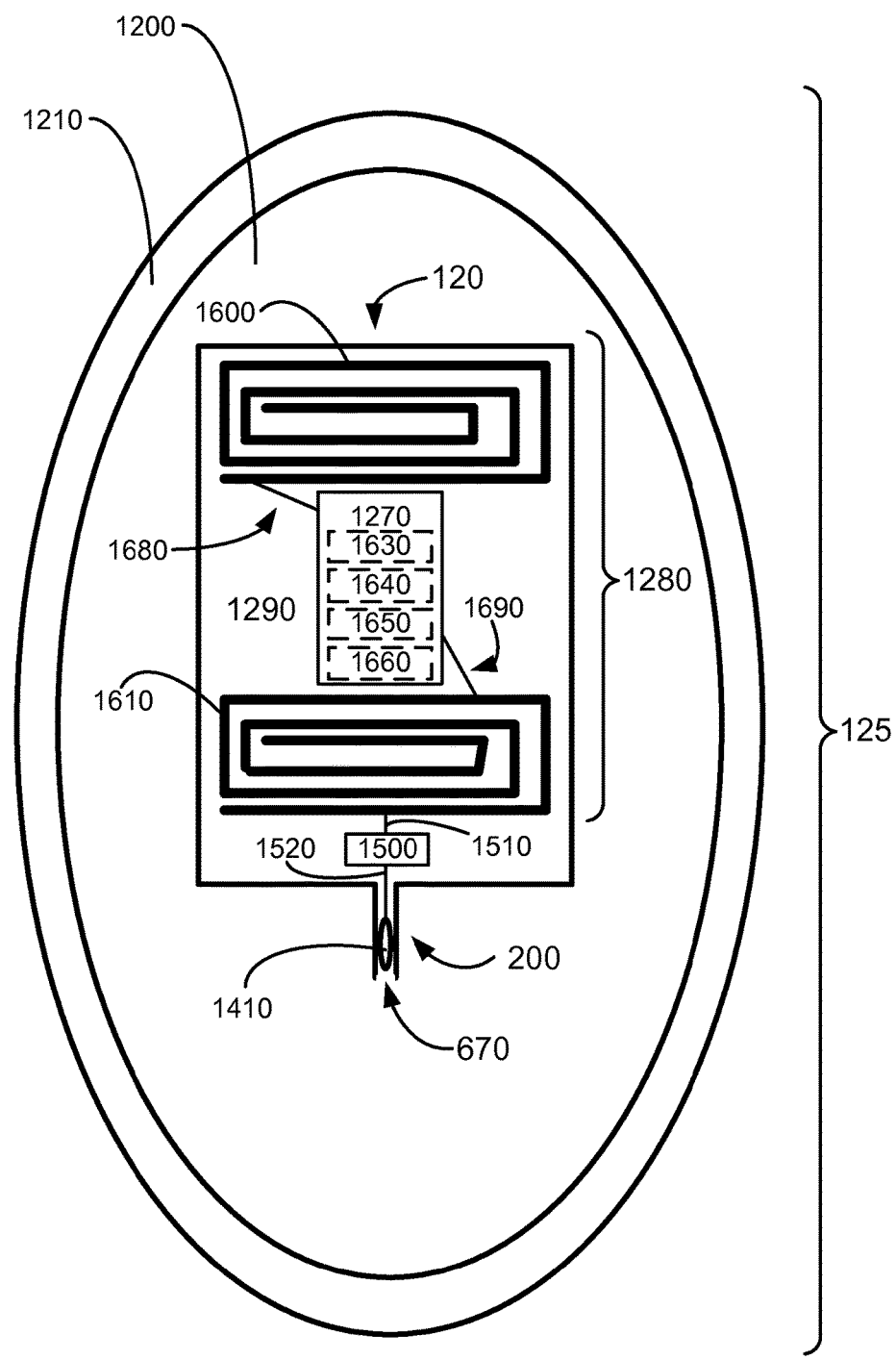
FIG. 16 is a schematic of an appurtenance to a wound dressing.
Figure 17:
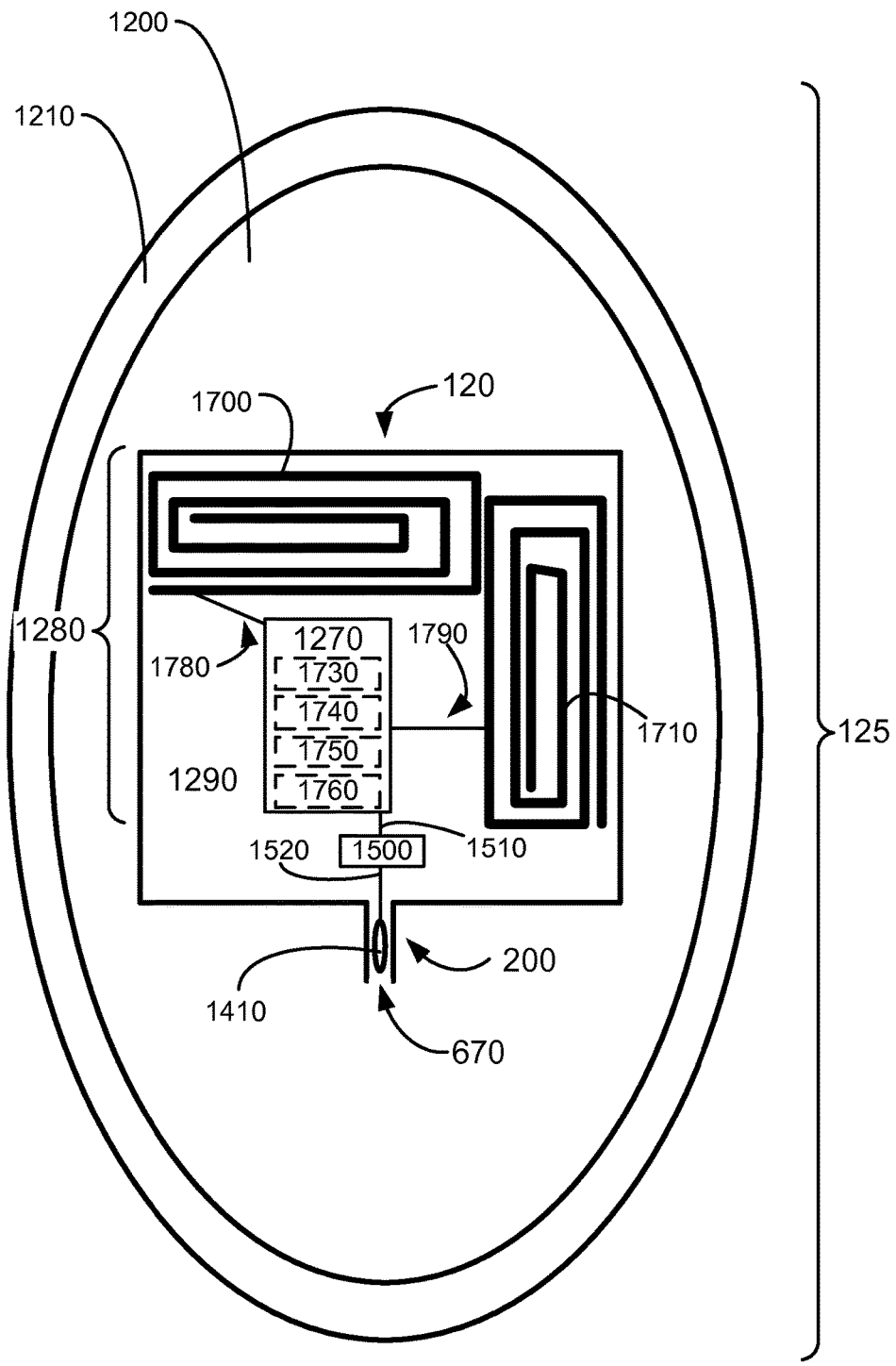
FIG. 17 is a schematic of an appurtenance to a wound dressing.

In some embodiments, the appurtenance 120 includes a second antenna (not illustrated in FIG. 13, but see FIGS. 16 and 17). In a situation where the activity of a first antenna is mitigated by contact with fluid (e.g. as fluid 1310 illustrated in FIG. 13), the second antenna can still retain its original activity and function. For example, an appurtenance with a first antenna and a second antenna can transmit a characteristic signal, such as an identifying signal, from each antenna in the absence of fluid within the appurtenance. In a situation where the first antenna transmits a modulated signal, or no longer transmits signals, due to contact of the antenna to fluid that has flowed from the interior of the wound dressing through the projection to come into contact with the first antenna, the second antenna will still be operational. Therefore, an associated signal reader and/or system (see, e.g. FIGS. 18, 19, 20 and 21) can detect a loss of signal from the first antenna and a maintained signal from the second antenna of an appurtenance. A signal reader and/or system can be programmed to initiate a warning signal to a user when such conditions are detected.

As illustrated in FIGS. 12 and 13, in some embodiments an appurtenance 120 to a wound dressing 1200, 1210 includes: a substrate 1290; a transmission unit 1280 that is a passive RFID unit attached to the substrate 1290; and a substantially hollow projection 200 operably attached to the substrate 1290, the projection 200 including a first end and a second end, the first end of a size and shape to extend within a wound dressing, the second end extending into the passive RFID unit.

Figure 14:
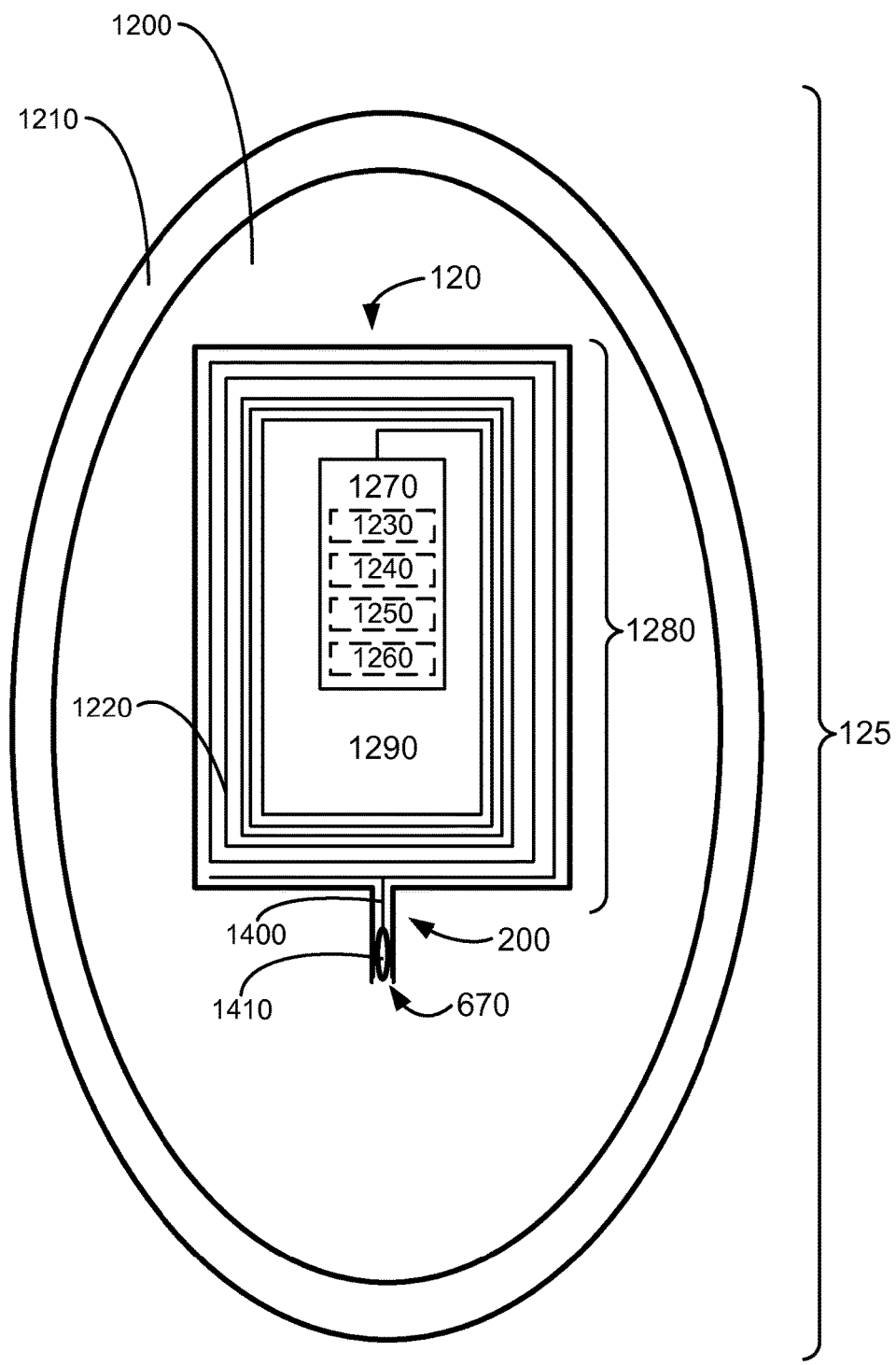
FIG. 14 is a schematic of an appurtenance to a wound dressing.

FIG. 14 illustrates an appurtenance 120 affixed to a wound dressing 1200, 1210 to form a wound dressing-appurtenance combination unit 125. The appurtenance 120 includes a substrate 1290 and a transmission unit 1280 attached to a surface of the substrate 1290. The transmission unit 1280 includes an antenna 1220 and circuitry 1270. The circuitry 1270 of the transmission unit 1280 can include a processor 1230. The circuitry 1270 can include volatile or non-volatile memory 1240. The circuitry 1270 can include a transmitter 1250. The circuitry 1270 can include one or more additional modules 1260. For example, the circuitry 1270 can include an energy source, such as a battery. For example, the circuitry 1270 can include a receiver. For example, the circuitry 1270 can include a transceiver. For example, the circuitry 1270 can include an additional antenna.

The appurtenance 120 includes a projection 200. Although the projection 200 is displayed for the purposes of illustration, when an appurtenance 120 is affixed to a wound dressing to form a wound dressing-appurtenance combination unit 125 in normal use, the projection 200 would extend into an interior region of the wound dressing (see, e.g. FIGS. 2B, 8B, 9B, 10B and 11B), and, therefore, not be visible from a superficial view. The projection 200 includes one or more sensors 1410 and at least one substantially hollow enclosure substantially encircling the one or more sensors 1410, the at least one substantially hollow enclosure including one or more openings 670 within the enclosure distal to the attachment to the substrate. As shown in FIG. 14, a sensor 1410 is within the substantially hollow enclosure of the projection 200, in a region adjacent to the opening 670 in the projection 200. The one or more sensors 1410 can be entirely or partially internal to the projection. A sensor 1410 can be configured to be responsive to a change in capacitance, and be operably connected to the transmission unit 1280. FIG. 14 also illustrates that there is a connector 1400 between the transmission unit 1280 and the one or more sensors 1410. The connector 1400 can be a wire.

Figure 15:
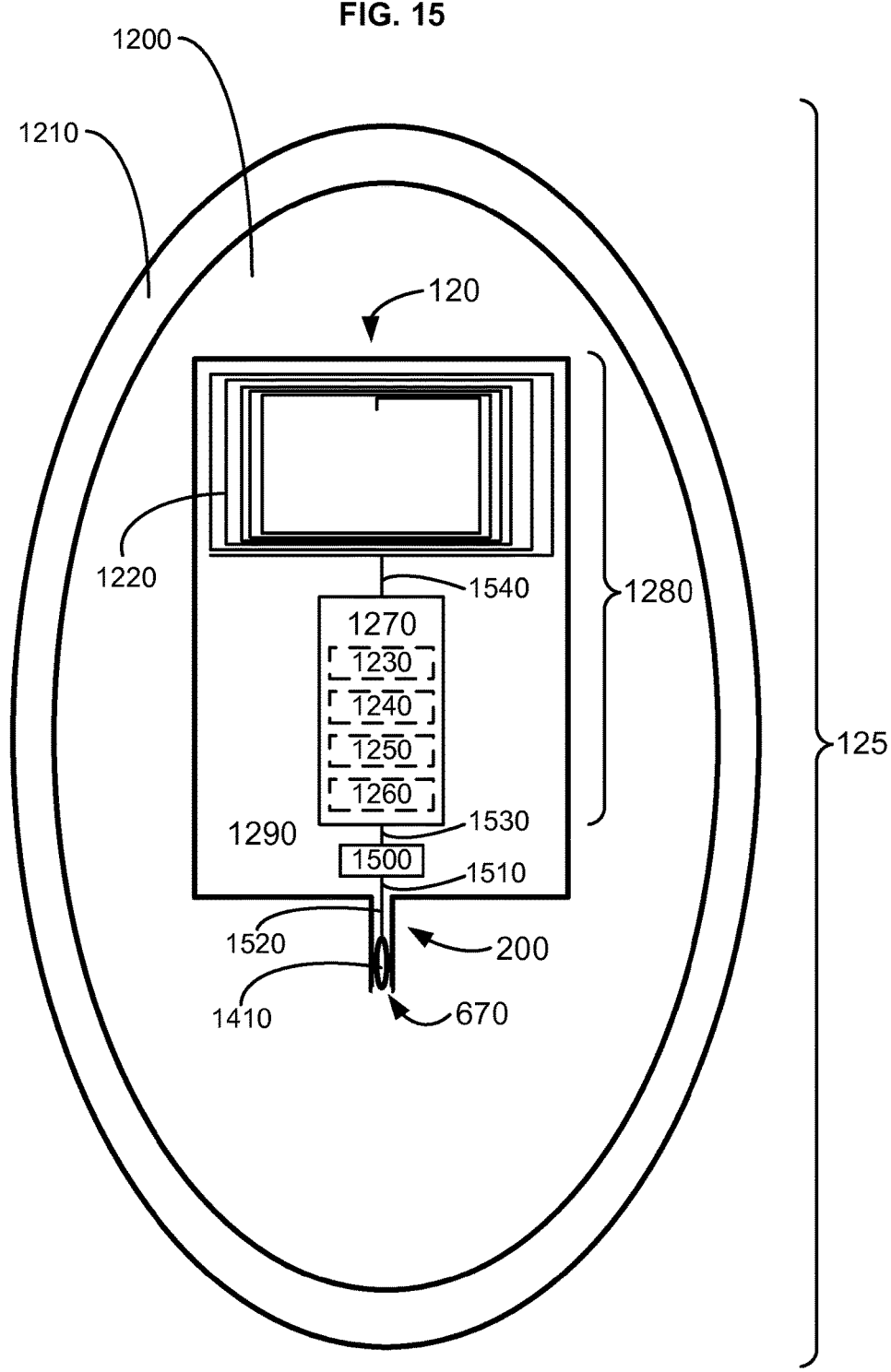
FIG. 15 is a schematic of an appurtenance to a wound dressing.

As illustrated in FIG. 15, some embodiments include a device, including: a wound dressing 1200, 1210; a transmission unit 1280 irreversibly attached to the wound dressing 1200, 1210, the transmission unit 1280 including circuitry 1270 and at least one antenna 1220; a selectively actuatable switch 1500 operably connected to the transmission unit 1280; and a projection 200 operably attached to the switch 1500, the projection 200 extending within an interior region of the wound dressing 1200. Although the projection 200 is visible for purposes of illustration, in actual use a projection 200 attached to an appurtenance 120 affixed as to a wound dressing 1200, 1210 would project within the wound dressing 1200. As illustrated in FIG. 15, the selectively actuatable switch 1500 is operably connected to the transmission unit 1280 with a wire connection 1530. As depicted in FIG. 15, the projection 200 is operably attached to the switch 1500 through a wire connection 1510 between the switch 1500 and a sensor 1410 substantially within the projection 200. FIG. 15 also illustrates that some embodiments include a wound dressing unit 125 includes: a wound dressing 1200, 1210; a substrate 1290 attached to an external surface of the wound dressing 1200, 1210; a transmission unit 1280 attached to a surface of the substrate 1290, the transmission unit 1280 including circuitry 1270 and at least one antenna 1220, the transmission unit 1280 configured to transmit a signal; a selectively actuatable switch 1500 operably connected to the transmission unit 1280; and a projection 200 operably attached to the switch 1500, the projection 200 extending through the external surface of the wound dressing 1200, 1210. Although FIG. 15 is a top-down view, it is intended that the projection 200 is angled away from the surface plane of the wound dressing 1200, 1210 (e.g. as illustrated in FIGS. 2A, 2B, 8A and 8B). As shown in FIG. 15, the projection 200 can include a sensor 1410 operably connected to a selectively actuatable switch 1500 through a wire connection 1520. The sensor 1410 can be configured to actuate the switch in response to a stimulus. The sensor 1410 can be configured to cause a change in the state of the switch in response to a stimulus, such as the presence of an analyte.

A "selectively actuatable switch," as used herein, refers to a switch of sufficient structure to allow or disallow a transmission unit 1280 to transmit a signal in response to a sensor 1410. A selectively actuatable switch includes a switch that can be turned between settings (i.e. "on" and "off") in response to a stimulus. A selectively actuatable switch can, for example, be coupled to a transmission unit 1280 that includes an RFID device. See, for example, U.S. Pat. No. 7,411,505 titled "Switch Status and RFID Tag," which is incorporated herein by reference. A selectively actuatable switch can be a binary switch, or a switch with substantially two settings (i.e. "on" and "off"). A selectively actuatable switch can be configured to be irreversible, or to irreversibly go from one state to a second state. A selectively actuatable switch can be configured to be responsive to a change in capacitance.

FIG. 16 illustrates aspects of an appurtenance 120 to a wound dressing 1200, 1210. The appurtenance 120 is irreversibly attached to a wound covering 1200 portion of a wound dressing. The appurtenance 120 includes a substrate 1290 and a projection 200 attached to the substrate 1290. As shown in FIG. 16, there is a transmission unit 1280 attached to the substrate 1290. The transmission unit 1280 includes a first antenna 1600, a second antenna 1610 and circuitry 1270 operably connected to both the first antenna 1600 and the second antenna 1610. The circuitry 1270 is operably connected to the first antenna 1600 with a wire connection 1680. The circuitry 1270 is operably connected to the second antenna 1610 with a wire connection 1690. The circuitry 1270 of the transmission unit 1280 can include a variety of components, as desired in a particular embodiment. The circuitry 1270 of the transmission unit 1280 can include a processor 1630. The circuitry 1270 can include non-volatile memory 1640. The circuitry 1270 can include a transmitter 1650. The circuitry 1270 can include one or more additional modules 1660. For example, the circuitry 1270 can include an energy source, such as a battery. For example, the circuitry 1270 can include a receiver. For example, the circuitry 1270 can include a transceiver. For example, the circuitry 1270 can include volatile memory. For example, the circuitry 1270 can include an additional antenna. The circuitry 1270 can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference.

The embodiment illustrated in FIG. 16 includes a projection 200 attached on one end to the substrate 1290, and the other end including an opening 670. The projection includes a sensor 1410 within the substantially hollow projection 200. In an actual appurtenance-wound dressing combination unit 125, the projection 200 would extend into the wound dressing 1200, however for the purposes of illustration the projection 200 is made visible in FIG. 16. The sensor 1410 is operably attached to a selectively actuatable switch 1500 with a wire 1520. The selectively actuatable switch 1500 is operably attached to the first antenna 1610 with a wire 1510.

FIG. 17 shows aspects of an appurtenance 120 to a wound dressing 1200, 1210. The appurtenance 120 is irreversibly attached to a wound covering 1200 portion of a wound dressing. The appurtenance 120 includes a substrate 1290 and a projection 200 attached to the substrate 1290. As shown in FIG. 17, there is a transmission unit 1280 attached to the substrate 1290. The transmission unit 1280 includes a first antenna 1700, a second antenna 1710 and circuitry 1270 operably connected to both the first antenna 1700 and the second antenna 1710. The circuitry 1270 is operably connected to the first antenna 1700 with a wire connection 1780. The circuitry 1270 is operably connected to the second antenna 1710 with a wire connection 1790. The circuitry 1270 of the transmission unit 1280 can include a variety of components, as desired in a particular embodiment. The circuitry 1270 of the transmission unit 1280 can include a processor 1730. The circuitry 1270 can include non-volatile memory 1740. The circuitry 1270 can include a transmitter 1750. The circuitry 1270 can include one or more additional modules 1760. For example, the circuitry 1270 can include an energy source, such as a battery. For example, the circuitry 1270 can include a receiver. For example, the circuitry 1270 can include a transceiver. For example, the circuitry 1270 can include an additional antenna. The circuitry 1270 can include dielectric material configured to electrically interact with one or more antennas. See, for example, U.S. Pat. No. 7,055,754 to Forester, titled "Self-Compensating Antennas for Substrates Having Differing Dielectric Constant Values," which is incorporated herein by reference.

The embodiment shown in FIG. 17 includes a projection 200 attached on one end to the substrate 1290, and the other end including an opening 670. The projection includes a sensor 1410 within the substantially hollow projection 200. In an actual appurtenance-wound dressing unit 125, the projection 200 would extend into the wound dressing 1200, however for the purposes of illustration the projection 200 is made visible in FIG. 17. The sensor 1410 is operably attached to a selectively actuatable switch 1500 with a wire connection 1520. The selectively actuatable switch 1500 is operably attached to the circuitry with a wire connection 1510.

Figure 18:
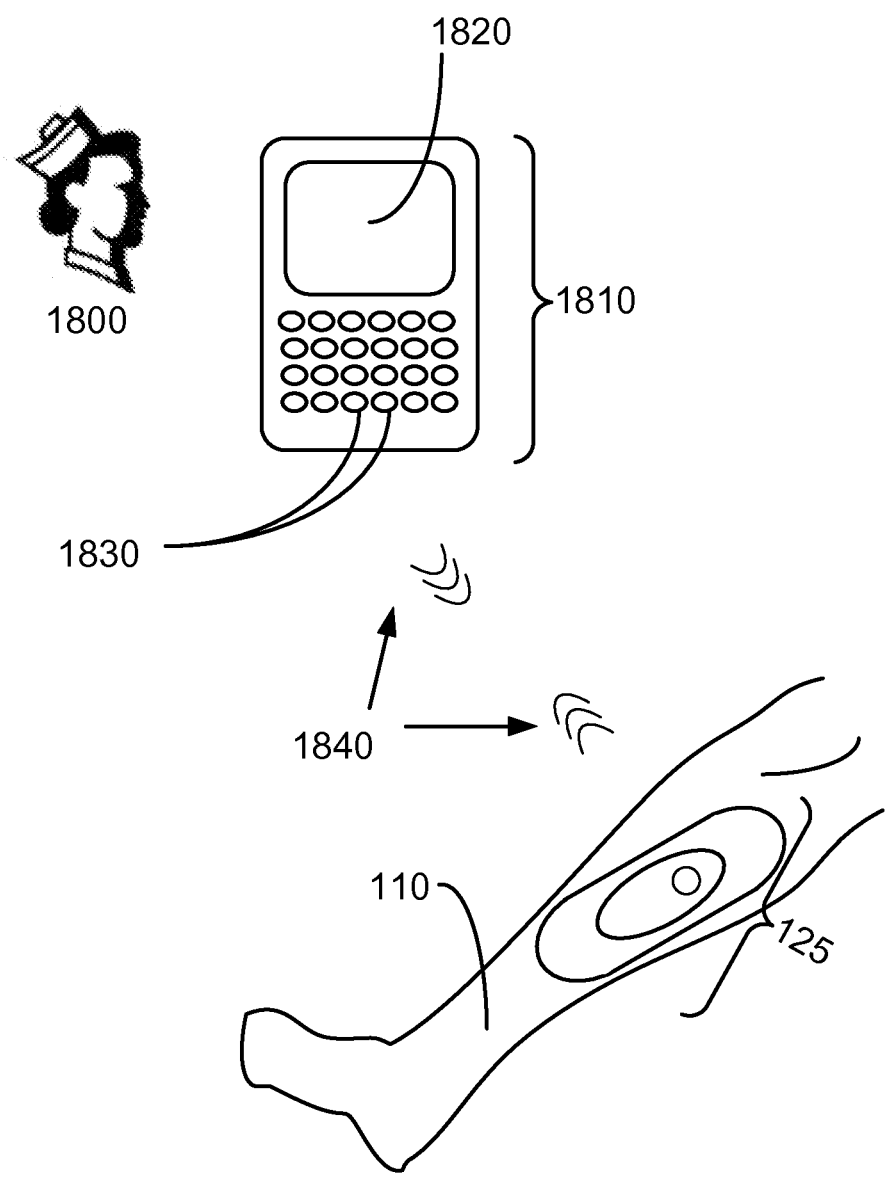
FIG. 18 is a schematic of an appurtenance to a wound dressing in communication with a local unit.

FIG. 18 illustrates aspects of a system including a wound dressing with an affixed appurtenance combination unit 125. As shown in FIG. 18, a wound dressing with an affixed appurtenance combination unit 125 is placed over a wound on a body part 110 of a patient. For example, the body part 110 can have been subject to a surgery, and therefore to have an acute wound. For example, the body part 110 can include an ulcer, and therefore have a chronic wound. The wound dressing with an affixed appurtenance combination unit 125 receives signals 1840 from a local unit 1810 and transmits signals 1840 to the local unit 1810. For example, the wound dressing with an affixed appurtenance combination unit 125 can include a passive RFID configured to transmit signals 1840 after receiving signals 1840 from a proximal RFID reader device in the local unit 1810.

A local unit 1810 can include a handheld device. For example, the local unit 1810 can include a distinct handheld device. For example, the local unit 1810 can be included as part of a larger handheld unit, for example a tablet, a laptop, a cell phone, a personal communication device, or similar types of devices. A local unit 1810 can be configured to be attached to a location, such as the end of a hospital bed, a medical stand, a bedside table, a wheelchair, or similar device. A local unit 1810 can be configured to be integrated into a piece of mobile equipment, such as the end of a hospital bed, a medical stand, a wheelchair, or similar device. For example, a local unit can be integrated with a medical cart, as described in U.S. Pat. No. 7,667,606 to Packert et al., titled "RF Enabled Surgical Cart and Use of Same in Operating Room Environment," which is incorporated herein by reference. A local unit 1810 can be configured to be integrated into a furnishing. For example, a local unit 1810 can be integrated into a hospital bed, a bedside hospital monitor, a bedside table, a medical chair, a medical table, or similar furnishing. A local unit 1810 can include a display unit 1820. In some embodiments, there can be a secondary device configured to relay signals from a wound dressing with an affixed appurtenance combination unit 125 to the local unit 1810, for example as described in U.S. Pat. No. 7,986,235 to Posamentier titled "RFID Receive-Only System," which is incorporated herein by reference. For example, a secondary device configured to relay signals from a wound dressing with an affixed appurtenance combination unit 125 to the local unit 1810 can be configured to increase the signal strength to a local unit 1810 positioned a distance away from the wound dressing with an affixed appurtenance combination unit 125. For example, a secondary device configured to relay signals from a wound dressing with an affixed appurtenance combination unit 125 to the local unit 1810 can be configured to relay signals from a plurality of wound dressings with affixed appurtenance units 125 to a single local unit 1810. A local unit 1810 can include an input device 1830, for example a keyboard. Although the local unit 1810 illustrated in FIG. 18 includes a keyboard as an input device 1830, in some embodiments the input device 1830 can include other types of input devices, for example a touchscreen, stylus, keypad, or voice recognition system. A user 1800, such as a medical caregiver, operates the local unit 1810.

A user 1800 can include a medical caregiver, such as a nurse or doctor, or a patient or other individual monitoring the wound dressing. Although user 1800 is shown/described herein as a single illustrated figure, those skilled in the art will appreciate that user 1800 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise. A user 1800 can utilize a local unit 1810 through a user interface, for example one or more buttons, a keyboard, a touchscreen, a voice recognition device, a stylus, or other means.

A local unit 1810 can be configured to send signals to one or more wound dressings with attached appurtenances 125 automatically. For example, local unit 1810 can be configured to send signals to one or more wound dressings with attached appurtenances 125 at least one of: every 10 minutes; every 20 minutes; every 30 minutes; every hour; every 2 hours; or every 3 hours. A local unit 1810 can be configured to send signals to one or more wound dressings with attached appurtenances 125 on a schedule selected by the user 1800. For example, local unit 1810 can be configured to send signals to one or more wound dressings with attached appurtenances 125 on at least one of: an hourly schedule; a schedule of every 30 minutes for 4 hours, followed by hourly signals; a schedule of every 10 minutes for 6 hours, followed by signals every 30 minutes; or a schedule provided by the user through the user interface (e.g. the keyboard 1830). A local unit 1810 can be configured to send signals to one or more wound dressings with attached appurtenance combination units 125 on a preset schedule which is selected by the user 1800. For example, local unit 1810 can be configured to send signals to one or more wound dressings with attached appurtenance combination units 125 on at least one of: a schedule preset to monitor a wound after surgery; a schedule preset to monitor a chronic wound; an hourly schedule; a schedule of every 2 hours; a schedule of hourly during the day and every 2 hours at night; or other preset schedules.

The signals 1840 sent from the local unit 1810 to the wound dressing with attached appurtenance combination unit 125 can be radio frequency signals in a particular wavelength, or range of wavelengths. For example, the signals can be in the UHF range, such as a UHF sub-range commonly used in a particular geographic region. See, for example the "Worldwide RFID UHF Map" by Intelleflex Corporation (©2009), which is incorporated herein by reference. For example, the signals can be in a range specified by an industry standard. For example, the signals can be in the approximately 13.56 megahertz (MHz) range, or within the ISO 14443 standard parameters. For example, the signals can be in the IEEE 802.11x standard or the Bluetooth standard range. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. For example, the signals can be in the approximately 131 kilohertz (KHz) range, for example as part of a RuBee™ (IEEE standard 1902.1) system (i.e. equipment sold by Visible Assets™, Inc.). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference.

Similarly, the signals 1840 sent from the wound dressing with attached appurtenance unit 125 to the local unit 1810 can be one of the types described above in relation to signals 1840 sent from the local unit 1810. In some embodiments, the wound dressing with attached appurtenance unit 125 includes a backscatter or reflective transmission device, and so the signals 1840 sent from the wound dressing with attached appurtenance unit 125 to the local unit 1810 can be backscatter or reflective signals. For example, as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference.

The signals 1840 transmitted from the local unit 1810 or transmitted from the wound dressing with attached appurtenance combination unit 125 can be sent in a fixed direction from the signal source. The wound dressing with attached appurtenance combination unit 125 and the local unit 1810 can each include markings or other visible aspects directing a user how as to orient the wound dressing with attached appurtenance combination unit 125 and the local unit 1810 relative to each other for signal directionality.

In many embodiments, it is envisioned that the signal strength of a signal 1840 transmitted from either the local unit 1810 or transmitted from the wound dressing with attached appurtenance combination unit 125 will be such that the signal 1840 will not travel a significant distance. The local unit 1810 and the wound dressing with attached appurtenance combination unit 125 can, therefore, need to be placed in reasonably close proximity for signals 1840 to travel between the devices. For example, the signal 1840 transmitted from either the local unit 1810 or transmitted from the wound dressing with attached appurtenance combination unit 125 can be such that the receiver of such signals should be within the same room. For example, the signal 1840 transmitted from either the local unit 1810 or transmitted from the wound dressing with attached appurtenance combination unit 125 can be such that the receiver of such signals should be within 10 feet. For example, the signal 1840 transmitted from either the local unit 1810 or transmitted from the wound dressing with attached appurtenance combination unit 125 can be such that the receiver of such signals should be within 3 feet.

Figure 19:
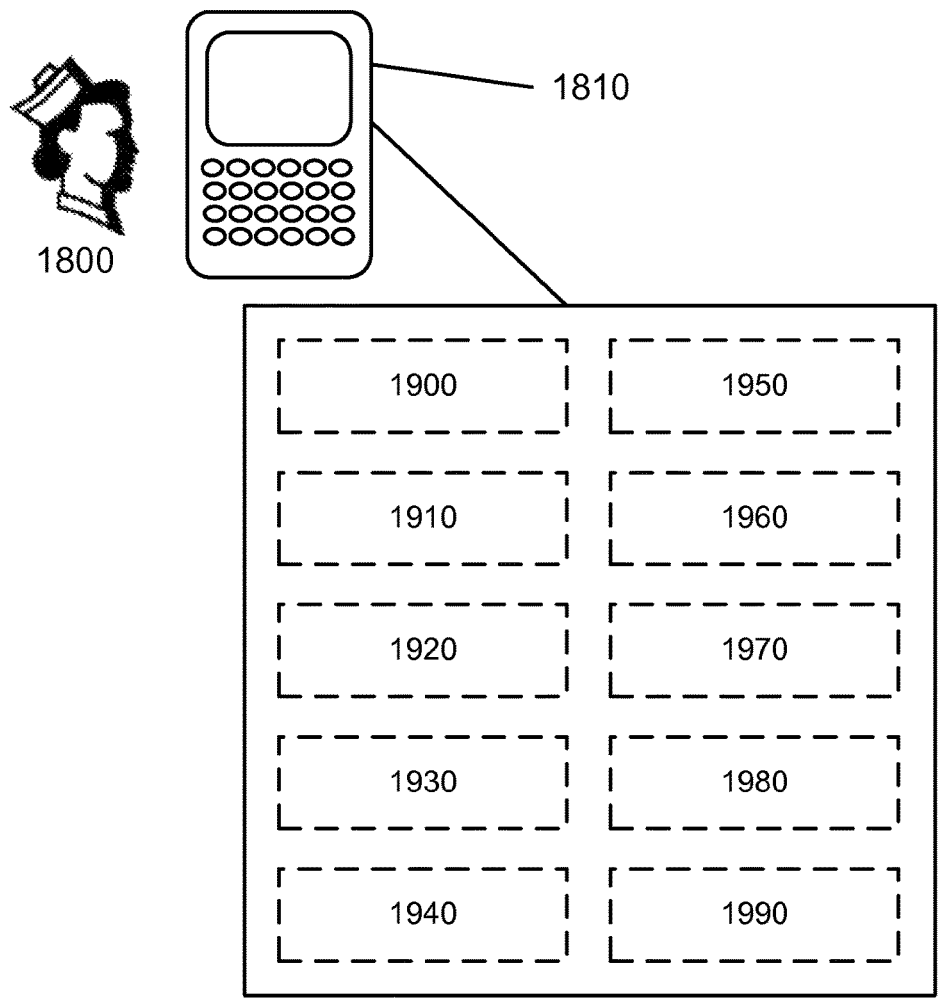
FIG. 19 is a schematic of an appurtenance to a wound dressing in communication with a local unit.
Figure 19:
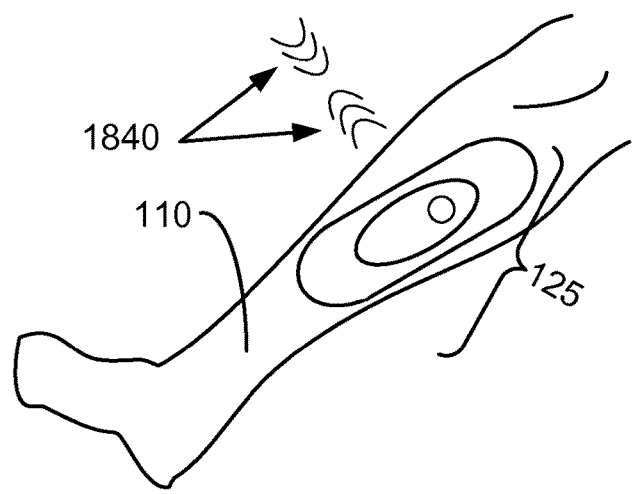

FIG. 19 illustrates aspects of a system including a wound dressing with an affixed appurtenance combination unit 125. As illustrated in FIG. 19, a wound dressing with an affixed appurtenance combination unit 125 is placed over a wound on a body part 110 of a patient. The wound dressing with an affixed appurtenance combination unit 125 sends and receives signals 1840 from a local unit 1810. The local unit 1810 can be utilized by a user 1800.

FIG. 19 illustrates aspects of the local unit 1810. The local unit 1810 includes a housing, with connected user interface and input components (e.g. a display and keyboard). The local unit 1810 can include a processor 1800. The local unit 1810 can include memory 1910. The memory 1910 can include, for example, non-volatile memory. The memory 1910 can include, for example, volatile memory. The local unit 1810 can include at least one antenna 1920. The local unit 1810 can include circuitry 1930, operably connected to the other components of the local unit 1810. The local unit 1810 can include one or more transmitters 1940. The local unit 1810 can include one or more receivers 1950. The local unit 1810 can include one or more power sources 1960, such as a battery, a solar cell, or a plug-in socket. The local unit 1810 can include logic 1970. The local unit 1810 can include other components 1980, 1990 as appropriate to a specific embodiment. The local unit 1810 can include, for example, an application specific intelligent microsensor as described in U.S. Pat. No. 6,889,165 to Lind et al., titled "Application Specific Intelligent Microsensors," which is incorporated herein by reference. The local unit 1810 can include, for example, a distinct identification signal. The local unit 1810 can include, for example, a visible indicator, such as a light. The local unit 1810 can include, for example, an identification code specific to that local unit 1810.

Figure 20:
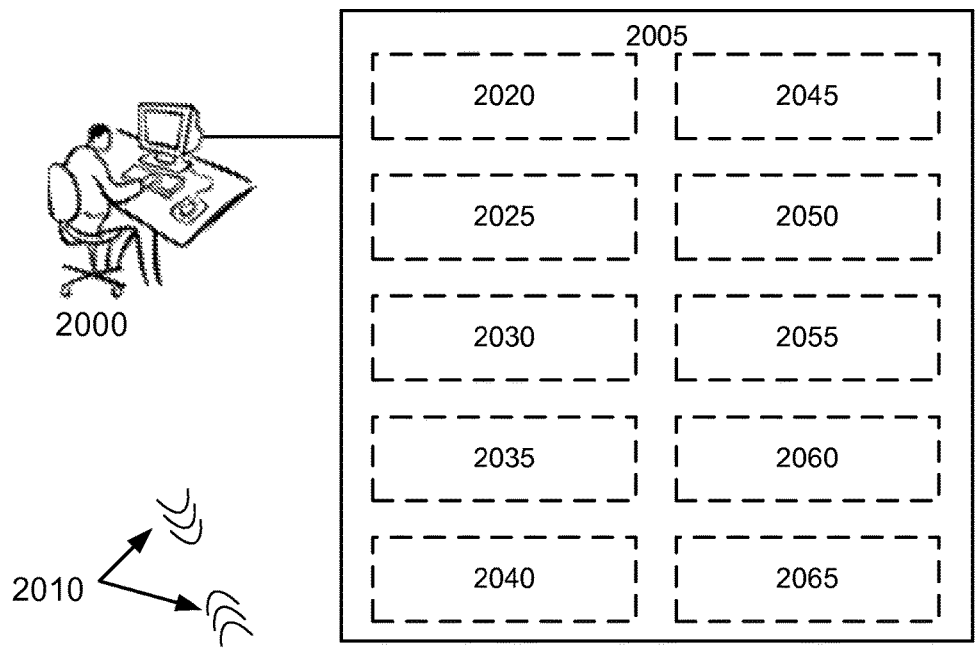
FIG. 20 is a schematic of an appurtenance to a wound dressing in communication with a local unit and a central assembly.
Figure 20:
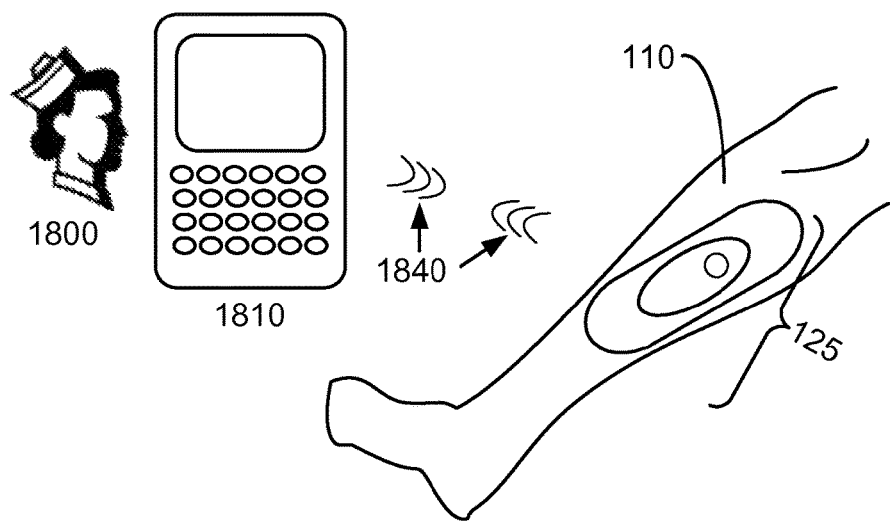

FIG. 20 shows aspects of a system including a wound dressing with an affixed appurtenance combination unit 125. As shown in FIG. 20, a wound dressing with an affixed appurtenance combination unit 125 is placed over a wound on a body part 110 of a patient. The wound dressing with an affixed appurtenance combination unit 125 sends and receives signals 1840 from a local unit 1810. The local unit 1810 can be utilized by a user 1800.

Also as shown in FIG. 20, the local unit 1810 can send and receive signals 2010 from a central assembly 2005. The local unit 1810 can send and receive signals 2010 with a wireless connection, as shown in FIG. 20, or can send and receive signals 2010 through a wire connection. A central assembly 2005 includes at least one user interface device (e.g. a keyboard, touchscreen, display, etc.) which can be utilized by a system user 2000. A system user 2000 can include a medical caregiver, such as a nurse or doctor, or a patient caregiver, or other individual monitoring the wound dressing. Although system user 2000 is shown/described herein as a single illustrated figure, those skilled in the art will appreciate that system user 2000 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise.

FIG. 20 illustrates aspects of some embodiments of a central assembly 2005. A central assembly can be located primarily or mainly in one or a limited number of machines, for example one or more computer servers. A central assembly 2005 can interface with, or include, a 2G-RFID-Based E-Healthcare system. See, for example, Chen et al., "A 2G-RFID-Based E-Healthcare System," *IEEE Wireless Communications*, February 2010, pages 37-43, which is incorporated herein by reference. A central assembly 2005 can interface with, or include, a digital management system, for example as discussed in: Fisher, "Indoor Positioning and Digital Management Emerging Surveillance Regimes in Hospitals" in T. Monahan (Ed), Surveillance and Security: Technological Politics and Power in Everyday Life (pp. 77-88), New York: Routledge (2006); and Fisher and Monahan, "Tracking the Social Dimensions of RFID Systems in Hospitals," *International Journal of Medical Informatics* 77 (2008) 176-183, which are each incorporated herein by reference. A central assembly 2005 can interface with, or include, a drug tracking system, as described, for example, in "RFID Systems for Pharmaceutical Distributors to Meet the New FDA Regulations on Drugs," white paper from Abhisam Software, 2006, which is incorporated herein by reference. The central assembly 2005 can include, for example, at least one transmitter 2020. The central assembly 2005 can include, for example, at least one receiver 2025. The central assembly 2005 can include, for example, at least one antenna 2030. The central assembly 2005 can include, for example, memory, which can include non-volatile memory or volatile memory. The central assembly 2005 can include, for example, circuitry 2040. The circuitry 2040 can be operably connected to other components of the central assembly 2005. The central assembly 2005 can include, for example, a power source 2045. A power source 2045 can include, for example, at least one battery, a plug-in connection, a wireless power source, or a solar cell. The central assembly 2005 can include, for example, a processor 2050. The central assembly 2005 can include, for example, logic 2055. The central assembly 2005 can include, for example, additional components 2060, 2065.

Figure 21:
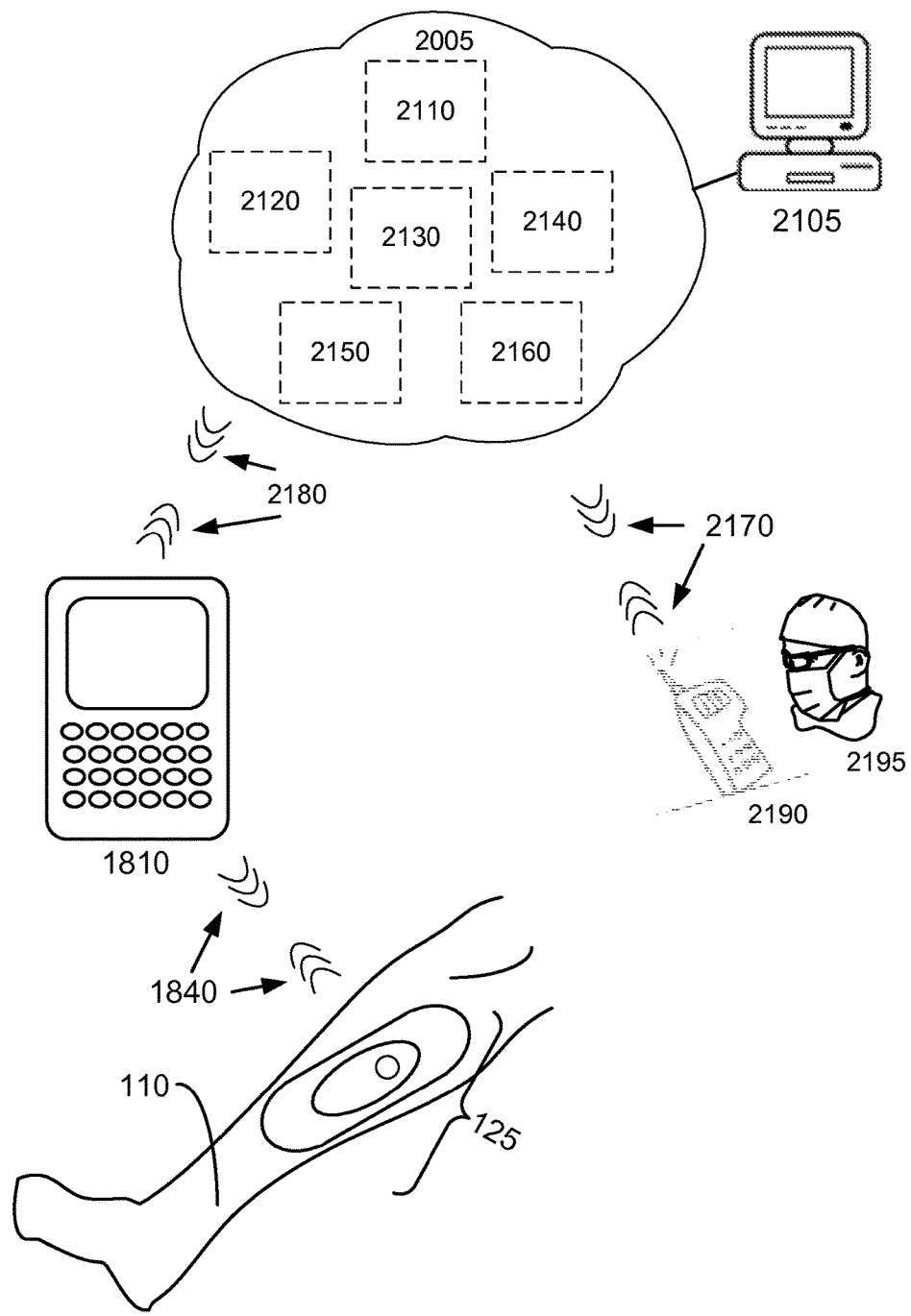
FIG. 21 is a schematic of an appurtenance to a wound dressing in communication with a local unit, a central assembly and a remote device.

FIG. 21 illustrates aspects of a system including a wound dressing with an affixed appurtenance combination unit 125. As illustrated in FIG. 21, a wound dressing with an affixed appurtenance combination unit 125 is placed over a wound on a body part 110 of a patient. The wound dressing with an affixed appurtenance combination unit 125 sends and receives signals 1840 from a local unit 1810. The local unit 1810 sends and receives signals 2180 from a central assembly 2005. The central assembly 2005 illustrated in FIG. 21 is in a "cloud" format, with a significant portion of its components distributed on a computer network, or a network of computing devices. The central assembly 2005 is configured to communicate with one or more interface devices 2105, for example an individual computer.

Depending on the embodiment, a cloud-based central assembly 2005 can include a plurality of components as illustrated in FIG. 21. For example, a central assembly 2005 can include logic 2110. For example, a central assembly 2005 can include circuitry 2120. The circuitry 2120 can be operably connected to other components of the central assembly 2005. For example, a central assembly 2005 can include memory 2130. For example, a central assembly 2005 can include one or more power sources 2140. For example, a central assembly 2005 can include at least one processor 2150. For example, a central assembly 2005 can include other components 2160.

Also as illustrated in FIG. 21, a central assembly 2005 can communicate with a remote device 2190 through signals 2070. Signals 2070 can be sent and received by an aspect of the central assembly 2005. Signals 2070 can be sent and received by the remote device 2190. Although the signals 2070 illustrated in FIG. 21 are wireless signals, in some embodiments the central assembly 2005 and a remote device 2190 can communicate through a wired connection. The remote device 2190 can be, for example, a pager, cell phone, laptop, PDA, tablet, smart phone or other device. The remote device 2195 can be operated by a remote system user 2095. Some embodiments include a plurality of remote devices 2190, which can be operated by a plurality of remote system users 2195.

Some embodiments include a device for attaching an appurtenance to a wound dressing. Although in some embodiments, the appurtenance can be configured to be attached to a wound dressing without an additional device (e.g. with the pressure of a human finger or hand alone), in some embodiments a specific device for attaching an appurtenance to a wound dressing can be useful to ensure that the appurtenance is securely affixed to the wound dressing and/or to ensure positioning of the appurtenance relative to the wound dressing. A specific device for attaching an appurtenance to a wound dressing can be useful to minimize contamination of a clean or substantially sterile appurtenance. The device for attaching an appurtenance to a wound dressing can include: a base plate; a handle attached to the base plate; a holder region configured to hold an appurtenance to a wound dressing during attachment to a wound dressing; a handle attached to the holder region; and a pivot between the handle attached to the base plate and the handle attached to the holder region. For example, the device for attaching an appurtenance to a wound dressing can include a substantially planar base plate configured to position under the wound dressing during attachment. For example, a device for attaching an appurtenance to a wound dressing can be a pincer-like device, with two relative rotating arms that bring the appurtenance within the holder region down on the wound dressing on the base plate during attachment of the appurtenance to a wound dressing.

In some embodiments, the base plate of the device for attaching an appurtenance to a wound dressing includes: a substantially planar surface of a size and shape substantially corresponding to a substantially planar surface of the appurtenance; and a concavity within the substantially planar surface of the base plate, the concavity substantially corresponding to the height and cross-section of the appurtenance. This type of base plate can be particularly useful, for example, in embodiments wherein the appurtenance is of a size and shape that is of a size and shape difficult to grip with a normally-sized human hand. For example, an appurtenance can be too small for easy handling with a normally-sized adult human hand.

In some embodiments, the handle attached to the base plate of the device for attaching an appurtenance to a wound dressing includes: a handle of a size and shape configured for use by an adult human hand. In some embodiments, the handle attached to the base plate of the device for attaching an appurtenance to a wound dressing includes: a substantially linear handle attached at a less than 45 degree angle relative to the base plate. For example, the handle can be substantially linear but the attachment to the base plate at an end of the handle can be positioned at an angle less than a 45 degree angle relative to the substantial planes of the handle and the base plate.

In some embodiments, the holder region includes: a flange of a size and shape to retain a region of an appurtenance to a wound dressing adjacent to a surface of a wound dressing during attachment. For example, the flange region can be configured to improve stability of the appurtenance during attachment. In some embodiments, the holder region includes: a clamp of a size and shape corresponding to region of an appurtenance to a wound dressing. For example, the clamp can be positioned to orient the appurtenance during attachment.

In some embodiments, the handle attached to the holder region includes: a handle of a size and shape configured for use by an adult human hand. In some embodiments, the handle attached to the holder region includes: a substantially linear handle attached at a less than 45 degree angle relative to the holder region.

In some embodiments, the handle attached to the base plate and the handle attached to the holder region are of a substantially similar size and shape. For example, both of the handles can be of a size and shape configured for use by an adult human hand.

In some embodiments, the pivot between the handle attached to the base plate and the handle attached to the holder region includes: a rod traversing a cross-section of each of the handle attached to the base plate and the handle attached to the holder region when the respective handles are positioned adjacent to each other. For example, the rod can be positioned to orient and attach the handles relative to each other.

Some embodiments include a method of attaching an appurtenance to a wound dressing. Methods of attaching an appurtenance to a wound dressing can include the steps of: placing an appurtenance for a wound dressing in contact with an outer surface of the wound dressing; and providing pressure on the appurtenance sufficient to force a section of the appurtenance through the outer surface of the wound dressing and into an interior region of the wound dressing. In some embodiments, the placing an appurtenance for a wound dressing in contact with an outer surface of the wound dressing includes: removing an external cover of the wound dressing; and placing the appurtenance in contact with a superficial surface of the wound dressing.

In some embodiments, the providing pressure on the appurtenance includes providing manual pressure. In some embodiments, the providing pressure on the appurtenance includes providing pressure in a direction substantially perpendicular to the outer surface of the wound dressing. In some embodiments, the providing pressure on the appurtenance includes providing pressure in a direction substantially at an angle to the outer surface of the wound dressing.

Methods of attaching an appurtenance to a wound dressing can include the step of removing an external cover of the wound dressing from the outer surface of the wound dressing prior to placing the appurtenance in contact with the outer surface of the wound dressing. Methods of attaching an appurtenance to a wound dressing can include the step of sealing a region including an edge of the appurtenance and the area of the wound dressing adjacent to the edge of the appurtenance with a cover. Methods of attaching an appurtenance to a wound dressing can include the step of sealing a region including an edge of the appurtenance and the area of the wound dressing adjacent to the edge of the appurtenance by forcing one or more projections on the edge of the appurtenance into the outer surface of the wound dressing.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. Optical aspects of implementations will typically employ optically-oriented hardware, software, and or firmware.

In some implementations described herein, logic and similar implementations can include software or other control structures. Electronic circuitry, for example, can have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations can include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, implementations can be provided, in whole or in part, by source code, such as C++, or other code sequences. In other implementations, source or other code implementation, using commercially available and/or techniques in the art, can be compiled//implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) can be manifested as a Verilog-type hardware description (e.g., via Hardware Description Language (HDL) and/or Very High Speed Integrated Circuit Hardware Descriptor Language (VHDL)) or other circuitry model which can then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various embodiments described herein can be implemented, individually and/or collectively, by various types of electro-mechanical systems having a wide range of electrical components such as hardware, software, firmware, and/or virtually any combination thereof; and a wide range of components that can impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context can dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

The herein described components (e.g., operations), devices, objects, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific example is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the recited operations therein can generally be performed in any order. Also, although various operational flows are presented in a sequence(s), it should be understood that the various operations can be performed in other orders than those which are illustrated, or can be performed concurrently. Examples of such alternate orderings can include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

EXAMPLES

Example 1. An Appurtenance to a Wound Dressing Configured to Detect and Report Fluid in a Wound Dressing An appurtenance to a wound dressing is constructed from a flexible thin plastic substrate that is configured in a substantially planar shape. A passive RFID antenna is attached to a surface of the substrate with epoxy. Circuitry for the RFID is attached to the substrate with adhesive and connected to the antenna with conductive ink (e.g., polymer with flecks of silver) as needed to create an operational RFID. Also a port for a polyester tube with approximately 0.5 mm inside diameter is mounted in contact with the antenna with epoxy (see FIG. 12). The polyester tube projects away from the surface of the substrate for approximately 4 millimeters (mm). Encapsulating epoxy material is used to cover the RFID circuit, the conductive ink, conductive epoxy and exterior of the tube port. A space is maintained around the edge of the polyester tube adjacent to the antenna under the encapsulating epoxy material. The space is configured to allow fluid to flow from the tube into contact with the surface of the antenna. The space is approximately 1 mm high and of sufficient lateral dimensions to cover a region of the antenna (e.g. 2-3 mm across). Methods and circuitry to construct passive RFID tags are described (see e.g., U.S. Pat. No. 7,479,886 issued to Burr, titled "Antenna Capacitance for Energy Storage" and Chawla, "An Overview of Passive RFID," *IEEE Applications & Practice*, 11-17, (September 2007), which are each incorporated herein by reference).

The substrate of the appurtenance is attached to the outer surface of a wound dressing with adhesive. A styrene copolymer pressure-sensitive adhesive can be used. In addition, the distal end of the polyester tube is pressed into the layers of the wound dressing with finger-tip pressure (see FIG. 2B). The wound dressing is of sufficient thickness so as to maintain the end of the polyester tube within the layers of the wound dressing, allowing for both the length of the tube itself and the angle it projects from the substrate. For example, if the tube is 4 mm long, the wound dressing can be 6 mm thick, or greater. For example, if the tube is 4 mm long, the wound dressing can be 4 mm thick if the tube is placed at a sufficient angle to maintain the distal end of the tube within the wound dressing. The wound dressing with the appurtenance is placed immediately over the wound and the RFID identity number, patient information, the time and date are entered into a central computer system after interrogating the RFID tag with a RFID reader in a local unit and accessing the patient's electronic medical record. If the patient is wearing an RFID identification device (such as a wristband with an embedded RFID), the patient information can be input into the system by scanning the identification device in association with scanning the appurtenance.

A RFID reader in a local unit proximal to the patient (e.g., on the edge patient's hospital bed or on a bedside table) is used to periodically interrogate the appurtenance on the wound dressing by transmitting a signal in the UHF range (e.g. 902-928 MHz). The local unit can be set to interrogate the appurtenance on a regular schedule, for example every 5 minutes, every 10 minutes, or every half hour. The local unit can also be set to interrogate the appurtenance on command by a user, such as a nurse, orderly, or other caregiver. The appurtenance receives the incident UHF waves and harvests energy to activate the RFID circuitry and transmit a backscatter signal to the RFID reader. The signal encodes the identity of the RFID device and the signal reflects the status of the antenna. If moisture present in the wound dressing reaches levels sufficient for fluid to flow from the wound dressing into the tube of the appurtenance and into contact with the RFID antenna of the appurtenance (e.g. as illustrated in FIG. 13), contact with the fluid on the antenna will modulate function of the antenna. This modulation, which can be a complete loss of function or a reduction or alteration of the "dry" signal, provides a notice to the system that the wound dressing should be checked by a medical caregiver. Excess moisture to the level of fluid flow into the appurtenance can be caused, by example, from the patient bleeding at the wound site, or excess wound exudates.

The RFID reader in the local unit receives signals from the appurtenance RFID device and transmits signals to a central computer that convey: the patient identity, time, date, and moisture status of the wound dressing. The central computer can notify caregivers, for example through a message sent to the nursing station, if the antenna signal from the appurtenance is modulated in a subsequent query, or series of queries. The local unit can also indicate to a healthcare worker the need to change a wound dressing based on the elapsed time since the wound dressing was applied (i.e. when the appurtenance was first "read" into the system).

Example 2. An Appurtenance to a Wound Dressing Configured to Detect and Report Fluid Directly from the Wound or Wound Bed An appurtenance to a wound dressing is constructed substantially similarly as described in Example 1, above. However, the wound dressing is of sufficient thickness so as to allow the end of the polyester tube to protrude through the layers of the wound dressing, allowing for both the length of the tube itself and the angle it projects from the substrate. For example, if the tube is 6 mm long, the wound dressing can be 4 mm thick, depending on the angle of the tube projection through the wound dressing. For example, if the tube is 4 mm long, the wound dressing can be 4 mm thick if the tube is placed at a sufficient angle to allow the distal end of the tube to be at the surface of, or protrude from, the wound dressing. The polyester tube should not protrude from the wound dressing in a manner to create a new injury or puncture in the wound or body part. In contrast, if a wound contains a region that is a hollow or depression relative to the adjacent body part surface, the polyester tube can be positioned with its terminal region within this hollow or depression. The appurtenance and affixed wound dressing can then be monitored substantially similarly as described in Example 1, above.

Example 3. An Appurtenance Inserted into a Wound Dressing to Monitor Wound Healing and Infection is Constructed Using a Passive RFID Tag and Sensors Inside an Enclosure of a Height and Width to Fit Substantially within the Wound Dressing An appurtenance for a wound dressing configured to monitor wound healing and infection is constructed with an enclosure structure (as illustrated in FIGS. 5A, 5B, 6 and 7). The appurtenance to a wound dressing includes a programmable RFID sensor device. The device is constructed with a RFID device on a printed circuit board with external sensors. For example, the device can contain a dipole antenna of 22-gauge copper magnet wire, a rectifier to convert incoming UHF energy into DC, a capacitor to store the energy, and a programmable microcontroller to perform sensing and computation (see e.g., Sample et al., "Design of an RFID-Based Battery-Free Programmable Sensing Platform," *IEEE Trans. Instr. Meas.* 57: 2608-2615, 2008 which is incorporated herein by reference). The RFID device can also include multiple sensors connected to the microcontroller to detect wound healing and infection. Each sensor is in fluid communication with the lower portion of the appurtenance relative to the insertion point into the wound dressing. The sensors are located substantially within the enclosure and adjacent to an opening in the enclosure (see, e.g. FIG. 6). For example, a moisture sensor comprised of two electrodes located adjacent to an opening in the enclosure can be used to monitor the amount of fluids (e.g., exudate and blood) inside the wound dressing emanating from the wound. The electrode-based moisture sensor correlates moisture levels and impedance in the sensor (see e.g., McColl et al., "Monitoring Moisture without Disturbing the Wound Dressing," *Wounds UK* 5: 94-99, 2009 which is incorporated herein by reference). Wound moisture levels are correlated with healing, and a rapid increase in moisture level can indicate a microbial infection is present (see e.g., U.S. Pat. No. 6,963,772 to Bloom et al. titled "User-Retainable Temperature and Impedance Monitoring Methods and Devices," which is incorporated herein by reference). The RFID device includes a second sensor configured to measure the temperature of the wound dressing, and by extension the adjacent wound region. For example, an external analog temperature sensor can be connected to the microcontroller of the device and extend into the wound dressing to monitor the temperature of the wound dressing and adjacent wound region. RFID devices with external temperature sensors accurate to approximately 2° C. are described (see e.g., Sample et al., "Design of an RFID-Based Battery-Free Programmable Sensing Platform," *IEEE Trans. Instr. Meas.* 57: 2608-2615, 2008 which is incorporated herein by reference). Methods to use temperature sensors to detect the presence of microbial infections are known. For example, a thermistor-based sensor is used to monitor the temperature of a wound and indicate the presence of an infection or normal wound healing (see e.g., U.S. Pat. No. 6,963,772 to Bloom et al. titled "User-Retainable Temperature and Impedance Monitoring Methods and Devices," which is incorporated herein by reference).

The appurtenance to a wound dressing is constructed in a "thumb tack" or "rivet" shaped design (as illustrated in FIGS. 5A, 5B, 6 and 7). The device enclosure is approximately 1-2 cm in diameter at the top and includes a region approximately 5 mm long that extends into the wound dressing. The enclosure contains the thermistor-based temperature sensor which is exposed to the wound surface and the moisture sensor, both positioned adjacent to an opening in the enclosure. See FIG. 6. In addition, the appurtenance is constructed with a pressure-sensitive adhesive on the underside of the flange at the top and barbs on the projection to hold the attachment firmly in place after insertion in the bandage (see FIG. 6). Methods and materials to construct RFID tags and housings are described (see e.g., U.S. Pat. No. 6,693,513 to Tuttle, titled "Wireless Identification device, RFID Device with Push-On/Push Off Switch, and Method of Manufacturing Wireless Identification Device" and Sample et al., "Design of an RFID-Based Battery-Free Programmable Sensing Platform," *IEEE Trans. Instr. Meas.* 57: 2608-2615, 2008 which are each incorporated herein by reference).

The wound dressing appurtenance is used to monitor healing and infection of an individual's wound and to signal healthcare workers when the wound and the wound dressing need attention. The appurtenance is inserted manually in the wound dressing, and the combination unit is placed immediately over the wound to position the moisture and temperature sensors in the wound dressing proximal to the wound. The attachment receives UHF waves (e.g., approximately at 902-928 MHz) from a RFID reader in a local unit that is installed near the patient (e.g., within 10-15 meters for optimal signal from UHF waves), for example on the bed or on the wall of the hospital room. The RFID device receives UHF waves transmitted from the reader via the antenna, power harvesting circuitry, rectifying circuitry and a capacitor to empower the RFID device with direct (DC) current at approximately 1.8 volts. The power is used to drive the microcontroller which energizes the sensors, collects and computes data from the sensors and transmits a unique identification code and the collected sensor data to the RFID reader; the time and date of the signal transmission are also encoded and sent to the RFID reader. The local unit including the RFID reader includes circuitry and processors to transmit the data to a central computer where it is entered into an electronic medical record for the patient and also sent to a healthcare worker assigned to the patient or the room.

Patient information, the bandage attachment ID code and the program for signal transmission from the local unit are entered in the central computer system and verified when the bandage appurtenance is installed by an initial signal transmission from the local unit. For example, a bandage appurtenance with a designated ID number is assigned to a patient by entering the ID number into the patient's electronic medical record when the appurtenance is inserted in the patient's wound dressing. The healthcare worker can use a mobile computer, e.g., laptop computer, to enter the ID number, the type of wound, type of bandage and the interrogation schedule for the local unit. The patient information and the ID code are verified by an initial interrogation by the RFID reader within the local unit.

Example 4. A Bandage Appurtenance System is Used to Monitor Wound Dressings on a Patient with Recurrent Bacterial Infections A patient with a history of methicillin resistant *Staphylococcus aureus* (MRSA) infections is treated for a leg wound with a wound dressing and an appurtenance system that monitors the wound dressing for signs of infection and sends a signal when the wound dressing may need attention from a caregiver. The appurtenance to the wound dressing system reports data on the status of the wound dressing locally (within 10 meters of the patient) to a local unit containing a RFID reader. The local unit then processes the incoming signal and transmits information over an intranet or the internet to a central computer assembly. The appurtenance to the wound dressing system includes: an appurtenance to the wound dressing, which is a RFID sensor device; a local unit including a RFID reader which interrogates the attachment with UHF waves and receives and transmits data; and a central computer assembly which stores the data and transmits an alert for health caregivers in response to the information transmitted by the local unit.

An appurtenance to the wound dressing is constructed including a RFID device that contains a microcontroller and multiple sensors (see FIGS. 10A, 10B, 11A and 11B). Each of the sensors is substantially enclosed within a projection which extends into the wound dressing when the appurtenance is in use. The RFID device is constructed on a printed circuit board with external sensors. For example, the device can contain a dipole antenna of 22-gauge copper magnet wire, a rectifier to convert incoming UHF energy into DC, a capacitor to store the current, and a programmable microcontroller (e.g., a MSP430™ microcontroller available from Texas Instruments, Dallas, Tex.) to perform sensing and computation (see e.g., Sample et al., "Design of an RFID-Based Battery-Free Programmable Sensing Platform," *IEEE*

Trans. Instr. Meas. 57: 2608-2615, 2008 which is incorporated herein by reference). The RFID device has ports on the microcontroller to connect multiple sensors to detect wound healing and infection. The appurtenance receives UHF waves (e.g., approximately at 902-928 MHz) from a local unit containing a RFID reader that is installed near the patient (e.g., within 10-15 meters for UHF waves). A long range RFID reader operating in the UHF band with an input/output interface for the internet or the local area network is available from GAO RFID Inc., Seattle, Wash. The RFID device in the appurtenance receives UHF waves transmitted from the reader integrated into the local unit via the appurtenance antenna, power harvesting circuitry, rectifying circuitry and capacitor. The incoming UHF signal empowers the RFID device of the appurtenance with DC current at approximately 1.8 volts. The power is used to drive the microcontroller which energizes the sensors, collects and processes data from the sensors and makes a transmission. The appurtenance transmits a unique identification code with the collected sensor data to the RFID reader in the local unit; the time and date of the signal transmission are also encoded and sent to the RFID reader.

Sensors which detect moisture, temperature and *Staphylococcus aureus* proteins are placed inside hollow tubes which project from the bottom of the bandage appurtenance into the wound dressing (see FIGS. 10A, 10B, 11A and 11B). Tubes approximately 2-4 mm long, and approximately 5 mm in diameter project from the appurtenance. These projections contain the sensors and determine their effective penetration into the wound dressing. For example, a moisture sensor comprised of two electrodes which extend into the wound dressing through a projection can be used to monitor the amount of fluids (e.g., exudate and blood) emanating from the wound. Electrode-based moisture sensors are used to correlate wound moisture levels and impedance in the sensor (see e.g., McColl et al., "Monitoring Moisture without Disturbing the Wound Dressing," *Wounds UK* 5: 94-99, 2009 which is incorporated herein by reference) while wound moisture levels are correlated with healing. For example, a rapid increase in moisture level can indicate a microbial infection is present (see e.g., U.S. Pat. No. 6,963, 772 to Bloom et al. titled "User-Retainable Temperature and Impedance Monitoring Methods and Devices," which is incorporated herein by reference). A second projection tube contains a thermistor-based temperature sensor which projects to a region adjacent to the wound surface. For example, an external analog temperature sensor can be connected to the microcontroller of the device and extend into the wound dressing to monitor the temperature of the wound. The approximate distance between the wound surface and the interior of the wound dressing can be taken into account when estimating temperature of the actual wound. RFID devices with external temperature sensors accurate to approximately 2° C. are described (see e.g., Sample et al., "Design of an RFID-Based Battery-Free Programmable Sensing Platform," *IEEE Trans. Instr. Meas.* 57: 2608-2615, 2008 which is incorporated herein by reference). Methods to use temperature sensors to detect the presence of microbial infections are known. For example, a thermistor-based sensor is used to monitor the temperature of a wound and indicate the presence of an infection or normal wound healing (see e.g., U.S. Pat. No. 6,963,772 to Bloom et al. titled "User-Retainable Temperature and Impedance Monitoring Methods and Devices," which is incorporated herein by reference). An average temperature taken over time, or a graph showing temperature readings over time can be presented to a system user by the central assembly computing system.

To specifically detect *S. aureus* in the wound, a third sensor is connected to the microcontroller and inserted in a tube projecting into the wound dressing. A nano-cantilever device that signals electronically when it binds a *S. aureus* antigen is constructed using a carbon nanotube and a monoclonal antibody (see e.g., U.S. Pat. No. 7,612,424 to Espinosa and Ke titled "Nanoelectromechanical Bistable Cantilever Device," which is incorporated herein by reference). The nano-cantilever is functionalized with a monoclonal antibody specific for poly-N-acetylglucosamine (PNAG), a *S. aureus* antigen (see Kelly-Quintos et al., "Characterization of the Opsonic and Protective Activity Against *Staphylococcus aureus* of Fully Human Monoclonal Antibodies Specific for the Bacterial Surface Polysaccharide Poly-N-Acetylglucosamine" *Infection and Immunity* 74: 2742-2750 (2006) which is incorporated herein by reference). Signals from the nano-cantilever, moisture sensor and temperature sensor are received by the microcontroller and transmitted to the local unit via the integrated RFID reader.

The local unit transmits signals received from the appurtenance to the wound dressing to a central computer assembly that stores the data and alerts hospital caregivers if an infection is detected or the wound dressing needs attention. For example, if the patient's bandage appurtenance is interrogated by the RFID reader and the *S. aureus* sensor (i.e. nano-cantilever) signals that *S. aureus* antigen is detected in the wound dressing, the local unit including the RFID reader transmits the information to the central computer assembly that issues an alert (e.g., email) to the nurses and/or doctors attending to the patient. Moreover, the wound dressing data is stored in the patient's electronic health record. The local unit also has programs and circuitry to interrogate the bandage appurtenance according to a predetermined schedule and report back to the central computer assembly. The wound dressing appurtenance system interacts with healthcare personnel through the central computer assembly and records and stores information on the wound dressing, changes in the wound dressing, infections and wound healing. An individual user can query the system for information, and the system can be preset to report at a particular time (e.g. the start of the day, or the start of a medical work shift).

Example 5. An Individual with $2^{nd}$ Degree Burns on their Leg is Treated with Wound Dressings and a Wound Dressing Monitor System to Monitor the Moisture Level and Infection Status of the Burn Wounds An individual has suffered $2^{nd}$ degree burn wounds that cover approximately 200 cm² of the leg. Medical personnel have chosen an absorbent wound dressing which removes excess exudates but retains moisture in the wound. For example, an antimicrobial wound dressing (e.g., Mepilex® Ag available from Molnlycke Health Care US, LLC, Norcross, Ga.) is applied as an inner layer over the wound and a gauze dressing is applied as an absorbent outer layer to hold the inner layer dressing in place. To monitor the wound dressing, three bandage appurtenances are inserted approximately every 5 cm over the length of the wound site to monitor different areas of the burn wound. Each wound dressing appurtenance has a unique RFID identifier, a microcontroller, a moisture sensor and bacterial sensors. The placement and identification information for each appurtenance and the patient is read into the system with a local unit including an RFID reader at the time the wound dressing is placed on the patient's leg wound.

Each disposable wound dressing appurtenance includes a RFID device and a sensor with a microcontroller to direct sensing in the wound dressing. The system also includes a local unit configured to interrogate the wound dressing appurtenances and to communicate information to a central computer assembly for the wound monitoring system. A UHF RFID sensor device with a microcontroller and external sensors (see e.g., Sample et al., "Design of an RFID-Based Battery-Free Programmable Sensing Platform," *IEEE Trans. Instr. Meas.* 57: 2608-2615, 2008 which is incorporated herein by reference) is constructed with a plastic housing and projections which extend from the surface of the appurtenance into the wound dressing (see FIGS. 10A, 10B, 11A and 11B). A projection contains a moisture sensor. For example, a moisture sensor comprised of two electrodes which project into the wound dressing to reach the wound surface can be used to monitor the amount of fluids (e.g., exudate and blood) emanating from the wound. Electrode-based moisture sensors are used to correlate wound moisture levels and impedance in the sensor (see e.g., McColl et al., "Monitoring Moisture without Disturbing the Wound Dressing," *Wounds UK* 5: 94-99, 2009 which is incorporated herein by reference) and wound moisture levels are correlated with healing. For example, a rapid increase in moisture level can indicate a microbial infection is present (see e.g., U.S. Pat. No. 6,963,772 to Bloom et al. titled "User-Retainable Temperature and Impedance Monitoring Methods and Devices," which is incorporated herein by reference). Bacterial sensors to detect proteins specific to *Staphylococcus aureus* and *Pseudomonas aeruginosa*, pathogens which frequently infect burn wounds, are constructed within projections configured to extend into the wound dressing from the appurtenance surface. Information from these sensors is transmitted to the microcontroller. For example, a nano-cantilever device that signals electronically when it binds a *S. aureus* antigen is constructed using a carbon nanotube (see e.g., U.S. Pat. No. 7,612,424 to Espinosa and Ke titled "Nanoelectromechanical Bistable Cantilever Device," which is incorporated herein by reference). The nano-cantilever is functionalized with a monoclonal antibody specific for poly-N-acetylglucosamine (PNAG), a *S. aureus* antigen (see Kelly-Quintos et al., "Characterization of the Opsonic and Protective Activity Against *Staphylococcus aureus* of Fully Human Monoclonal Antibodies Specific for the Bacterial Surface Polysaccharide Poly-N-Acetylglucosamine" *Infection and Immunity* 74: 2742-2750 (2006) which is incorporated herein by reference). An equivalent nano-cantilever device to detect *P. aeruginosa* is constructed with a specific anti-*P. aeruginosa* monoclonal antibody (available from Abcam, San Francisco, Calif.). The bacterial sensors can project in different tubes or the same projection tube. When the sensors encounter bacterial antigens, a signal is transmitted to the microcontroller. A corresponding signal is then transmitted from the appurtenance to the local unit in response to a query signal from the local unit.

One part of the wound dressing becomes saturated with fluid exudates after 16 hours and the proximal moisture sensor in the appurtenance attached to that region of the wound dressing signals the local unit (programmed to interrogate the appurtenance every 4 hours) that the dressing is saturated. The local unit signals that a dressing needs attention with an LED light on the local unit and also sends a signal with information regarding the RFID identity, patient ID and moisture sensor data to a central computer assembly. The central computer assembly is configured to alert hospital personnel. The information is also automatically entered into the patient's electronic medical record by the central computer assembly.

A nurse responds to the central computer assembly alert that has been sent to the nursing station. The nurse physically inspects the wound dressing identified by the alert information. The saturated portion of the wound dressing is removed and disposed of, with the appurtenance still attached. The wound dressing is replaced and a new dressing appurtenance with a new RFID number and the patient's ID is inserted in the new wound dressing.

Example 6. Wound Dressing Appurtenance Used to Monitor a Wound Dressing on an Individual with a Venous Leg Ulcer An individual with a chronic wound, a venous leg ulcer, is treated in the patient's home with a wound dressing and a wound dressing appurtenance system to monitor the wound dressing and indicate when the dressing needs attention. Information regarding a series of wound dressings over time is also automatically saved into the patient's medical record for reference by medical personnel. The appurtenance system includes: a wound dressing appurtenance with a RFID sensor; a local unit with a RFID reader and a central computer assembly associated with the patient's clinic or hospital.

The patient's leg ulcer is treated in the patient's home in accordance with instructions from a medical caregiver, such as a nurse, who chooses a wound dressing including absorbent padding and a short stretch bandage (available from Activa Healthcare). The appurtenance is inserted into the dressing over the wound with a projection penetrating into the wound dressing. The appurtenance is fixed securely in place with adhesive on the flange of the device and by virtue of barbs on the outside of the appurtenance that affix it securely to the wound dressing.

The disposable appurtenance includes a programmable RFID sensor device. The appurtenance is constructed with a RFID tag on a printed circuit board with external sensors. For example, the appurtenance can contain a dipole antenna of 22-gauge copper magnet wire, a rectifier to convert incoming UHF energy into DC voltage, a capacitor to store the voltage, and a programmable microcontroller to perform sensing and computation (see e.g., Sample et al., "Design of an RFID-Based Battery-Free Programmable Sensing Platform," *IEEE Trans. Instr. Meas.* 57: 2608-2615, 2008 which is incorporated herein by reference). A moisture sensor comprised of two electrodes which project into the wound dressing can be used to monitor the amount of fluids (e.g., exudate and blood) emanating from the wound into the dressing. The electrode-based moisture sensor correlates moisture levels and impedance in the sensor (see e.g., McColl et al., Wounds UK 5: 94-99, 2009 which is incorporated herein by reference). Wound moisture levels are correlated with healing, and a rapid increase in moisture level, can indicate a microbial infection is present (see e.g., U.S. Pat. No. 6,963,772 issued to Bloom et al. on Nov. 8, 2005 which is incorporated herein by reference).

The nurse installs the appurtenance system in the patient's home to allow remote monitoring of the leg ulcer. After manually pushing the appurtenance into the wound dressing, a local unit is used to query the appurtenance for its unique identification code and then to monitor the appurtenance. A local unit including a mobile RFID reader is installed in the patient's home. For example, a long range RFID reader operating in the UHF band with an input/output interface for the internet is available from GAO RFID Inc. The local unit transmits UHF waves (e.g., approximately at 902-928 MHz) from the bedside, a chair, or a table (e.g., within 10-15 meters of the wound dressing with the affixed appurtenance). The local unit is programmed by the nurse using a laptop computer to enter the RFID number, patient identification, and schedule for appurtenance interrogation (e.g., every 2 hours). The nurse also establishes a link between the local unit and a central computer assembly affiliated with the hospital or clinic. For example, a link to the patient's internet service is established to transmit data from the local unit to the central computer assembly. Information from the local unit can also be configured to automatically be included in the patient's electronic health record by the central computer assembly.

If the moisture sensor of the appurtenance detects excess moisture in the wound dressing, an alert is signaled to the patient and the hospital's central computer. The local unit receives a signal of excess moisture (i.e., low impedance) from the moisture sensor in the appurtenance and an LED on the local unit alerts the patient or a family member that the wound dressing needs attention. Also the local unit transmits the signal of excess moisture to the central computer assembly where an alert (e.g., an e-mail) is created for the nurses on duty.

The nurse receiving the alert can contact the patient and/or the patient can phone the nurse when the LED on the local unit lights up. The nurse can recommend the patient change the dressing or visit the patient to change the dressing and inspect the wound directly. The nurse, the patient or another caregiver can change the dressing and insert a new appurtenance in the dressing over the wound site. The new dressing appurtenance is verified by interrogating the new appurtenance with the local unit and the information is sent to the central computer assembly.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An appurtenance to an unpenetrated wound dressing, comprising:
    a substrate configured to mechanically or chemically attach to the unpenetrated wound dressing;
    a transmission unit attached to a surface of the substrate, the transmission unit including circuitry and at least one antenna, the transmission unit configured to transmit a signal;
    a hollow tubular projection operably attached to the transmission unit, the hollow tubular projection having an exterior wall defining a channel, the exterior wall being of a size and shape to penetrate the unpenetrated wound dressing and extend into an interior region of the unpenetrated wound dressing and configured to sample a fluid associated with a wound, wherein a portion of the exterior wall of the hollow tubular projection configured to penetrate the unpenetrated wound dressing is oriented at an obtuse or acute angle relative to the substrate; and
    one or more sensors disposed in a portion of the hollow tubular projection that is configured to penetrate the unpenetrated wound dressing, wherein the one or more sensors are configured to detect one or more characteristics of the unpenetrated wound dressing or an individual using the unpenetrated wound dressing.

2. The appurtenance to an unpenetrated wound dressing of claim 1, wherein the substrate comprises:
    a flexible material.

3. The appurtenance to an unpenetrated wound dressing of claim 1, wherein the transmission unit is configured to transmit the signal in response to an interrogation signal.

4. The appurtenance to an unpenetrated wound dressing of claim 1, wherein the transmission unit comprises:
    a transmitter unit; and
    a receiver.

5. The appurtenance to an unpenetrated wound dressing of claim 1, wherein the transmission unit comprises:
    a radio frequency identification (RFID) device.

6. The appurtenance to an unpenetrated wound dressing of claim 1, wherein the transmission unit comprises:
    at least two antennas.

7. The appurtenance to an unpenetrated wound dressing of claim 1, wherein the transmission unit comprises:
    a Near Field Communication (NFC) device.

8. The appurtenance to an unpenetrated wound dressing of claim 1, wherein the hollow tubular projection comprises:
    a physical conduit configured for fluid flow from the interior region of the unpenetrated wound dressing to a location in contact with the transmission unit.

9. The appurtenance to an unpenetrated wound dressing of claim 1, wherein the hollow tubular projection comprises:
    one or more additional sensors; and
    at least one substantially hollow enclosure substantially encircling the one or more additional sensors, the at least one substantially hollow enclosure including one or more openings within the enclosure distal to an attachment to the substrate.

10. The appurtenance to an unpenetrated wound dressing of claim 1, wherein the one or more sensors are partially internal to the hollow tubular projection.

11. The appurtenance to an unpenetrated wound dressing of claim 1, wherein the one or more sensors are configured to actuate a switch in the transmission unit in response to a stimulus.

12. The appurtenance to an unpenetrated wound dressing of claim 1, comprising:
    a connector between the transmission unit and the one or more sensors.

13. The appurtenance to an unpenetrated wound dressing of claim 1, comprising:
    an indicator operably attached to the transmission unit.

14. The appurtenance to an unpenetrated wound dressing of claim 1, wherein the hollow tubular projection has a curvilinear shape.

15. The appurtenance to an unpenetrated wound dressing of claim 14, wherein the tubular projection has a hook shape.

16. The appurtenance to an unpenetrated wound dressing of claim 1, further comprising another hollow tubular projection that is non-parallel relative to the hollow tubular projection.

17. The appurtenance to an unpenetrated wound dressing of claim 1, further comprising an outer cover configured to be attached to the substrate and to the unpenetrated wound dressing, wherein the outer cover is configured to be attached to a portion of the substrate at or near the hollow tubular projection.

18. The appurtenance to an unpenetrated wound dressing of claim 17, wherein the outer cover is configured to seal a juncture between the appurtenance and the wound dressing.

19. An appurtenance to an unpenetrated wound dressing, comprising:
a substrate configured to mechanically or chemically attach to the wound dressing; a transmission unit attached to a surface of the substrate, the transmission unit including circuitry and at least one antenna, the transmission unit configured to transmit a signal;
a projection configured to be attached to the transmission unit and having a barb-shaped feature extending outward from the projection an acute angle, and configured to secure the appurtenance to the wound dressing, the projection of a size and shape to extend into an interior region of the unpenetrated wound dressing and configured to sample a fluid associated with a wound, wherein a portion of the projection that is configured to extend into an interior region of the unpenetrated wound dressing is oriented at an obtuse or acute angle relative to the substrate; and
an outer cover configured to be attached to the substrate and to the unpenetrated wound dressing, wherein the outer cover is configured to be attached to a portion of the substrate at or near the projection.

20. The appurtenance to an unpenetrated wound dressing of claim 19, wherein the barb-shaped feature is configured to bend during insertion into the wound dressing.

21. The appurtenance to an unpenetrated wound dressing of claim 19, wherein the projection is tubular.

22. The appurtenance to an unpenetrated wound dressing of claim 19, further comprising one or more sensors disposed in a portion of the hollow tubular projection that is configured to penetrate the unpenetrated wound dressing, wherein the one or more sensors are configured to detect one or more characteristics of the unpenetrated wound dressing or an individual using the unpenetrated wound dressing.

* * * * *

UNITED STATES PATENT AND TRADEMARK OFFICE
CERTIFICATE OF CORRECTION

PATENT NO.         : 10,158,928 B2
APPLICATION NO.    : 13/445174
DATED              : December 18, 2018
INVENTOR(S)        : Paul Duesterhoft et al.

Page 1 of 1

It is certified that error appears in the above-identified patent and that said Letters Patent is hereby corrected as shown below:

In the Claims

Column 54, Claim 22, Line 16:
"posed in a portion of the hollow tubular projection that is"
Should read:
--posed in a portion of the projection that is--

Signed and Sealed this
Twenty-sixth Day of February, 2019

Andrei Iancu
*Director of the United States Patent and Trademark Office*